(12) United States Patent
Torres

(10) Patent No.: US 11,270,790 B2
(45) Date of Patent: Mar. 8, 2022

(54) METHODS FOR THE DIAGNOSIS AND TREATMENT OF NEUROLOGICAL DISORDERS

(71) Applicant: Rutgers, The State University of New Jersey, New Brunswick, NJ (US)

(72) Inventor: Elizabeth B. Torres, Piscataway, NJ (US)

(73) Assignee: RUTGERS, THE STATE UNIVERSITY OF NEW JERSEY, New Brunswick, NJ (US)

(*) Notice: Subject to any disclaimer, the term of this patent is extended or adjusted under 35 U.S.C. 154(b) by 486 days.

(21) Appl. No.: 16/212,058

(22) Filed: Dec. 6, 2018

(65) Prior Publication Data

US 2019/0333629 A1 Oct. 31, 2019

Related U.S. Application Data

(63) Continuation of application No. 14/354,796, filed as application No. PCT/US2012/064805 on Nov. 13, 2012, now Pat. No. 10,176,299.
(Continued)

(51) Int. Cl.
*G16H 20/70* (2018.01)
*A61B 5/16* (2006.01)
(Continued)

(52) U.S. Cl.
CPC ........... *G16H 20/70* (2018.01); *A61B 5/0015* (2013.01); *A61B 5/11* (2013.01); *A61B 5/162* (2013.01); *A61B 5/168* (2013.01); *A61B 5/40* (2013.01); *A61B 5/4076* (2013.01); *A61B 5/7264* (2013.01); *G16H 40/20* (2018.01); *G16Z 99/00* (2019.02); *A61B 5/1104* (2013.01); *A61B 5/1114* (2013.01); *A61B 5/1124* (2013.01); *A61B 5/1125* (2013.01); *A61B 5/1128* (2013.01); *A61B 5/4082* (2013.01); *A61B 5/4088* (2013.01); *A61B 5/4094* (2013.01); *A61B 5/4848* (2013.01); *A61B 5/7275* (2013.01); *A61B 5/7278* (2013.01); *G16H 10/60* (2018.01); *G16H 50/20* (2018.01); *H04L 63/0428* (2013.01)

(58) Field of Classification Search
CPC ....... A61B 5/11; A61B 5/1104; A61B 5/1124; A61B 5/162; A61B 5/168; A61B 5/40; A61B 5/4076; A61B 5/4082; A61B 5/4848; A61B 5/7264; G16H 20/70
See application file for complete search history.

(56) References Cited

U.S. PATENT DOCUMENTS 6,231,527 B1  5/2001  Sol
6,719,690 B1  3/2004  Cassily
(Continued)

OTHER PUBLICATIONS

Blake, et al, "Visual recognition of biological motion is impaired in children with autism", Physchol. Sci., vol. 14, pp. 1-7 (2003).
(Continued)

*Primary Examiner* — Devin B Henson
(74) *Attorney, Agent, or Firm* — Wolter Van Dyke Davis, PLLC; Eugene J. Molinelli

(57) ABSTRACT

The present invention provides objective methods of diagnosis and behavioural treatments of neurological disorders such as autism spectral disorders and Parkinson's disease.

12 Claims, 38 Drawing Sheets

Related U.S. Application Data

(60) Provisional application No. 61/648,359, filed on May 17, 2012, provisional application No. 61/581,953, filed on Dec. 30, 2011, provisional application No. 61/558,957, filed on Nov. 11, 2011.

(51) Int. Cl.
| | |
|---|---|
| *A61B 5/11* | (2006.01) |
| *A61B 5/00* | (2006.01) |
| *G16Z 99/00* | (2019.01) |
| *G16H 40/20* | (2018.01) |
| *G16H 10/60* | (2018.01) |
| *G16H 50/20* | (2018.01) |
| *H04L 29/06* | (2006.01) |

(56) References Cited

U.S. PATENT DOCUMENTS

| | | | |
|---|---|---|---|
| 7,819,818 B2 * | 10/2010 | Ghajar | A61B 3/113 |
| | | | 600/558 |
| 8,808,195 B2 | 8/2014 | Tseng et al. | |
| 9,412,161 B2 * | 8/2016 | Varaklis | G16H 20/30 |
| 2009/0192417 A1 | 7/2009 | Mon-Williams et al. | |
| 2010/0106517 A1 | 4/2010 | Kociubinski et al. | |
| 2010/0208205 A1 * | 8/2010 | Tseng | G06K 9/4628 |
| | | | 351/209 |
| 2011/0054361 A1 | 3/2011 | Sakoda et al. | |
| 2011/0066082 A1 | 3/2011 | Duffy | |
| 2011/0213277 A1 * | 9/2011 | McNames | A61B 5/1124 |
| | | | 600/595 |
| 2011/0242486 A1 | 10/2011 | Ebisawa | |
| 2012/0083705 A1 | 4/2012 | Yuen et al. | |

OTHER PUBLICATIONS

Faisal, "Noise in the nervous system", Nat. Rev. Neurosci., vol. 9, pp. 292-303 (2008).
Fuentes, et al, "No. proprioceptive deficits in autism despite movement-related sensory and execution impairments", J. Autism Dev. Disord., vol. 41, pp. 1352-1361 (2010).
Haswell, et al, "Representation of internal models of action in the autistic brain", Nat. Neurosci., vol. 12, Issue 8, pp. 970-972 (2009).
Isenhower, et al, "Physical metrics of fluency training and task complexity in the natural movements of children with autism spectrum disorder gauge learning in the classroom environment", Neuroscience, pp. 1-2 (2011).
Jose, et al, "Statistical classification tools for spectral disorders based on motor variability: Application to autism and Parkinson's disorders", Neuroscience, pp. 1-2 (2011).
Kaiser, et al, "The visual perception of motion by observers with autism spectrum disorders: a review and synthesis", Psychon. Bull Rev., vol. 16, pp. 761-777 (2009).
Minshew, et al, "Underdevelopment of the postural control system in autism", Neurology, vol. 63, pp. 2056-2061 (2004).
Muller, R, "The study of autism as a distributed disorder", Mental Retardation and developmental Disabilities Research Reviews, vol. 13, pp. 85-95 (2007).
Redgrave, et al, "Goal-directed and habitual control in the basal ganglia: implications of parkinson's disease", Nat. Rev. Neurosci., vol. 11, Issue 11, pp. 760-772 (2010).
Torres, "Atypical signatures of motor variability found in an individual with ASD", Neurocase., vol. 19, Issue 2, pp. 150-165 (2013).
Torres, et al, "Impaired endogenously evoked automated reaching in Parkinson's disease", J Neurosci., vol. 31, Issue 49, pp. 17848-17863 (2011).
Torres, et al, "New symmetry of intended curved reaches", Behavioral and Brain functions, vol. 6, Issue 21, pp. 1-20 (2010).
Torres, et al, "Sensory-spatial transformations in the left posterior parietal cortex may contribute to reach timing", J. Neurophysiol., vol. 104, pp. 2375-2388 (2010).
Torres, et al, "Simultaneous control of hand displacements and rotations in orientation-matching experiments", J Appl Physiol, vol. 96, Issue 5, pp. 1978-1987 (2004).
Torres, et al, Space-time separation during obstacle-avoidance learning in monkeys, J. Neuropyhsiol., vol. 96, pp. 2613-2632 (2006).
Torres, et al, "Two classes of movements in motor control", Exp Brain Res, vol. 215, pp. 269-283 (2011).
Vakalopoulous, et al, "Unilateral neglect: a theory of proprioceptive space of a stimulus as determined by the cerebellar component of motor efference copy (and is autism a special case of neglect)", Med. Hypotheses, vol. 68, pp. 574-600 (2007).
Van Beers, et al, "The role of execution noise in movement variability", J. Neurophysiol., vol. 91, Issue 2, pp. 1050-1053 (2004).
Torres, "Signatures of movement variability anticipate hand speed according to levels of intent," Torres Behavioral and Brain Functions 2013, pp. 1-20; 9:10.

\* cited by examiner

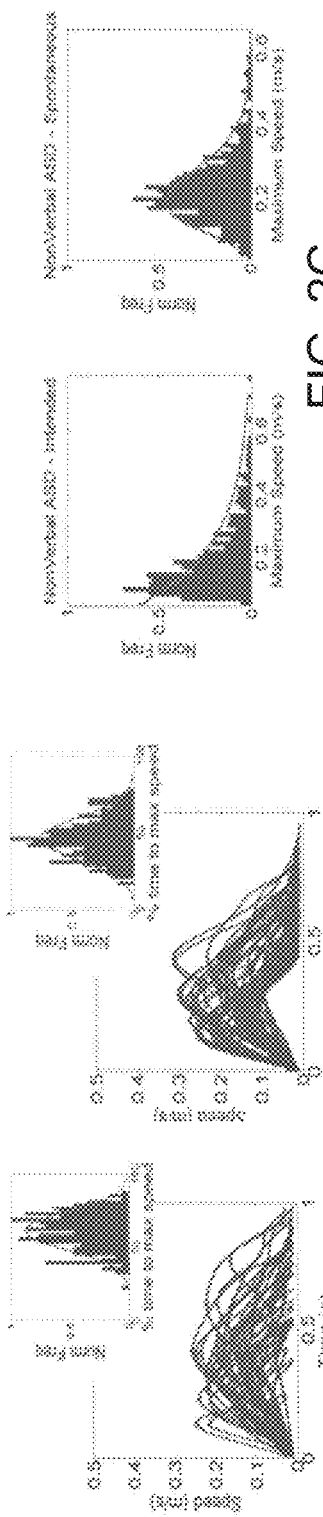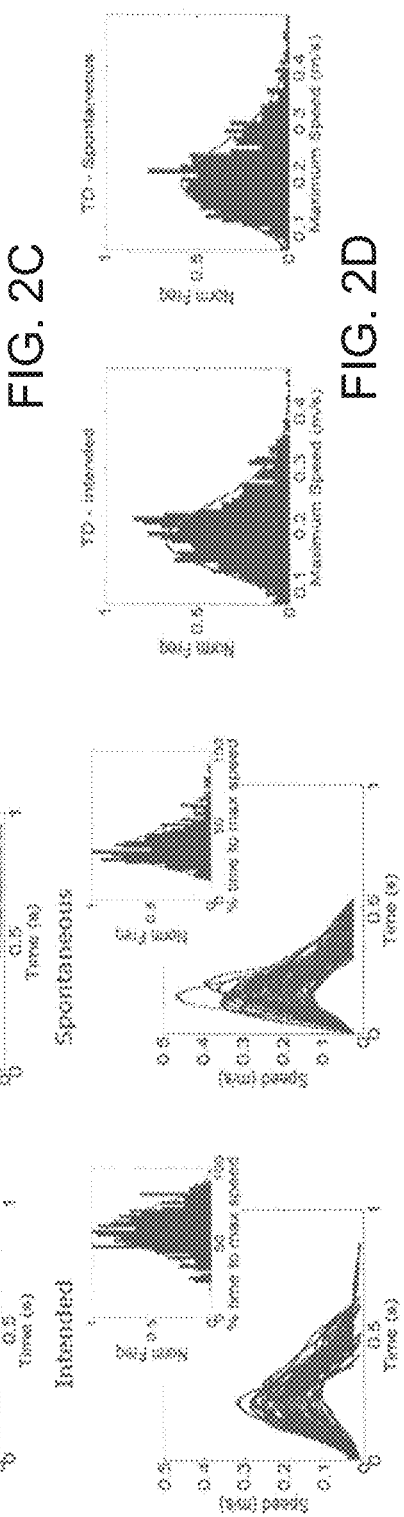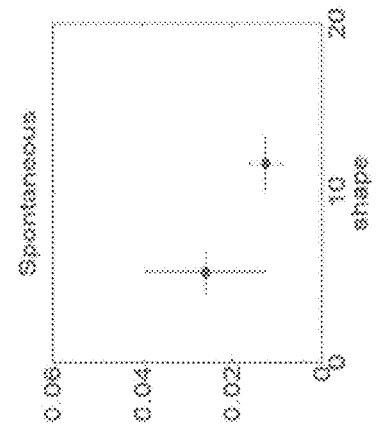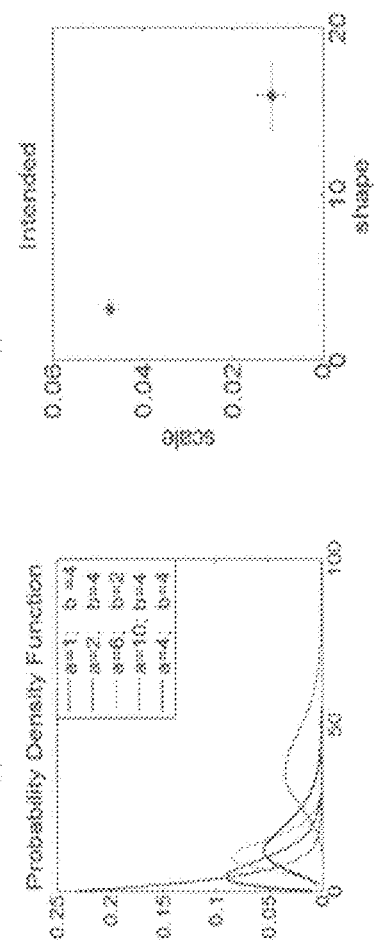

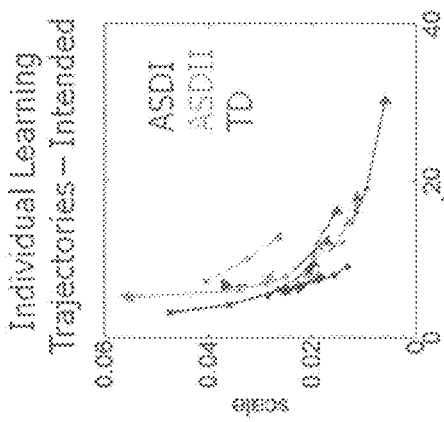
FIG. 3A
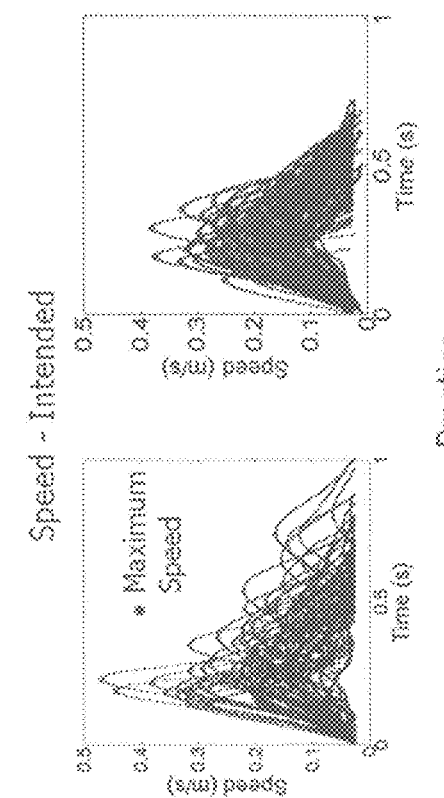
FIG. 3C
FIG. 3D
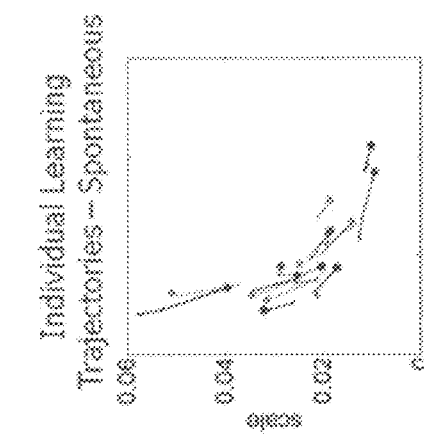
FIG. 3E
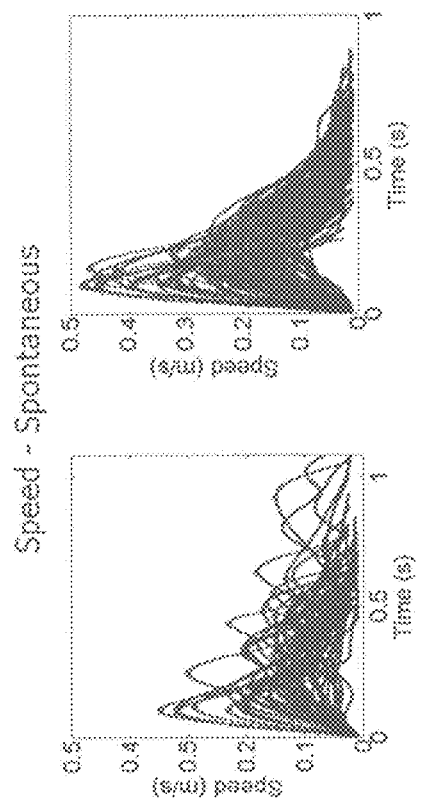
FIG. 3F
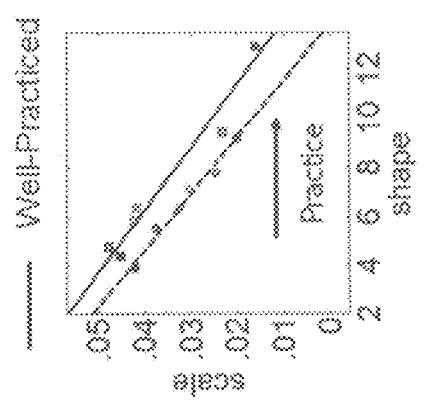
FIG. 3B

 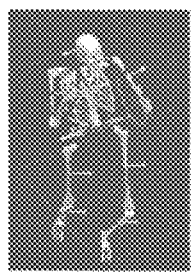   
FIG. 8A   FIG. 8B   FIG. 8C   FIG. 8D   FIG. 8E
 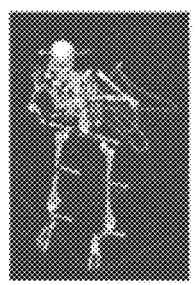   
FIG. 8F   FIG. 8G   FIG. 8H   FIG. 8I   FIG. 8J
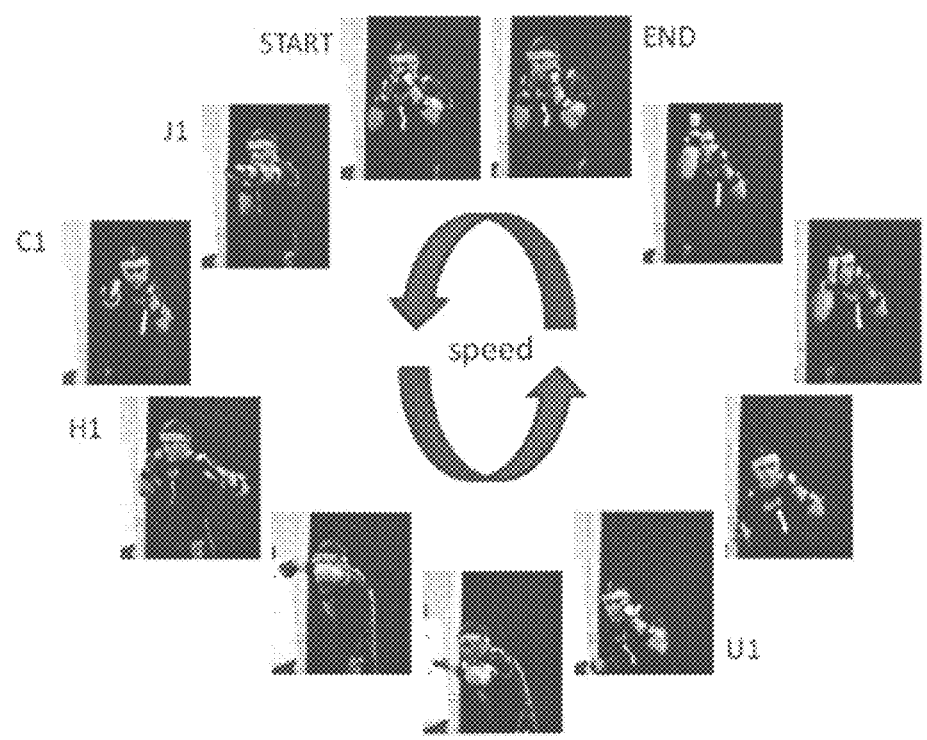
FIG. 8K

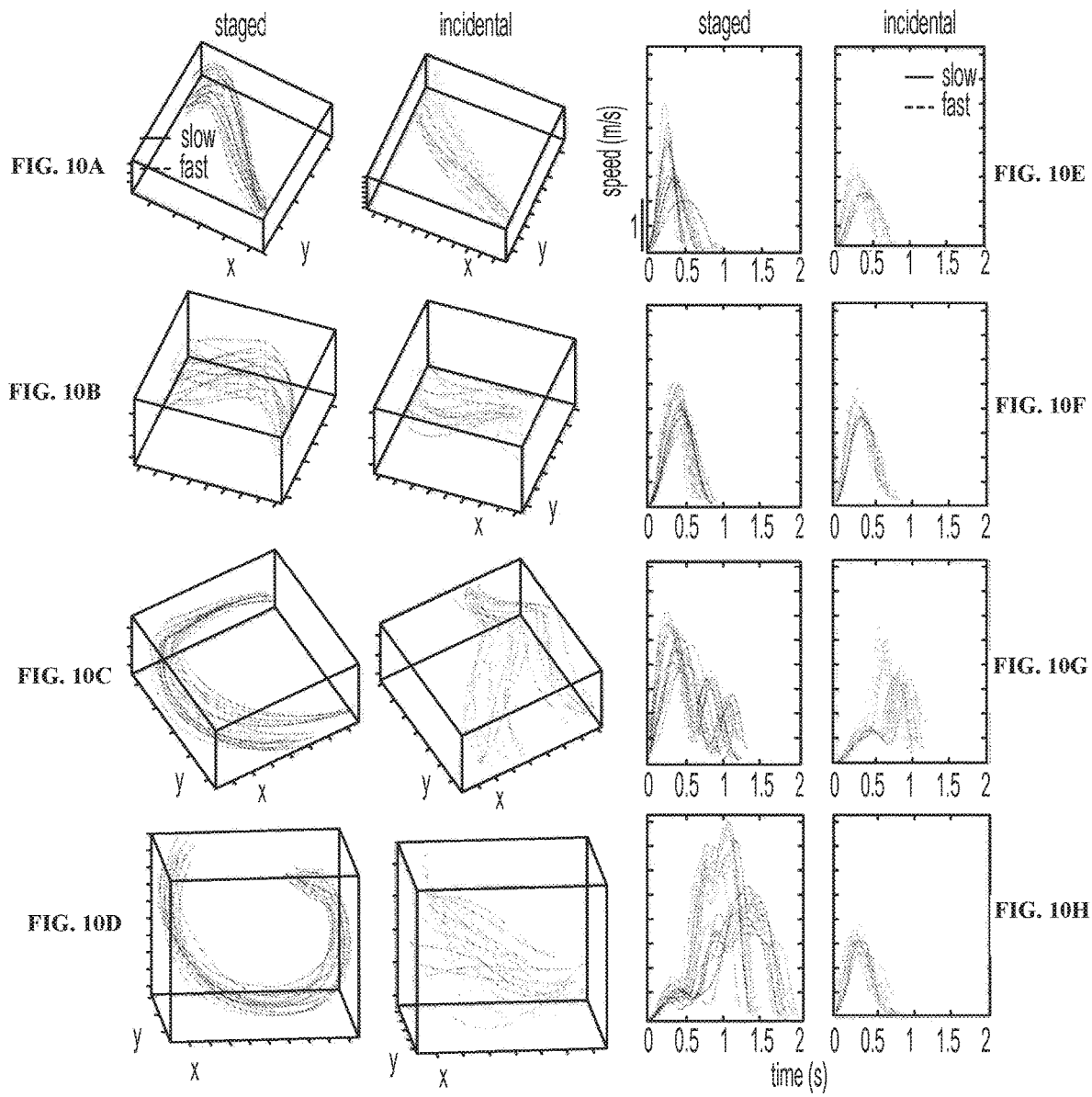

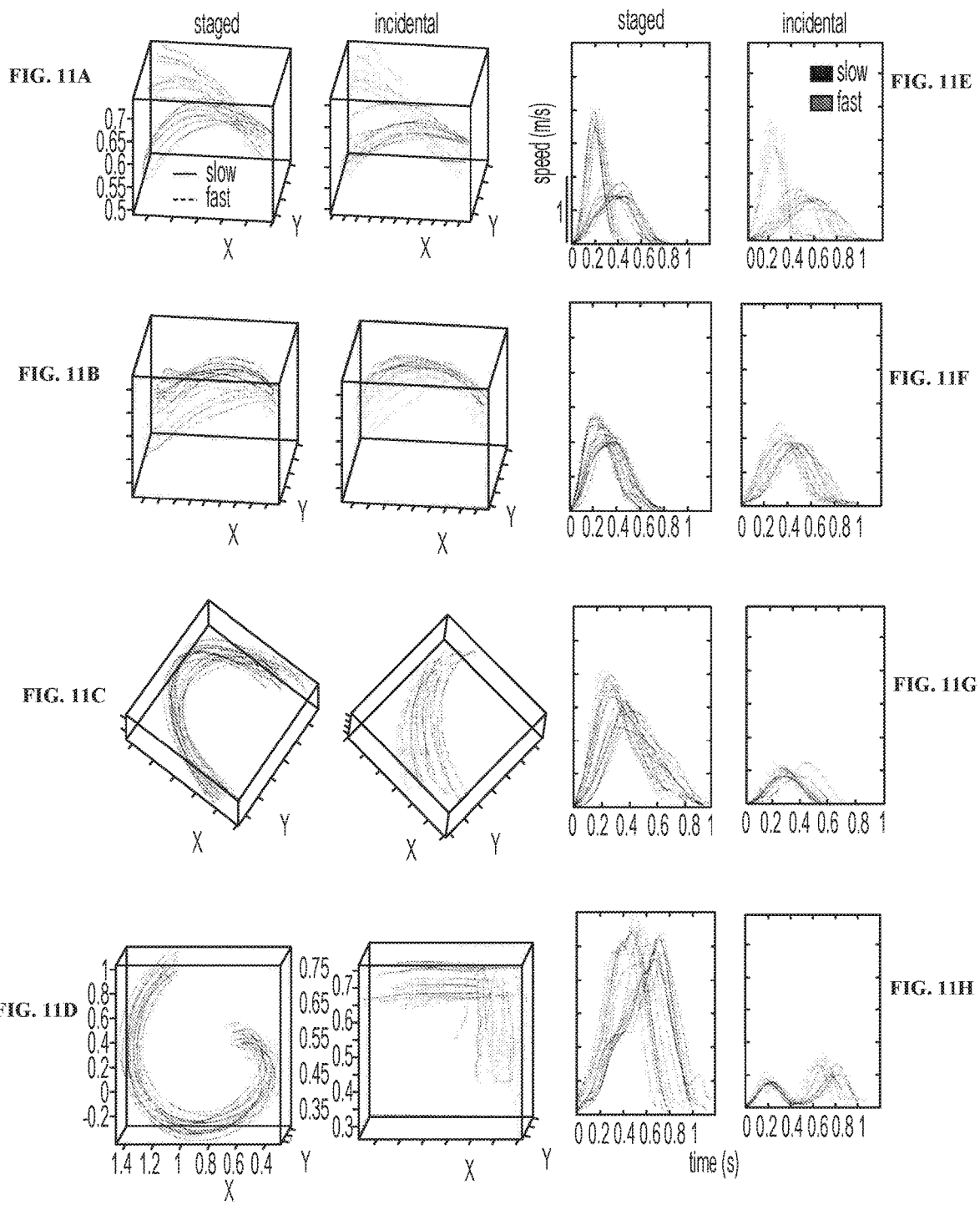

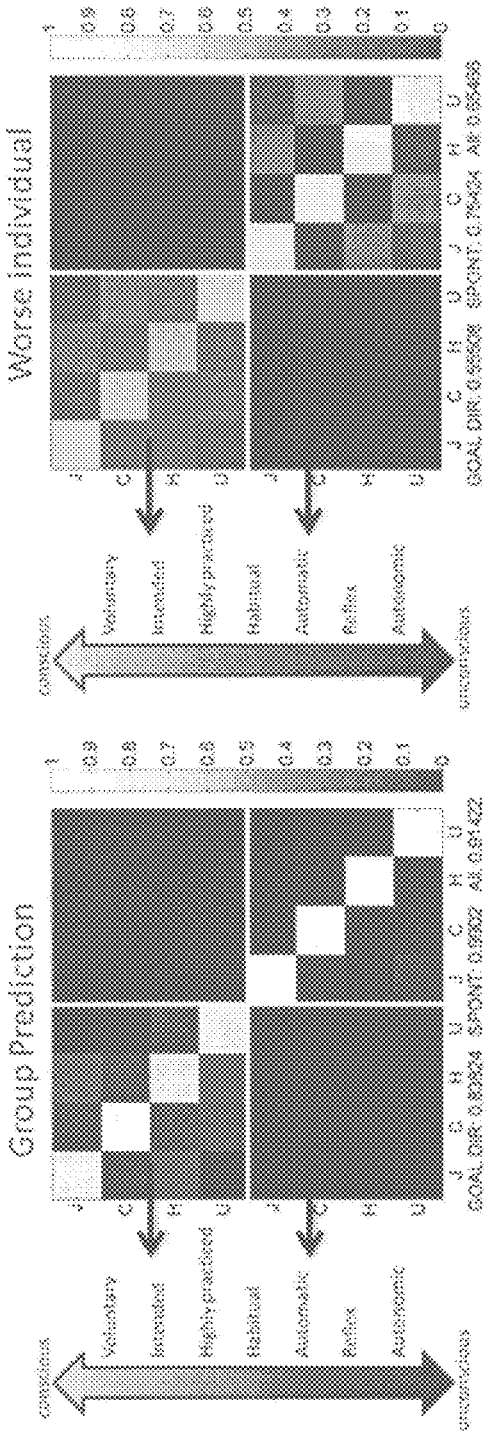
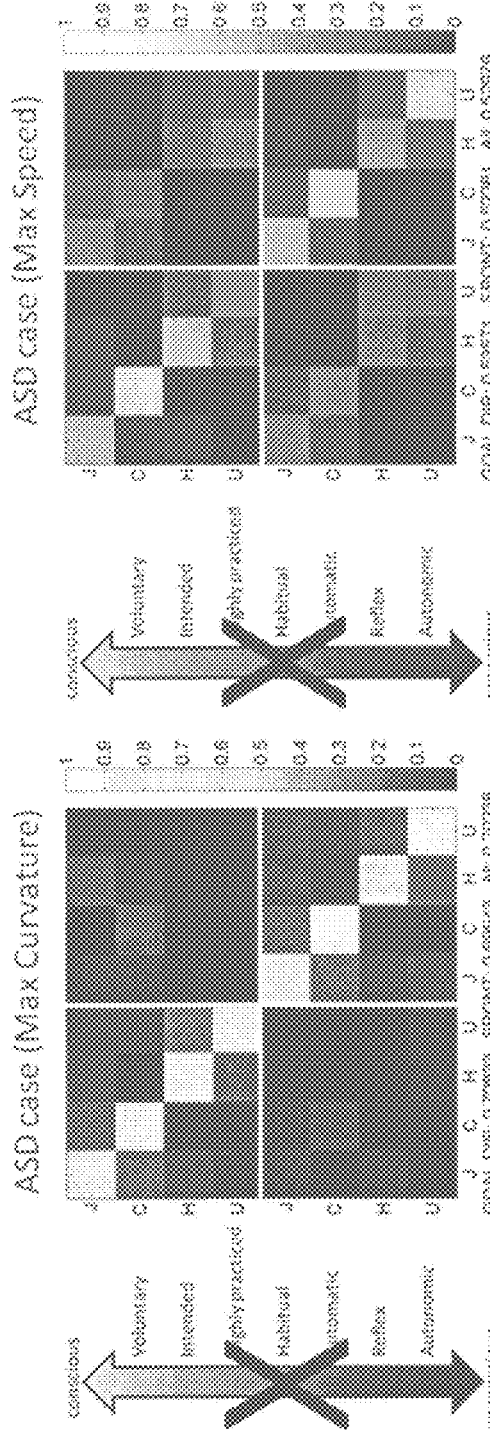
FIG. 12A
FIG. 12B
FIG. 12C
FIG. 12D

FIG. 14A
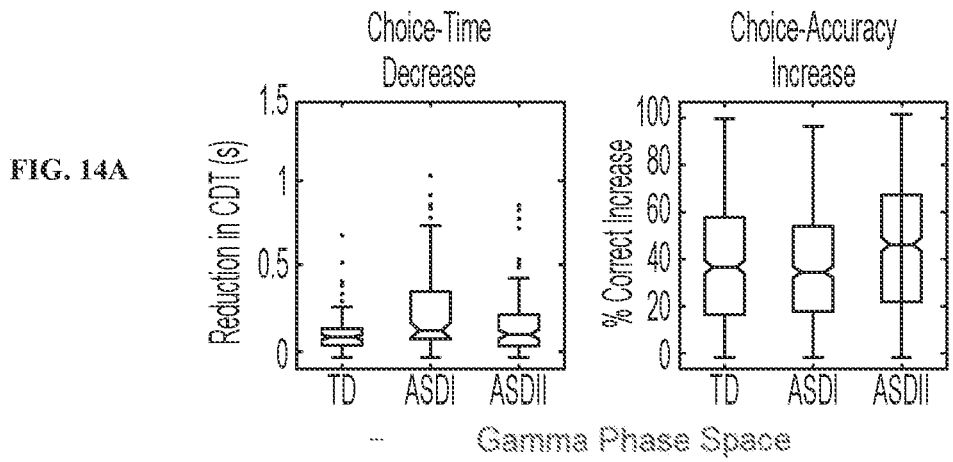
FIG. 14B
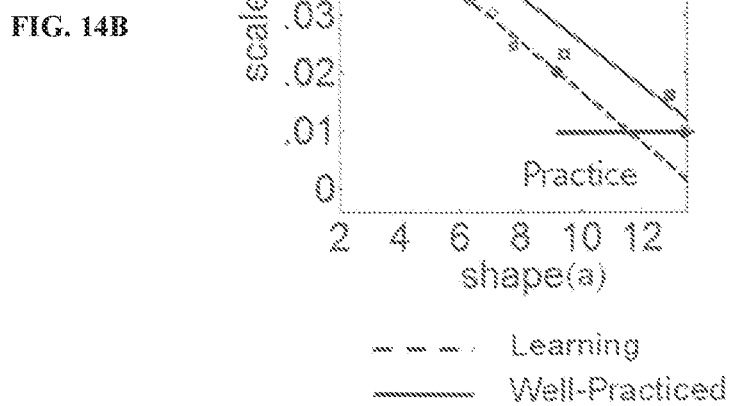
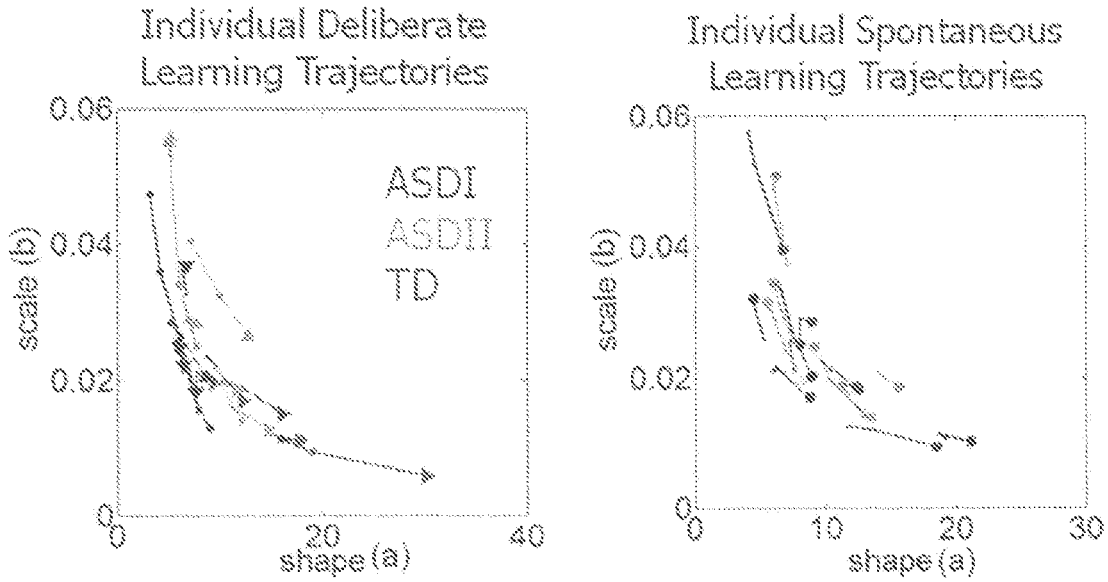
FIG. 14C

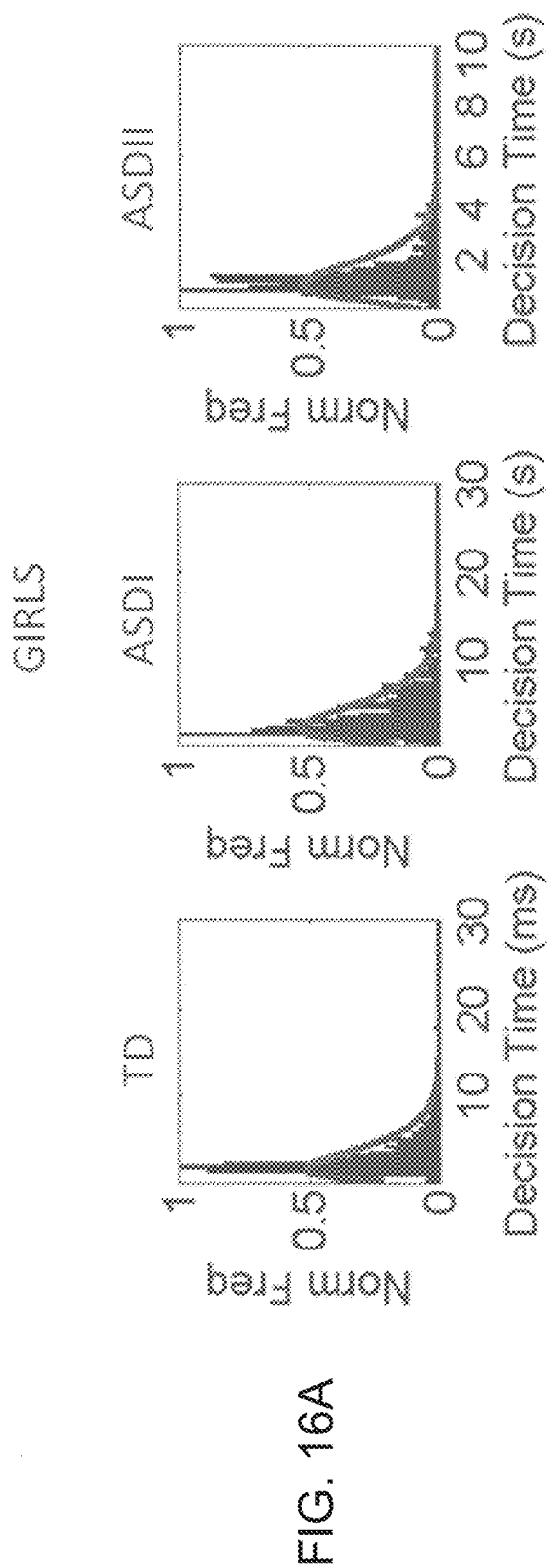
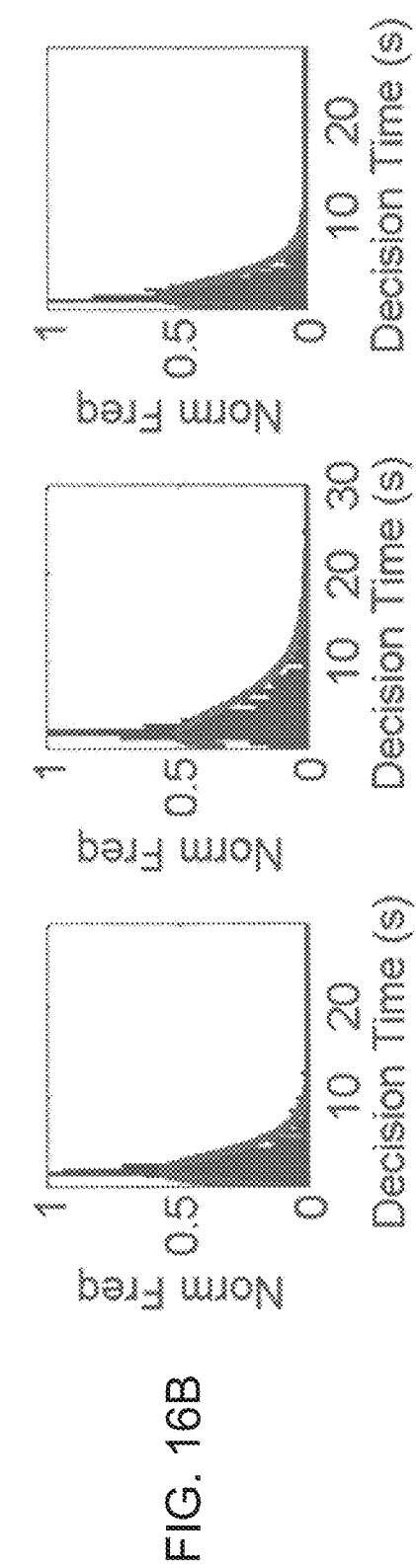
FIG. 16A
FIG. 16B

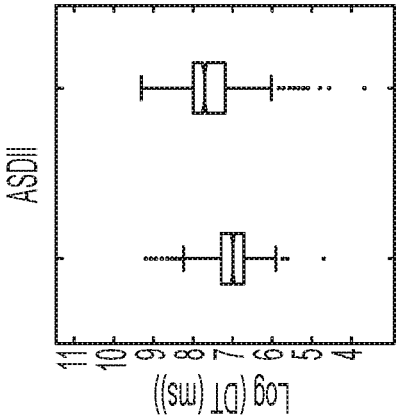
FIG. 17A
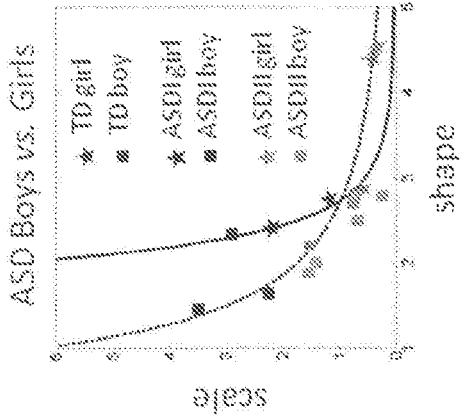
FIG. 17B
FIG. 17C
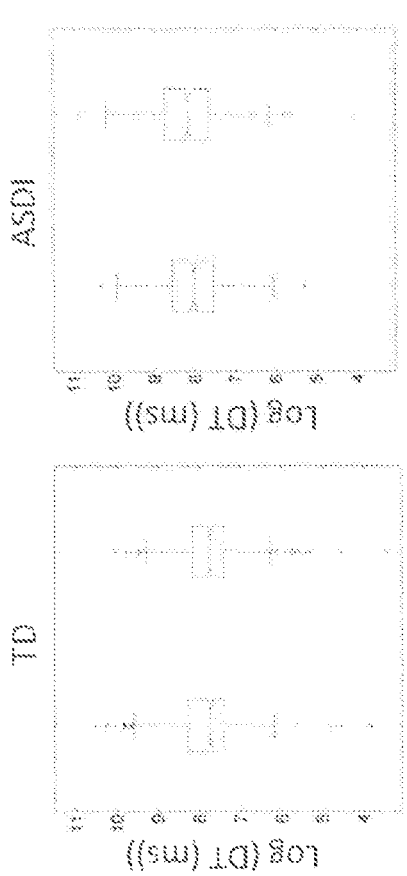
FIG. 17D
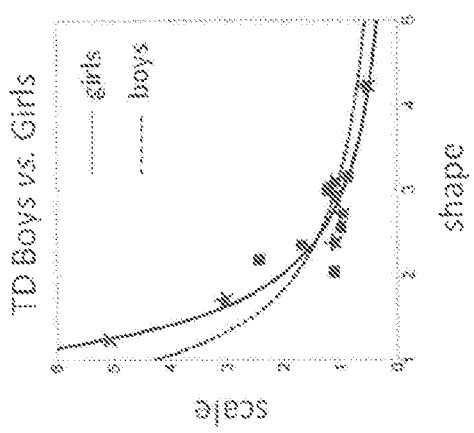
FIG. 17E
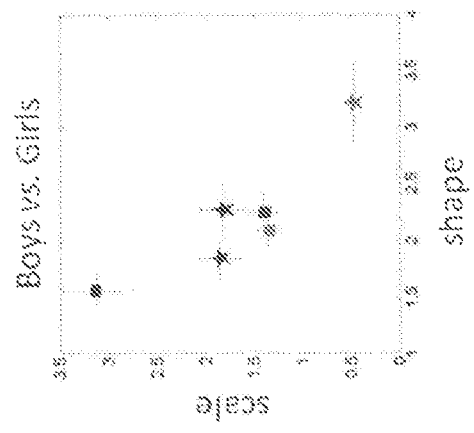
FIG. 17F

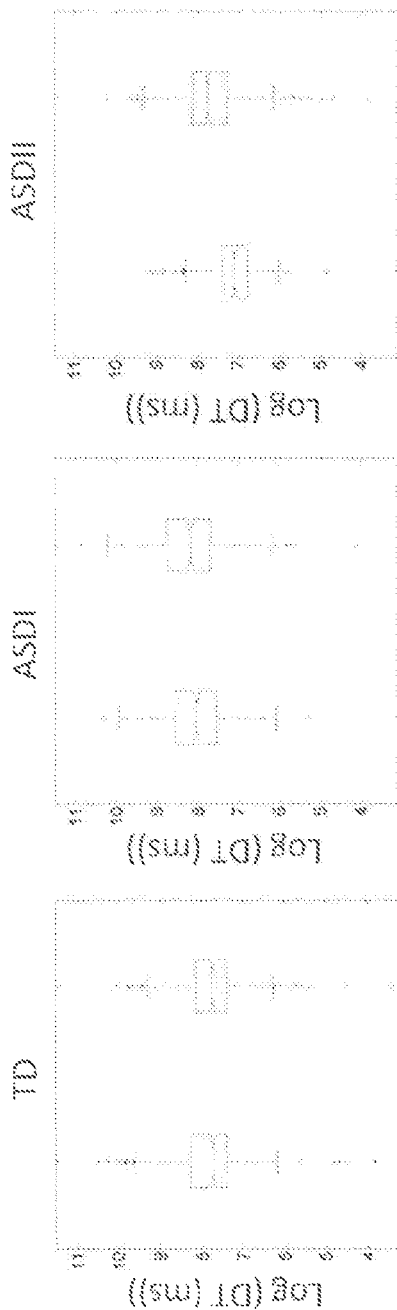
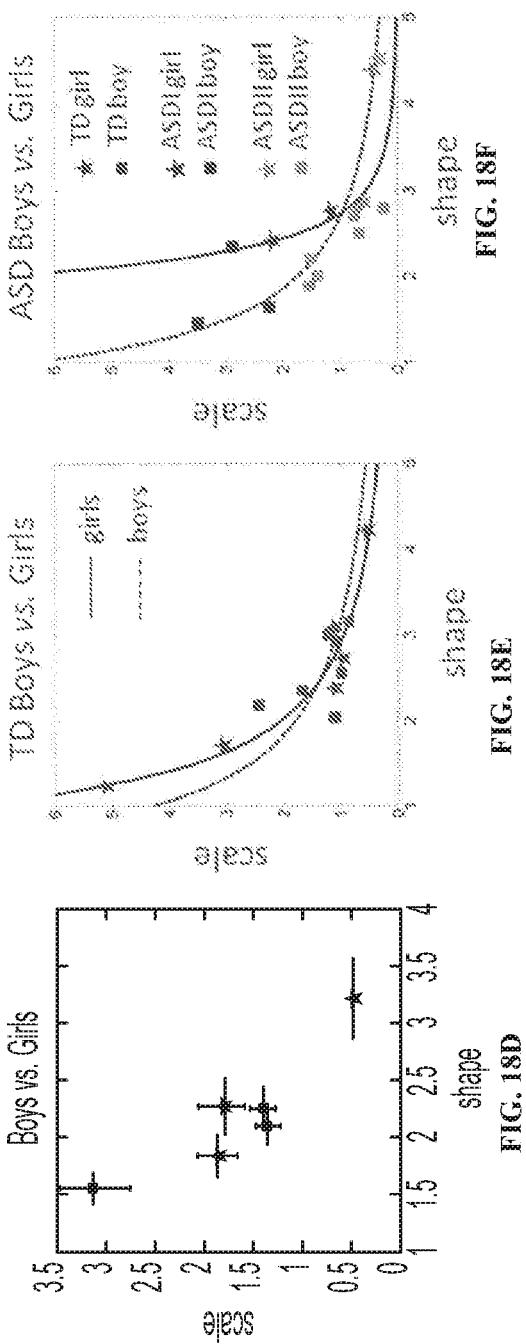

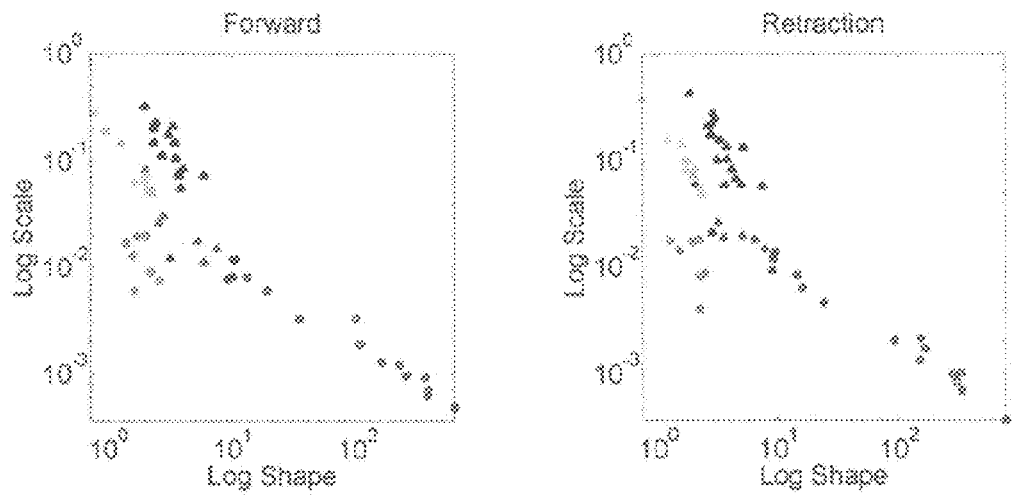
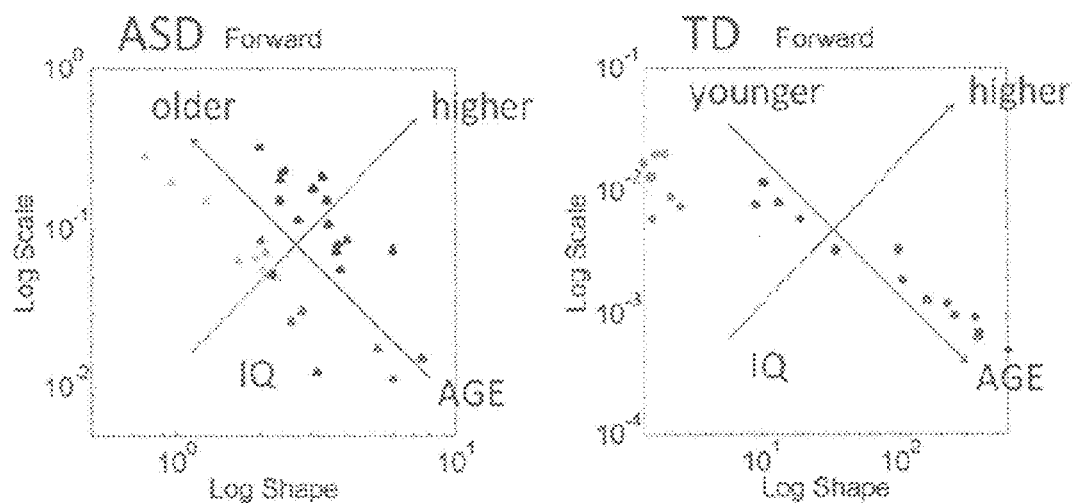
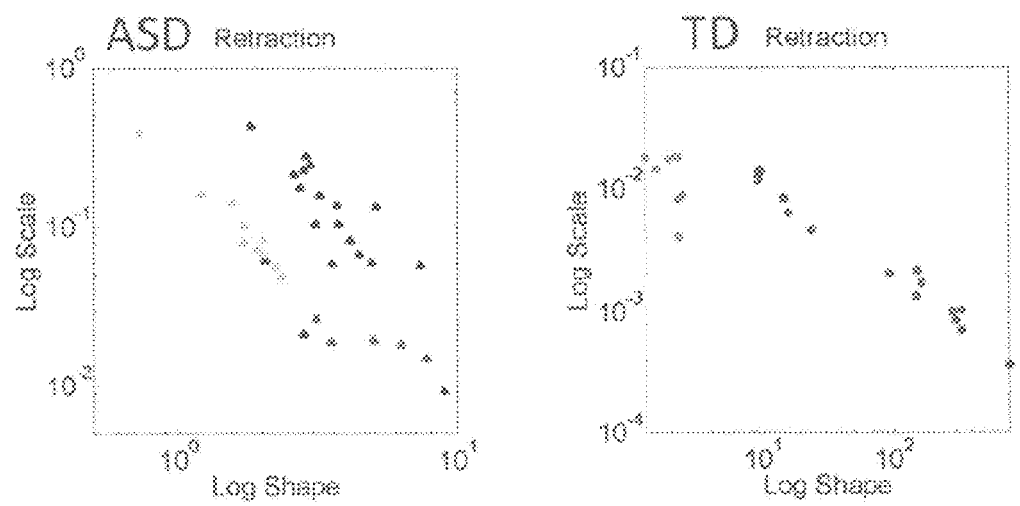
FIG. 20B

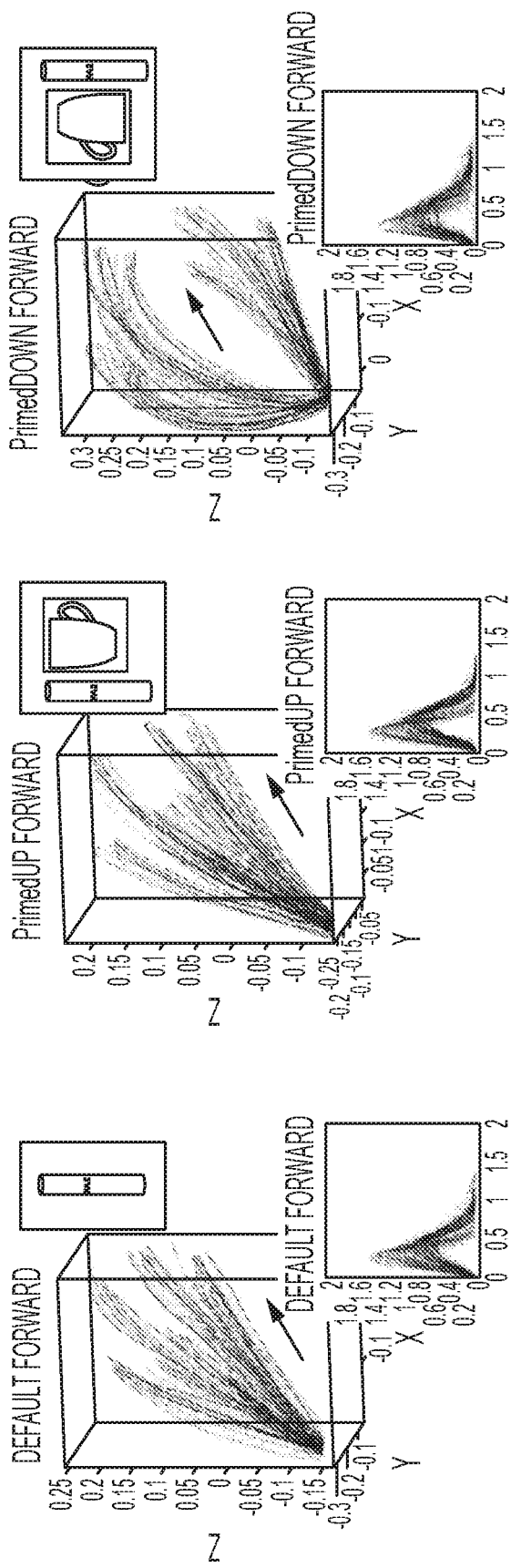
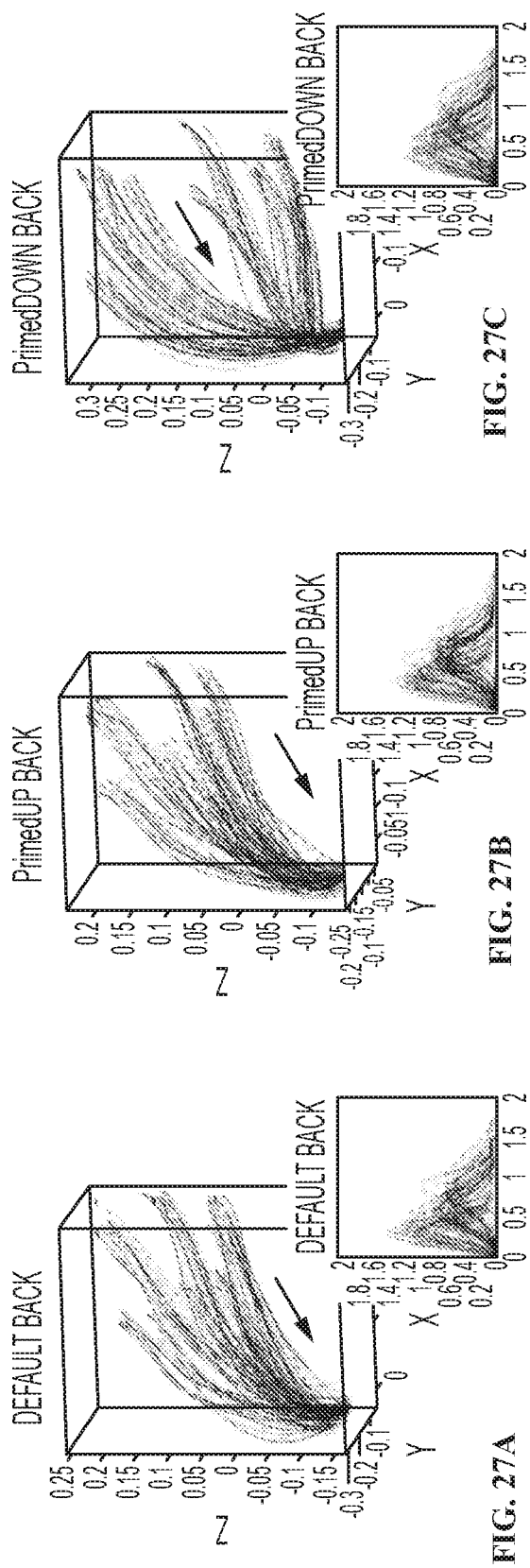
FIG. 27A
FIG. 27B
FIG. 27C

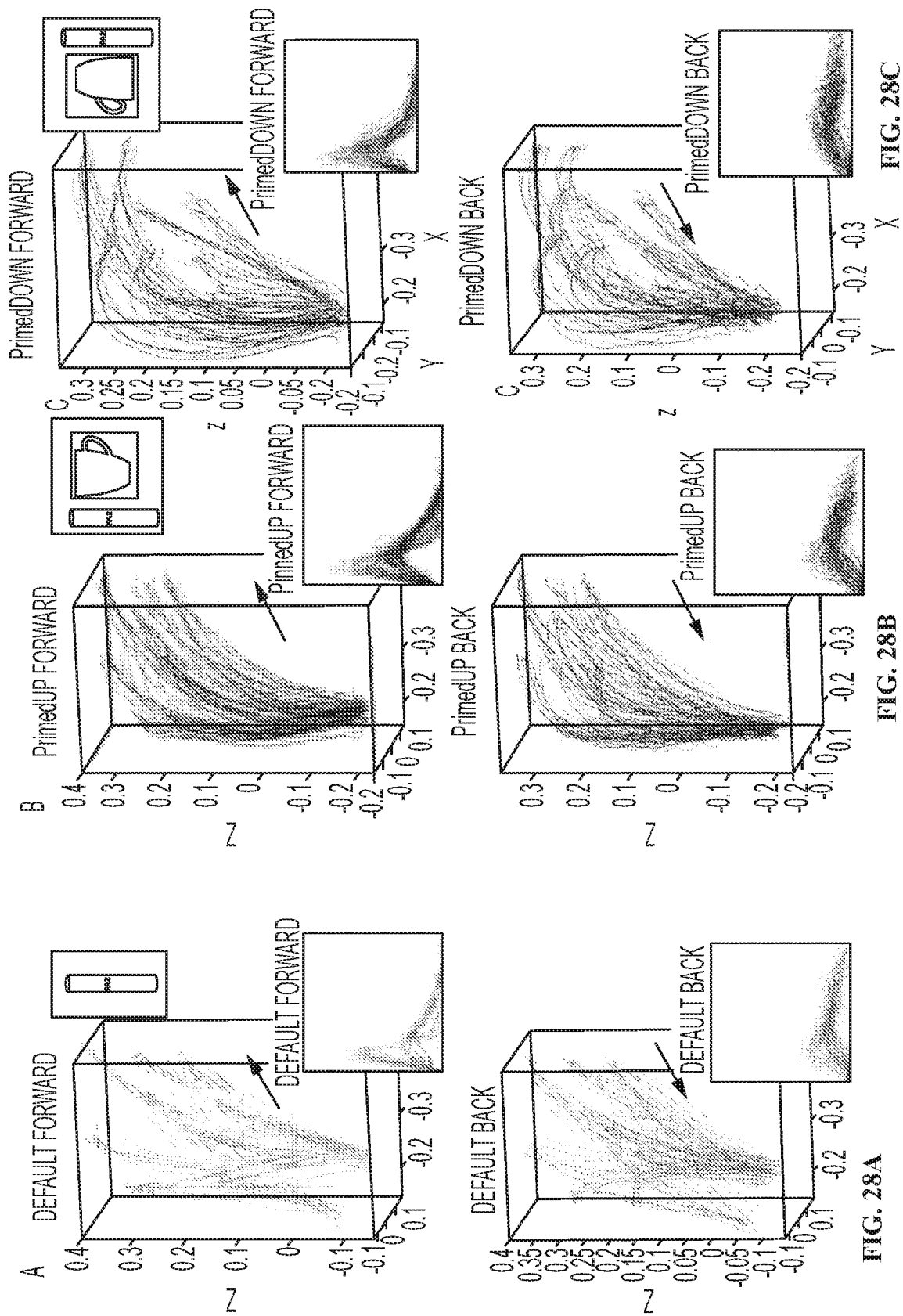

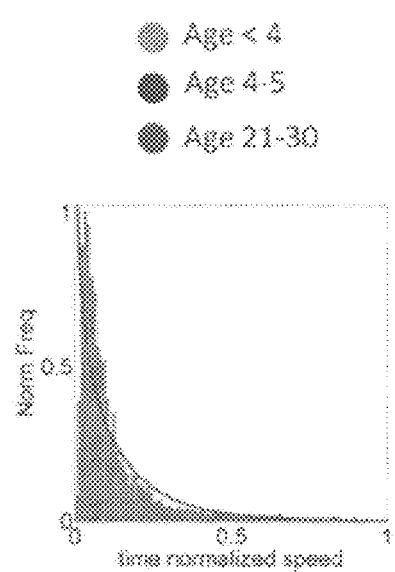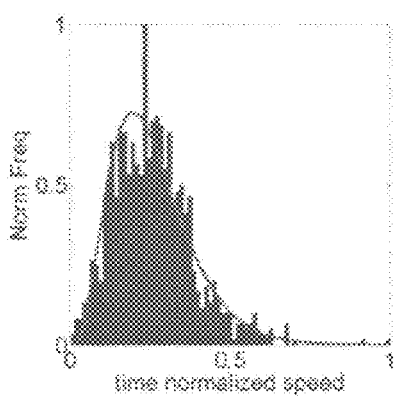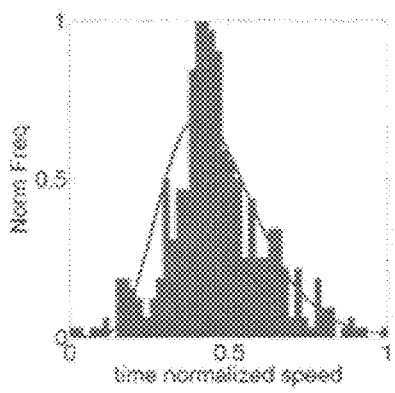
FIG. 33A
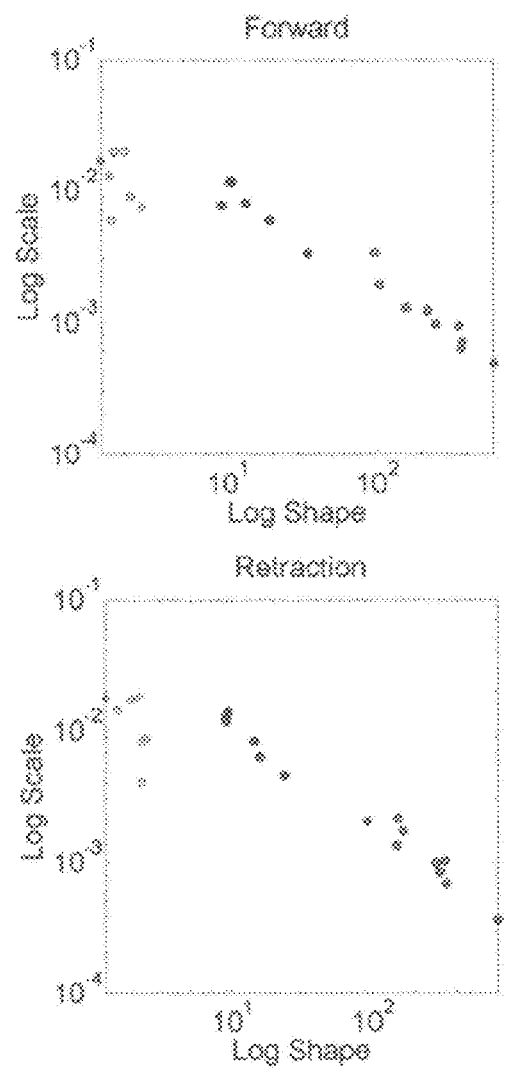
FIG. 33B
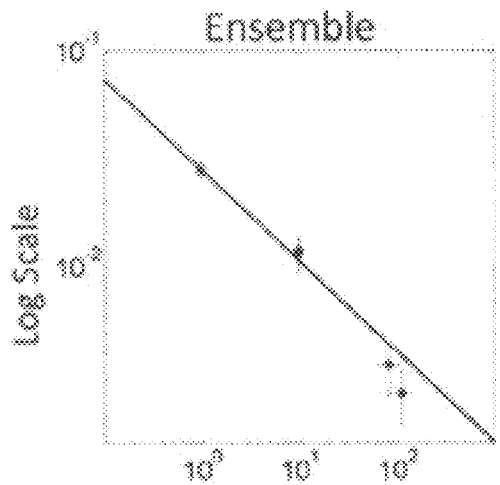
FIG. 33C

METHODS FOR THE DIAGNOSIS AND TREATMENT OF NEUROLOGICAL DISORDERS

This application is a continuation of U.S. application Ser. No. 14/354,796 filed Apr. 28, 2014 which is a 371 application of PCT/US2012/064805, filed Nov. 13, 2012, which claims priority under 35 U.S.C. § 119(e) to U.S. Provisional Patent Application No. 61/648,359, filed May 17, 2012; U.S. Provisional Patent Application No. 61/581,953, filed Dec. 30, 2011; and U.S. Provisional Patent Application No. 61/558,957, filed Nov. 11, 2011. The foregoing applications are incorporated by reference herein.

This invention was made with government support under 0941587 awarded by the National Science Foundation. The government has certain rights in the invention.

FIELD OF THE INVENTION

The present invention relates generally to neurodevelopmental and neurodegenerative disorders, particularly autism spectrum disorders, and methods of diagnosis and treatment.

BACKGROUND OF THE INVENTION

Several publications and patent documents are cited throughout the specification in order to describe the state of the art to which this invention pertains. Each of these citations is incorporated herein by reference as though set forth in full.

Present advancements in genetic and epigenetic research highlight different sub-types in the autism spectrum disorders (ASD) of both known and unknown etiological origins. These new developments pose at least two fundamental challenges: 1) how to distinguish different types of autism objectively, and 2) how to treat different types of autism differently and objectively track individual cognitive and treatment progress. Current methods are ineffective at addressing these two objectives.

SUMMARY OF THE INVENTION

In accordance with the instant invention, methods for diagnosing and/or providing a prognosis for a neurological disorder such as an autism spectral disorder in a subject are provided. In a particular embodiment, the method comprises measuring the motion pattern of the subject upon interaction with an artificial agent. In a particular embodiment, the subject is not provided instruction on how to interact with the artificial agent. The artificial agent may provide a stimulus (e.g., a real-time video of the subject) when the subject contacts a region of interest (e.g., a virtual region of interest such as in 3D space). A difference in the motion pattern of the subject compared to a healthy individual and/or the presence of a motion pattern associated with a neurological disorder indicates whether that the tested subject has the neurological disorder. In certain embodiments, the artificial agent is a dynamic media or interface and may be a robot, three dimensional animate, speaker, or screen. In a particular embodiment, the artificial agent is a screen. The methods of the instant invention may further comprise measuring other aspects of the subject (e.g., facial patterns) upon interaction with external media portraying an artificial agent.

In accordance with another aspect of the instant invention, methods for determining the ability of a therapy to modulate (e.g., inhibit or treat) a neurological disorder such as an autism spectral disorder in a subject are provided. In a particular embodiment, the method comprises measuring the motion pattern of the subject upon interaction with an artificial agent, after administering the therapy (e.g., pharmaceutical based or non-pharmaceutical therapy) to the subject. In a particular embodiment, the method further comprises measuring a motion pattern of the subject prior to the administration of the therapy (e.g., as a baseline). The modulation of the motion pattern of the subject after administration of the therapy (e.g., to a normal motion pattern) indicates that the therapy modulates the autism spectral disorder.

In accordance with another aspect of the instant invention, methods of lessening the improper motion pattern of a subject with a neurological disorder such as an autism spectral disorder are provided. In certain embodiments, the method comprises having the subject interact with an artificial agent. In a particular embodiment, the artificial agent is a robot, particularly one programmed to encourage the subject to react and co-adapt with the movement patterns that the artificial agent is endowed with. These patterns can be gradually changed so as to objectively reassess the degrees of resistance or compliance of the child's somatosensory systems.

BRIEF DESCRIPTIONS OF THE DRAWING

FIG. 1 provides a schematic of a simple task to examine the ebb and flow of spontaneous and deliberate motions in closed loop with the ebb and flow of intuitive and deliberate cognition.

FIG. 2A through FIG. 2G provide speed profiles of a child with ASD and of a TD peer from a few minutes of motion tracking (forward-intended to the target and spontaneously retracting away from it). Dots mark the value of the speed maximum each trial along the Y-speed axis and the time when the maximum was attained along the X-time axis (FIG. 2A and FIG. 2B). These curves are the instantaneous magnitude of the velocity vector tangent to the hand movement trajectory from the initial position of the hand to the target-touch on the screen (labeled intended) and then away from the screen to a full stop (labeled spontaneous). Inset frequency histograms are from the time to reach the maximum speed. FIG. 2C and FIG. 2D provide the frequency histograms of the speed maximum of FIG. 2A and FIG. 2B. FIG. 2E provides a fit of all of the experimental distributions of the speed maxima to a Gamma probability function which is characterized by 2 parameters (a,b). The maximum likelihood estimates for one sample TD and one sample ASD child are shown in Gamma parameter space with confidence regions for intended reaches (FIG. 2F and FIG. 2G).

FIG. 3A through FIG. 3F show group and individual cognitive-dependent motor learning reshapes the stochastic baseline signature of the children and track performance gains individually and as a group. FIG. 3A provides baseline group classification according to the stochastic patterns of the speed maximum. FIG. 3B shows groups shifted their stochastic signatures for both movement types as a function of cognitive-dependent motor learning. FIG. 3C shows speed learning induced by higher cognitive loads during deliberate reaches intended to touch a target. FIG. 3D shows spontaneous cognitive-dependent motor learning co-occurring with the deliberate learning. FIG. 3E through FIG. 3F show individual trajectories for each child in each movement mode (3 connected points are baseline, cognitive-dependent multimodal and well-practiced unimodal again).

FIG. 4 shows the maximum velocity values for typical vs. ASD from movement trajectories that accomplish a goal have a skewed distribution that can be well characterized by the 2-parameter continuous Gamma distribution family.

FIG. 5A and FIG. 5B show confusion matrices from linear decoding algorithm using leave-one-out cross-validation with nearest neighbor criterion to blindly classify not only which martial art technique (jab, cross, hook or uppercut) a randomly chosen movement trajectory came from but also whether it was from the deliberate striking portion or from the spontaneous (retracting) transition of each technique as the limb was being passively carried along in concert with the rest of the body. Movements were being learned by novices (5 total and taught by an expert, hundreds of repeats). Upper quadrant decodes the intended strikes whereas lower quadrant decodes automatic transitions. Rows are predicted, columns are veridical. Input parameter is max speed. Notice that the TD new to martial arts do not confuse intended and automatic spontaneous transitions despite the learning process. In marked contrast with the TD cases in FIG. 5A, the movements from an ASD participant—also a novice—have lower predictive accuracy and cannot distinguish between intended and spontaneous segments of the techniques (FIG. 5B). Arrows identify levels of control from unconscious-autonomic to conscious-voluntary with a gradient of statistical patterns of movement variability that map onto functionality classes.

FIG. 6A and FIG. 6B show the differential statistical signatures of movement variability based on the maximum-likelihood estimation (MLE) of the Gamma Distribution parameters (shape and scale) that best fit the frequency distribution of peak velocities from the hand movement trajectories obtained as children learned new cognitive aspects of a familiar pointing task. Movements decomposed into intended and automatic subunits. FIG. 6A shows learning shifted the signature of variability in all three groups as the pointing movement became stable and regained the unimodal speed feature of well practiced point-to-point reaches. In Gamma phase space, TD children (6) fell far apart from children with ASD (12) in two age groups (ASDI 4-6 and ASDII 9-15 year old). Children with ASD had values towards the exponential range of the Gamma whereas TD children fell towards the Gaussian range. The distance between the parameters from the intended and automatic segments of their reach remained larger in TD than in ASD, a feature that can serve to objectively and reliably diagnose ASD across ages. FIG. 6B shows the power law describing the unfolding of each group in Gamma Distribution Parameter space (log-log plot) where 3 children in the spectrum shifted patterns closer to typical ranges when learning resumed.

FIG. 7A shows that TD children explored space and discovered without instructions a RoI (3D trajectories) as their moving hand passed through two virtual planes (that they could not see) and triggered real time videos of themselves. Hand trajectories are in the OFF region and turn the video OFF. By sustaining the hand in the RoI they can sustain the video ON. They come to this realization on their own. Inset shows the evolution of the hand distance from the origin of the coordinate frame fixed in the room. Pattern is random until they approach the end when the child makes systematic motions within the same time window used to build the "cost" of the task linked to the reward and form a policy across the space of possibly learning scenarios ranging from random to exploratory to systematic to intended and guide a gradient flow whose function will give out the task goals that the child comes to discover. The model may use Jacobi-Bellman equations and empirically derived noise. FIG. 7B shows spontaneously evoking interest in the actions of a 10 year-old child with ASD using the same real-time movement based biofeedback paradigm in closed loop with real-time video-triggering as in FIG. 7A. RoI hand points trigger the images of the child moving in real time on a computer screen facing the child at a fixed distance across sessions in different days. This evokes in the child a notion of peripersonal space and induces a notion of self-control over the video triggering. Initially mechanical, nearly noise-less and repetitive motions from the same child acquire more variability within a couple of separate sessions (FIG. 7C). FIG. 7C shows that the same low-functioning, non-verbal 10 year old child with ASD initiates exploratory behavior on its own in a matter of minutes within a different session from that of FIG. 7B—without instructions—on its way to discovering the RoI. Notice the change in landscape for the distance-cost beginning to show systematicity in the time-interval domain.

FIG. 8A through FIG. 8K provides the three dimensional digital rendering frames from the expert's performance of one trial of J-C-H-U beginner's white belt technique using the real-time sensor outputs. Arrows mark the locations of 15 electromagnetic sensors recording at 240 Hz. Traces in the rendered figure mark the hand motions. Forward segments were away from the body and staged against an imaginary opponent. They coexisted with the incidental transitions of the other limb simultaneously moving away from the opponent. FIG. 8A: Jab1 in the forward direction, away from the body. FIG. 8B through FIG. 8D: Jab 2 back towards the body simultaneously with Cross 1 forward. FIG. 8E through FIG. 8F: Cross 2 back simultaneously with Hook 1 forward. FIG. 8G through FIG. 8J: Hook 2 back simultaneously with U1, ending the routine with both hands back to protect the face. Bottom panel, FIG. 8K, focuses on the expert's hands.

FIG. 9A through FIG. 9D show the different effects of speed changes on the incidental and deliberately staged movement trajectories with expert performance of a fluid sequential full set of techniques. FIGS. 9A and 9B: The instantaneous speed profiles from all 10 trials performed at the slow instructed speed from the left and right hands alternating between staged and incidental segments of each technique. The technique segment is indicated for each hand speed. Arrows indicate the alternating order and mark the simultaneous performance of a staged and an incidental segment. FIG. 9C: All trajectories from the staged segments of the left hand at the fast and the slow speeds grouped to show their similarity in space. FIG. 9D: Staged trajectories for the intended segments in the Cross and Hook techniques performed by the right hand also maintained the spatial properties despite instructed speeds. The return incidental trajectories from the Uppercut changed in space with the speed. Arrows indicate the flow of the motion.

FIG. 10A through FIG. 10H show the different effects of speed changes on the incidental and staged movement trajectories of a typical TC novice. The dynamics based dichotomy between intended and incidental modes of action remained despite different levels of expertise. FIG. 10A: J1 staged towards an imaginary opponent had different trajectories for slow and fast and these were similar for the incidental J2 in transition to the C1. FIG. 10B: C1 staged and intended towards the nose of an imaginary opponent has similar trajectories for slow and fast speeds, and they were also similar to those from the incidental C2 in transition to the H1. FIG. 10C: H1 staged towards the opponent had similar trajectories for slow and fast. C2 inwards towards the body also had similar trajectories despite different instructed speeds. C2 was simultaneously performed with the U1 staged against the imaginary opponent. FIG. 10D: U1 had similar trajectories despite differences in the instructed speeds. The incidental U2 was not different even though the speed was different. FIG. 10E through FIG. 10H show the corresponding speed profiles for the staged and for the incidental segments of each technique.

FIG. 11A through FIG. 11H show the similar effects of speed changes on incidental and staged trajectories in the individual with ASD. The ASD case did not manifest the dynamics-based dichotomy between intended and incidental modes of action present in the TC. FIG. 11A: J1 staged towards an imaginary opponent had different trajectories for slow and fast and these were similar for the incidental J2 in transition to the C1. FIG. 11B: C1 staged and intended towards the nose of an imaginary opponent has similar trajectories for slow and fast speeds, and they were also similar to those from the incidental C2 in transition to the H1. FIG. 11C: H1 staged towards the opponent had similar trajectories for slow and fast. C2 inwards towards the body also had similar trajectories despite different instructed speeds. C2 was simultaneously performed with the U1 staged against the imaginary opponent. FIG. 11D: U1 had similar trajectories despite differences in the instructed speeds. The incidental U2 was not different even though the speed was different. FIG. 11E through FIG. 11H show the corresponding speed profiles for the staged and for the incidental segments of each technique.

FIG. 12A through FIG. 12D show that the intended and automatic modes of control are indistinguishable in ASD case. FIG. 12A: The prediction of control mode (movement class) from 6 participants (5 novices and the expert) is accurate for both the technique and movement type. FIG. 12B: Worst individual performance (well above chance, ⅛ from 4 techniques and 2 movement types) still does not confuse the two movement types at all. Rows are actual values while columns are assigned values from the leave-one-out cross-validation. FIG. 12C: ASD case performs at a comparable level to the novices for predicting each individual technique but the goal-directed segments of the techniques are generally confused with the supplemental segments when using the maximum curvature from the hand trajectories as input to the linear classifier. FIG. 12D: The predictive accuracy of the classifier drops for each technique and the goal-directed vs. spontaneous supplemental movements are indistinguishable when using the maximum speed as input to the classifier.

FIG. 13A through FIG. 13D show the different statistical signatures of motor variability between TC and the ASD case. FIG. 13A: Histogram of peak velocity values across all sessions in typical novice (sibling) was well fitted by a Gamma distribution (maximum likelihood estimates (m.l.e.), shape 10.09 scale 0.2 with 95% confidence regions [7.43 13.68] and [0.15 0.28] respectively; mean 2.1 m/s, variance 0.43). FIG. 13B: The peak velocity values in the ASD case distributed differently (364 trials see text for bin size determination). Histogram across sessions and techniques yielded a Gamma fit towards the exponential range with m.l.e. shape 1.03, scale 1.87 with 95% confidence regions [0.91 1.18] and [1.59 2.20] respectively. FIG. 13C: A m.l.e. Gamma fit to each individual participant plotted in Gamma parameter space shows a spectrum of value. A power fit curve using model $f(x)=ax^b$ with values a=1.93, b=−0.79 and 95% confidence intervals [1.72, 2.15], [−0.89, −0.69] respectively, 12 df. Goodness of fit: rms 0.09, rsquare 0.96 (using the Levenberg-Marquardt algorithm). FIG. 13D: Linear model fit to the log-log of the Gamma parameter fit with $f(x)=p_1 x+p_2$ with $p_1=-1.01$, $p_2=1.00$ with 95% confidence intervals [−1.19, −0.82] and [0.52, 1.48] respectively, 12 df. Goodness of fit: rmse 0.2, R-square 0.92 (using QR-factorization-solve).

FIG. 14A through FIG. 14C provide graphs regarding the cognitive-dependent motor learing in TD and in ASD. FIG. 14A shows a significant increase in choice-accuracy ($\chi^2=30.8$, $p<10^{-7}$) and reduction in cognitive decision-time (CDT) ($\chi^2=44.8$, $p<10^{-9}$) across groups with paralleled motor learning. FIG. 14B shows the stochastic-signatures shifted with learning as shown in the Gamma-plane. R-square=0.978, rmse=0.001 (multimodal, dashed line) and R-square=0.957, rms=0.003 (unimodal, continuous line). FIG. 14C shows each child's learning progression is different as shown by the individual trajectories connecting the Gamma-parameters from the baseline to the multimodal cognitive-dependent learning to the well-practiced-unimodal speed profiles.

FIG. 15A through FIG. 15B provides example movement decision trajectories. FIG. 15A provides hand trajectories from a single session lasting several minutes. Inset shows an example match-to-sample trajectory requiring a decision-making process that starts with a touch at the start button in the bottom center of the touch screen and ends with a touch at the correct match, then a retracting unintended trajectory on its way to another trial. FIG. 15B provides an example speed profiles from the touch of the start to the touch at the correct match (target). Arrows mark the length of the response time in seconds.

FIG. 16A and FIG. 16B provide normalized frequency distributions of response time (s) for girls and boys in each group. FIG. 16A provides skewed distributions for the girls. Data pooled across all 3 experimental conditions (color, shape, rotation) for TD, ASDI, and ASDII, well-fit by the Gamma probability distribution (712 trials TD, 511 trials ASD1, 616 trials ASDII). FIG. 16B provides the same for the boys in each group (912 trials TD, 680 trials ASD1, 1060 trials ASDII).

FIG. 17A through FIG. 17F provide a DT comparison between girls and boys for each experimental group (TD, ASDI, ASDII). FIG. 17A provides box plots from the nonparametric ANOVA, Kruskal-Wallis test showing no significant differences between the performance of the TD girls and TD boys. In the ASDI group, girls had faster DT than boys (FIG. 17B). The ASDII group showed the largest effects of gender on the DT parameter (FIG. 17C). The m.l.e. parameters of the Gamma for each of the gender-groups pooling all trials across all three experimental conditions are plotted in the Gamma plane (FIG. 17D). The 95% confidence error bars are plotted for each point for the shape and scale parameters. Unfolding the TD group's pooled data into individual points reveals a scatter with no discernible clusters between girls and boys, consistent with the lack of statistical separation according to the non-parametric ANOVA (FIG. 17E). Unfolding the girls and boys of the ASD groups revealed differences in the Gamma plane between ASDI (blue group) and ASDII (FIG. 17F).

FIG. 18A through FIG. 18F shows the breakdown of the pooled data into the experimental conditions (color, shape, rotation) to examine the effects of group type (TD, ASDI, ASDII) for each experimental condition. FIG. 18A through FIG. 18C: Consistent effects of group type (TD, ASDI, ASDII) for each condition are shown in the form of box plots from the non-parametric ANOVA, Kruskal-Wallis test. FIG. 18D through FIG. 18F: The Gamma plane analyses for each experimental condition showing that color accounts for the separation between boys and girls in ASDI, whereas shapes accounts for the separation between boys and girls in ASDII reported in the pooled data. The 95% confidence error bars are also plotted.

FIG. 19A and FIG. 19B shows the scaling effect. FIG. 19A shows the frequency distributions of the logarithm of the DT (ms) (number of trials pooled across each child-type group were TD 1,624, ASDI 1,191, ASDII 1,676). FIG. 19B shows the m.l.e. of the Gamma shape and scale parameters of the logarithm of the DT (ms) from each child-type-gender group lined up on the Gamma plane with a tight fit.

FIG. 20A through FIG. 20C shows self-emerging statistical subtypes for TD and ASD cohorts as a function of age and intellectual abilities. FIG. 20A provide normalized frequency distributions from each self-emerging cluster in FIG. 20B of the time-normalized path length that the hand traverses on its way to touch the target (forward reach) and away from the target (spontaneous retraction). FIG. 20B provides scatter of points, where each point represents a participant uniquely labeled by the (a-shape, b-scale) parameters on the Gamma plane. Bottom panels zoom in the scatters from the stochastic signatures of the time normalized path length from intended and unintended hand movements. FIG. 20C provides the stochastic signatures of each self-emerging cluster are well characterized by a power relation fit through six points (intended and spontaneous for each self-emerging TD group).

FIG. 21A through FIG. 21F shows the cognitive-dependent somatosensory motor-learning, and somatosensory motor-dependent cognitive improvements objectively tracked in TD and in ASD cohorts. FIG. 21A shows changes in the cognitive load of the task initially evoked multiple peaks in the speed profiles of the hand motions intended to the target, yet unimodality returned within minutes of practice (shown here for the same pre-school TD participant). The stabilization also manifested in the spontaneous learning of the retracting segments (FIG. 21B). FIG. 21C provides a log-log plot of trajectories of the rate of change in the stochastic signatures of the forward hand motions in each self-emergent statistical subtype. FIG. 21D shows the shifts in the stochastic signatures that were also tracked in the spontaneous retractions of the hand motions that were not explicitly instructed or directed to any goal. FIG. 21E shows that the ensemble data shows greater shifts for the older non-verbal ASD groups. With movement practice, the decision making latencies (shown in seconds) significantly decreased across clusters when comparing the 150 later to the 150 earlier trials of each session (FIG. 21F).

FIG. 22 shows the hand trajectories from forward reaches and corresponding speed profiles. Black dots mark the target locations presented by the robot. The black arrow marks the direction of the reach from the starting point to the external targets. Speed profiles show the bradykinesia of parkinsonian motions with double the movement duration.

FIG. 23 shows the end point accuracy. End point errors are based on Euclidean norm from the forward reaches. Solid-line squares mark the reduction for PD patient in end point variability during the Finger Vision condition. Dashed-line square shows that there was also a reduction in the end point variability during the Target Vision condition, but not as much as with visual feedback from the moving finger. Black dots mark the target position presented by the robot.

FIG. 24 shows the area-perimeter ratios. Normal controls conserved the distributions of the area and perimeter ratios around ½, as well as their covariations, despite changes in the form of sensory guidance, which induced scaling in the reaching speed. This conservation was manifested in normal controls for both the forward and the back reaches. Parkinson's patients broke the symmetry but restored the covariation of the ratios for both the forward and backward reaches when continuous visual feedback of the moving finger was provided.

FIG. 25 shows the hand trajectories from the reaches back to the initial posture and corresponding speed profiles. The black arrow marks the retracting direction of the motion from the targets back to the initial posture. Corresponding speed profiles from reaching back to the initial posture are shown. In both the NCs and the patients with PD, the form of sensory guidance exerted a significant effect on the values of the peak velocity, as shown in the insets from the ANOVA.

FIG. 26A and FIG. 26B show automated-to-voluntary (task incidental/task relevant) ratios across 25% segments of the forward movement trajectories. The line of unity indicates equally balanced task-incidental and task-relevant degrees of freedom. FIG. 26A shows forward motions compared between PD patients and normal controls for each type of visual guidance. FIG. 26B shows the retracting movements.

FIG. 27A through FIG. 27C show the effects of priming on the movement trajectories at the wrist in typical NC participant using two different levels of speeds randomly cued.

FIG. 27A shows DEFAULT forward motion trajectories with corresponding speed profiles for slow and fast cases. Inset shows the actual stimuli on the screen priming the subject to match the orientation of the rod on the screen (vertical in this case) with the hand-held rod. Top are the forward paths and bottom are the retracting motions. FIG. 27B shows the Primed-UP cases evoked similar final orientations as the DEFAULT condition. The inset shows the priming cup with handle next to the original rod. This figure is made from the right hand data and right hand stimuli for a right-handed person. FIG. 27C shows the primed-DOWN condition changed the trajectories in both the forward and retracting cases. The inset shows the priming condition where the arm and hand underwent complex rotations. The instruction was to match the orientation of the rod on the screen as if the hand were to gasp the handle of the cup to drink from it.

FIG. 28A through FIG. 28C show the effects of priming on the movement trajectories at the wrist in typical patient within PD2 group using two different levels of speeds randomly cued. FIG. 28A, FIG. 28B, and FIG. 28C correspond to FIG. 27A, FIG. 27B, and FIG. 27C.

FIG. 29A, FIG. 29B, and FIG. 29C correspond to FIG. 27A, FIG. 27B, and FIG. 27C.

Figure 30A:
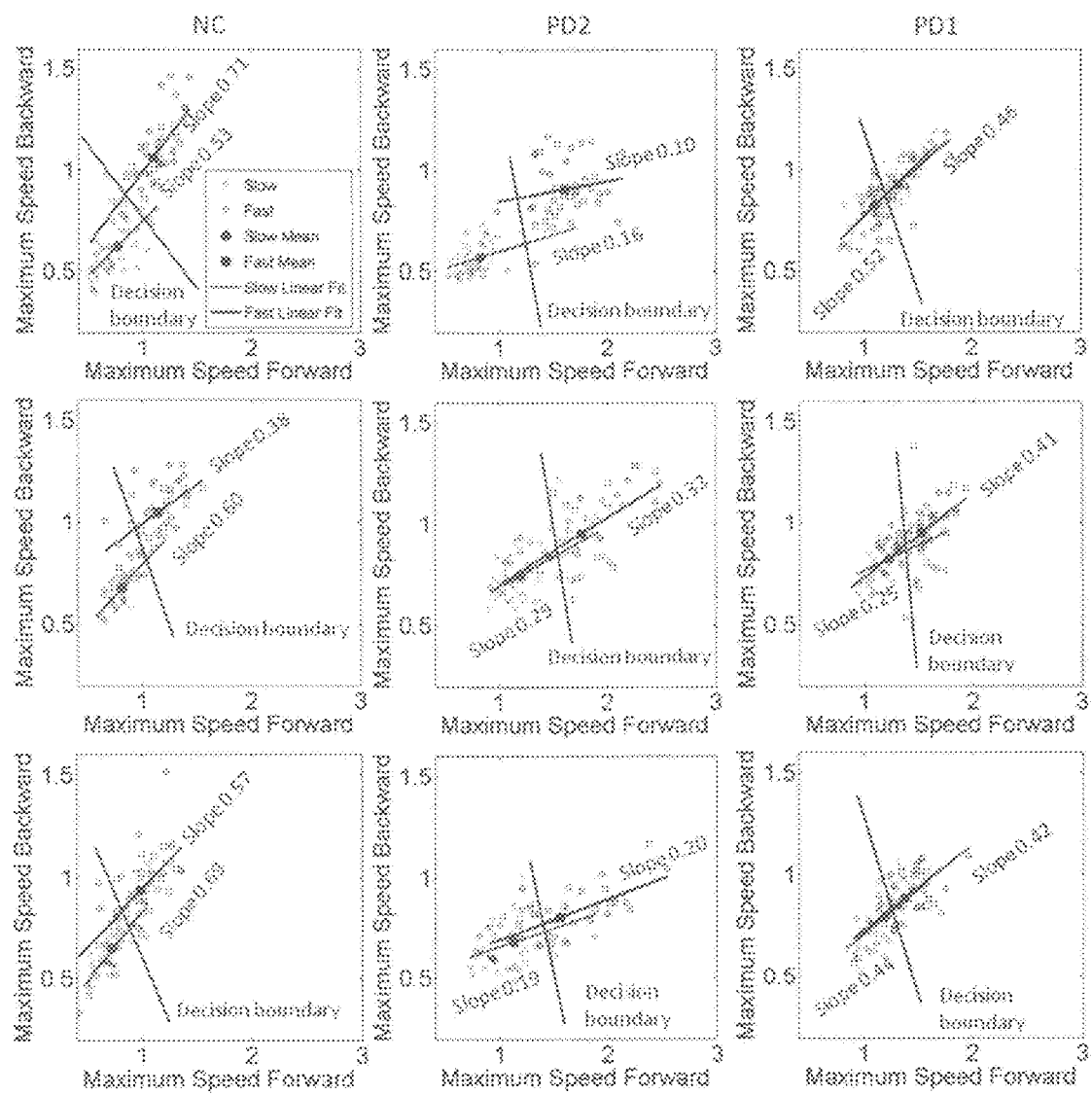
Figure 30B:
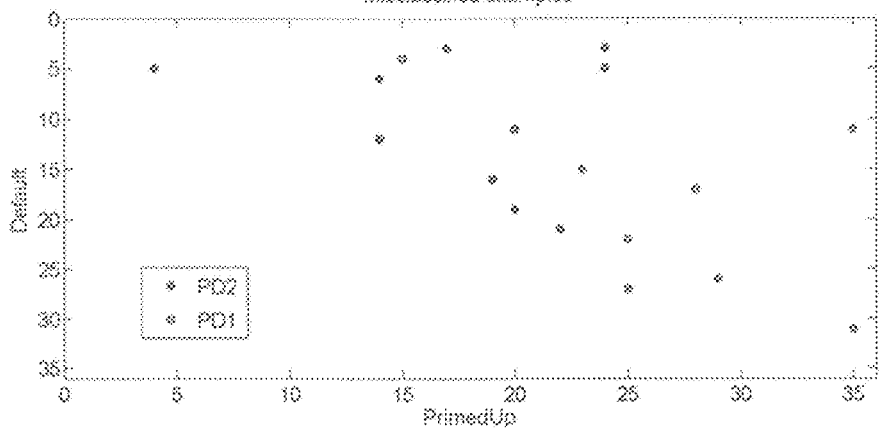

FIG. 30A and FIG. 30B show self-emerging clusters and patient subtypes based on speed maxima (m/s). FIG. 30A provides representative NC and patients from PD1 and PD2 subgroups grouped the speed maxima differently in the forward and retracting motions as a function of cognitive load condition. FIG. 30B shows self-emerging subtypes of misclassified trials from the blind clustering k-means separated exactly as the p-value statistics had predicted.

Figure 31A:
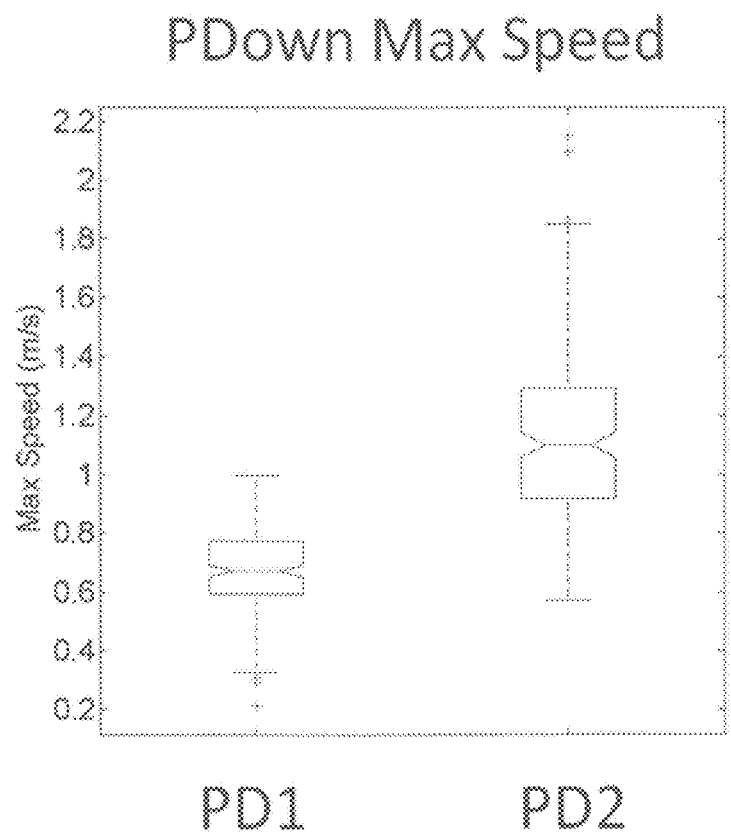
Figure 31B:
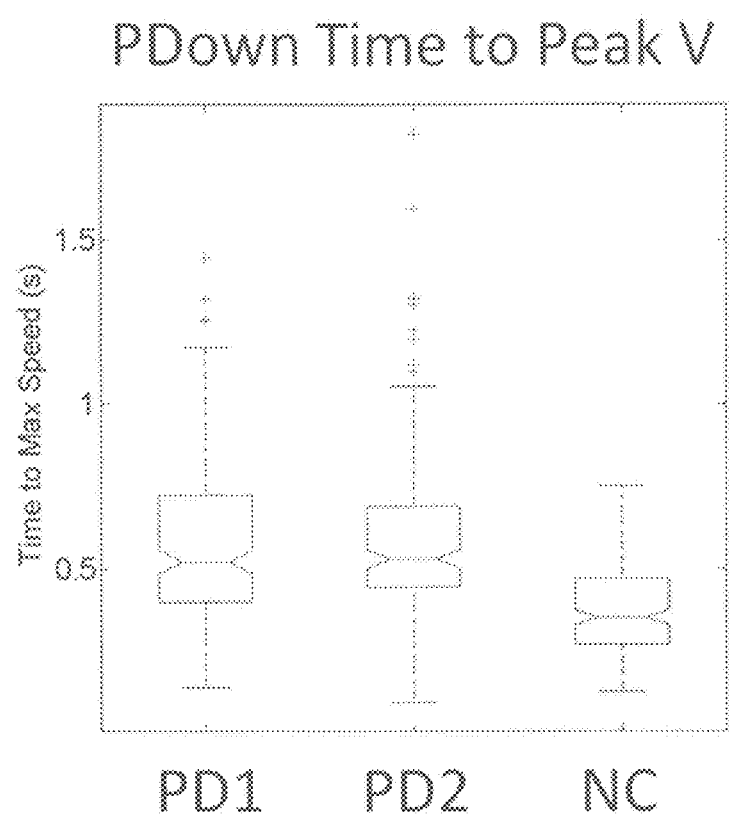

FIG. 31A and FIG. 31B show the effects of increasing task difficulty on the speed and timing of the reach by priming the final desired orientation such as to evoke complex mental rotation of the stimulus. FIG. 31A shows PD1 patients moved significantly slower than PD2 patients according to the values of the hand's maximum speed returning from the target to the resting position. FIG. 31B shows the timing of the maximum speed was not significantly different in the two patient groups but both groups took longer to reach the velocity peak than NC's did.

Figures 32A, 32B:
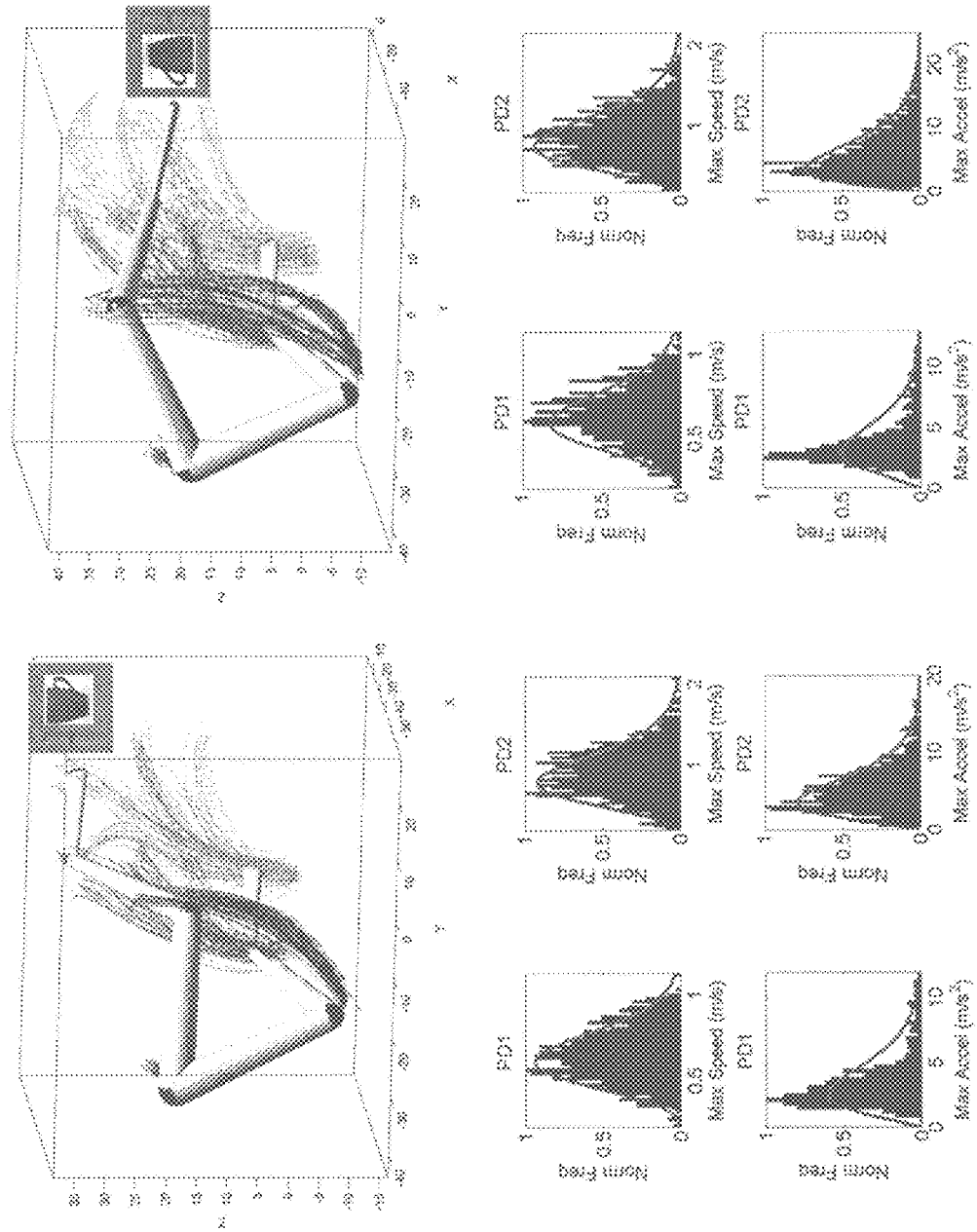

FIG. 32A and FIG. 32B show normalized frequency distribution of the maximum speed and maximum acceleration values from the retracting primed motions in two groups of patients with PD. FIG. 32 A and FIG. 32B provide arm trajectories (shoulder, elbow, wrist, and hand) during the primed-UP condition similar to the DEFAULT case. The initial and final arm postures corresponding to the trajectories towards two randomly selected positions are superimposed.

FIG. 33A through FIG. 33C show self-emerging statistical subtypes across ages and school level. FIG. 33A: Normalized frequency distributions from each self-emerging cluster in FIG. 33B of the time-normalized path length that the hand traverses on its way to touch the target (forward reach) and away from the target (spontaneous retraction). Each distribution is comprised of several thousand trials.

FIG. 33B: Scatter of points, where each point represents a participant uniquely labeled by the MLE of (a shape, b scale) parameters on the Gamma plane. FIG. 33C: The stochastic signatures of each self-emerging cluster are well characterized by a power relation fit through six points (intended and unintended). The power relation spans several orders of magnitude on both axes.

Figure 34B:
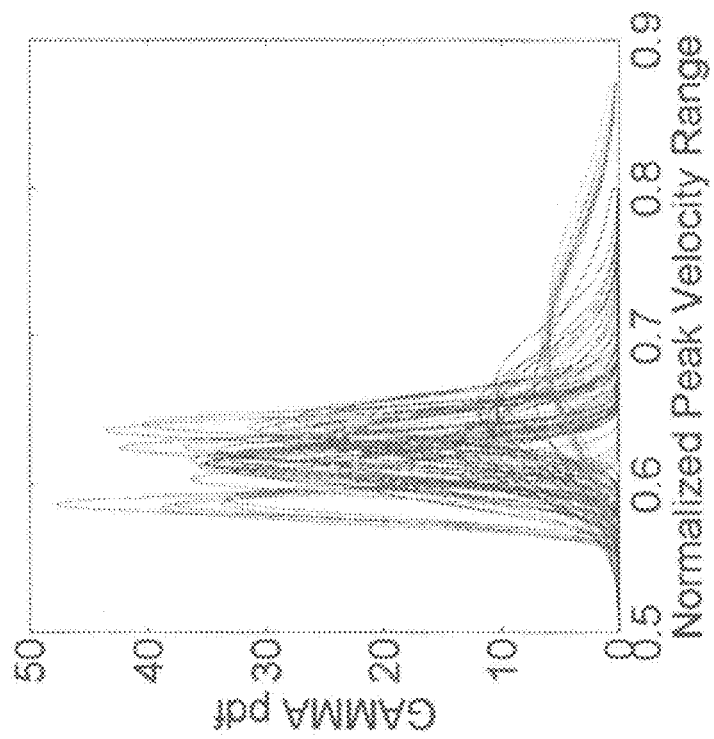
Figure 34A:
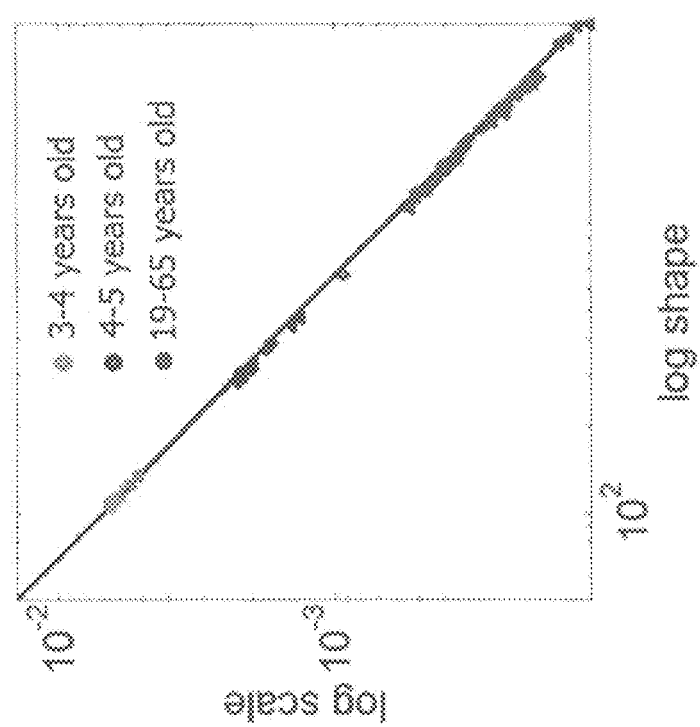

FIG. 34A and FIG. 34B show the scaling power law characterizes the human somatosensory-motor percept across ages. FIG. 34A: Exponential relation between the MLE of shape and scale Gamma parameters fitting the empirical frequency distributions of the normalized peak velocity. The linear fit through the log-log transformed parameters shows a scaling relation whereby each age group self clusters along the line. FIG. 34B: Gamma probability density function for each participant computed using the MLE shape and scale parameters from the empirical range of the normalized peak velocity.

DETAILED DESCRIPTION OF THE INVENTION

Movement abnormalities are not a core symptom of autism spectrum disorders (ASD), yet movement is implicitly present in each of the symptoms currently defining the disorder. Movements provide a new tool to assess ASD and to track cognitive and behavioral changes because the same brain that controls cognitive processes controls body movements. Cognition and movement coexist in a closed loop where one component impacts the other. There are two main types of cognitive processes: deliberate-conscious and automatic-unconscious (Gazzaniga, M. S., The Cognitive Neurosciences. 4th Ed., (MIT Press, 2009)). Current methods in cognitive psychology cannot access the unconscious mental processes because they rely on inferences and verbal reports about mental operations and perceptions that reach consciousness.

It has been discovered herein that movements also come in these two flavors. Some movements are deliberate, generally aimed at a goal and consciously controlled. Deliberate movements stand in contrast to spontaneous movements. Spontaneous movements are automatically carried along by the body in transition to other goal-directed movements and tend to be largely below conscious awareness. They do not permeate with the same level of intentionality or goal-directness as deliberate movements. The trajectories of spontaneous movements change as a function of the speed whereas those of deliberate movements keep their intended course despite speed changes. In natural motions—whether instrumental activities of daily living or complex choreographic sequences—the ebb and flow of these two movement classes can be unambiguously identified with the random fluctuations of movement parameters and connected with the ebb and flow of mental processes. Unlike automatic cognitive processes that cannot be reported on, spontaneous movements that also occur largely below conscious awareness can be precisely and objectively quantified, independent of any inferences. They also provide a new tool to connect body movements and cognitive abilities. The random fluctuations of trajectory parameters during deliberate and automatic pointing movements—such as the hand speed maximum and the time to attain the speed maximum—give away unequivocal differences between those with neurodevelopmental and neurodegenerative disorders (e.g., individuals with ASD) and their typically developing (TD) peers, optionally in the naturalistic settings of their classroom environment.

The dichotomy between deliberate and spontaneous motions is new, yet it is present in cognitive processes, body gestures for communication, biological motions, facial expressions, ON/OFF states of saccadic eye movements, speech, etc. Most likely the core automatic centers of the brain control the spontaneous motions (e.g., the cerebellum, basal ganglia and limbic system). These centers are severely disrupted during development in ASD. In certain individuals, they may not mature and give rise to the goal-directness necessary to leave the autistic bubble and explore the peripersonal space, much less the social medium. However, it is possible to tap into mental processes that are below conscious awareness and objectively measure the behavioral outcome in the unconscious movements.

In cognitive psychology and cognitive neuroscience there are two separate cognitive systems—those that control automatic processes and those that control more deliberate ones. The two classes of movement can connect with these two cognitive categories—automatic and deliberate. When cognitive processes and movement mechanisms are studied in a close loop such that cognition impacts movement and movement impacts cognition, one can be influenced by reshaping the other. So one can make automatic cognitive processes impact spontaneous motions and deliberate cognitive processes impact deliberate motions. In the case of low-functioning non-verbal children with ASD one can very precisely and objectively track their spontaneous learning with no instructions or specific goals.

Herein, cognition and movement have been connected and this connection has been made objectively quantifiable. These objective measurements may be performed in about 15 minutes, with minimal disruption of daily routines. Notably, the task, the stimuli, the medication, etc. can be changed and the outcome very precisely measured before and after the manipulation to assess performance gains. Each child has different sensory preferences and capabilities, and different predispositions to learn. These can be measured and personalized target therapies may be identified and tailored according to the neurodevelopmental and neurodegenerative disorder or ASD type. Accordingly, the instant invention has provided an entirely objective metric of behavioral performance that is simple to use, fast to acquire, and mathematically sound.

While the instant invention has mostly been exemplified with ASD, the methods can be used with other developmental/mental disabilities (e.g., attention deficit hyperactivity disorder (ADHD), Parkinson's Disease, stroke (e.g., stroke in the cortex, particularly the posterior parietal cortex; Torres et al. (2010) J. Neurophysiol, 104:2375-2388), Down syndrome, William syndrome, schizophrenics, etc.). The instant methods may also be used with other developmental disabilities to identify traits solely associated with ASD with clearly localized regions of the Gamma-plane in relation to other disorders that also impact mental capabilities. Stochastic rates of change and rules may be identified that are specific to ASD.

In a particular embodiment of the instant invention, real-time hand movements are captured from the subject (e.g., child) as he/she faces an interface (e.g. a computer monitor) and are used to trigger real-time videos (e.g., videos of self from a camera facing the subject, pre-recorded cartoon videos of the subject's preference, or the like). The videos are triggered by the subject's real-time motions of his/her hand when the motions are constrained to a virtual region of interest (vROI) defined by the experimenter. In a particular embodiment, the subject discovers this vROI on his/her own, without instructions. The self discovery of the vROI emerges by random exploratory motions of the hand. Once the subject discovers the motion/vROI that triggers the videos, they systematically initiate motions that will sustain the video ON or that will flicker the videos successively ON/OFF. Typically developing subjects (TD) verbally communicate the succession of events to the experimenter. They undergo an "aha!" moment that they tend to want to explain to the experimenter. In the cases of the subject with autism spectrum disorders, the progression is different because they have various degrees of functionality that range from very low-functioning non verbal to high-functioning verbal abilities. However, they manifest changes in their motion patterns and facial expressions which are objectively quantified. These indicate substantial changes in engagement with the task and reveal the progression of the task. Their motions reveal how to attain the goal of reaching the specific vROI in space in order to attain their reward (e.g., videos of themselves or pre-recorded cartoons of their preference). Without instructions, they can then proceed to control the flow of the video display as a function of the reshaping of their personal stochastic signatures of movement variability (the random fluctuations in the movement patterns that are characteristic to each individual subject). The metrics reveal which form of reward is most effective in the sense of engaging the subject in the active exploration of the environment and exiting for a moment their "autistic bubble". Sessions typically last a few minutes and enable measurement behavior before and after this exploratory exercise.

In a particular embodiment, the method of the instant invention is a real-time co-adaptive interface between the subject and an artificial agent (e.g., a robot, three dimensional animate (e.g., avatar), screen, or any dynamics media with controllable dynamics). As above, there may be no explicit instructions or goals given to the subject. The user rather may discover the goal through random behavior that leads to active exploration of its surroundings stimulated by a reward (some change in the external stimulus). Once the exploration turns systematic, the subject can discover that it can act in tandem with the media's dynamics and control it. This sensory-feedback based control in closed loop with the external media (agent) can then be used to co-adapt the agent's and the user's motions, emotions, etc. The external media with dynamics can be a robot, a virtual three dimensional animate, sound (speech) or any kind of simpler sensory input that changes over time with some structure (i.e., that has dynamics).

As stated hereinabove, this methodology may lack instructions or well defined goals. Unlike other methods that also exploit sensory-motor feedback in closed loop (e.g. the Wii®, brain machine interfaces, etc.) the instant methodology does not require the subject to understand a priori what the goal of the task should be. The subject comes to realize the goal by randomly interacting with the environment and discovering the contingencies that evoke a rewarding experience. Since methods have been developed that can objectively quantify the subject's sensory preferences in the stochastic patterns of his motions, one can identify in real time which reward is the most effective in engaging the subject and fostering systematic exploratory behavior that potentially can lead to active control of the stimulus in closed loop. Once the active control of the stimulus is attained, one can co-adapt the motions of the subject and those of the stimulus in real time. This means that one can reshape the motions of the subject by reshaping the stimulus motions. One can reshape the stimulus motions in ways that can shift the stochastic signatures of the autistic subject towards typical patterns that are acceptable within social settings without having to explicitly tell the subject. Since the random fluctuations of velocity-dependent parameters are a readout of the subject's somatosensation, it is possible to very precisely quantify if there is resistance or compliance to co-adaptation under specific types of noise that the external media can be endowed with. In other words, a form of augmented sensory feedback has been created that can be precisely parameterized and its effectiveness tracked in real time.

The stimulus, which may be real time self videos or videos of the subject's preference, can be replaced by other media (e.g., audio, touch-vibration-type stimuli, etc.) including an anthropomorphic robot that the motions of the subject can control in closed loop with the motions of the robot. The stimulus can also be an animated three dimensional animate embedded in a social environment so one can co-adapt the subject and the three dimensional animate within a social setting to build and to foster theory of mind.

As stated hereinabove, the methods of the instant invention may be performed with a robot or robotic interface. Robots provide an amenable platform to teach the subject because they can not only move autonomously but respond to the subject's movements as well. Robots can detect different motion patterns in different subject populations and be trained to move with specific statistical signatures of variability that may be more appropriate for one population than for other.

Whether one moves with a specific purpose or mindlessly moves in "auto-pilot" mode, movement has inherent variability that is objectively quantifiable. All things being equal, the statistical signature of movement variability is unique to each person and is revealing of mental states and of mental illnesses. In this sense movement variability can become the bridge to connect the mind and the body and to provide appropriate means to improve social awareness.

The movement sense (kinesthesis) as other senses (vision, audition, vestibular input, etc.) is a form of sensory input that shapes the path of everything that one learns, yet movement can also channel out through its inherent noise- and variability-patterns the most adequate form of sensory guidance to aid the system to learn to heal itself. Such motor-sensorial preferences can be extracted and exploited in a reward-reinforcement-based cooperative person-robot setting to help stimulate creative and abstract thinking through hands-on co-adaptive interactions, parts of which can occur without full awareness and without explicit instructions.

The same research program was carried out with children in the spectrum of both genders from 4-15 years of age. These children also became engaged in the closed-loop video-triggering guided by the feedback from their hand movement in real time, yet their progression towards intentionality was slower than that of their TD peers and had a reversed progression. TD exploration transitioned from random to systematic to well-structured to intended-some TD children even verbalized the contingency of arm movement and video appearance. In marked contrast ASD started abnormally systematic (mechanic) and nearly noiseless, transitioned through chaotic phases with no discernible patterns and in some cases started to acquire similar exploratory features of the TD. In the TD children these included detectable systematic fluctuations in the distance traveled by the hand as the hand crossed the virtual planes with corresponding changes in the speed profiles of the hand which switched the statistical patterns of variability of the hand peak velocity from exponential to skewed log-normal and eventually to bimodal distributions signaling speeds from two complementary space regions.

In both TD and ASD this progression strongly depended on the child's favorite form of sensory input. In some cases the real time video of themselves was quite effective in ASD whereas for other children with ASD it was not as engaging. However, the children with ASD can do the task without instructions, even low-functioning, non-verbal. There is also a form of sensory guidance that is quite effective in engaging them in exploratory behavior towards intentional acts which can be objectively measured in their spontaneous motions. Additionally the child with ASD with echolalia and the verbal child with AS in the group were extremely engaged and did show remarkable changes in a matter of seconds across multiple sessions. The beneficial effects of this training tool were strong, fast (a few minutes a day) and consistent across all the TD children but they also showed promise in the children with ASD.

Since the children can be engaged in active exploration until they discover that they control an external stimulus and pursue that control, the real time self video can be replaced with a robot (e.g., NAO robot) that can be modified and endowed with the statistical range of movement variability from the typical children. This robot will co-adapt its movements with those of the child, initially recruited by the child. In time, once the robot detects systematicity and that it is being controlled by the child, it will be programmed to gradually shift the spontaneous components of the motions into slightly different statistical patterns until the child catches up with it and spontaneously reverts to try and control the robot. The interface may be designed in closed loop as a game to make it attractive to the child and to store the adaptation trajectory for later to be used as reference when comparing it to the trajectory of the children with ASD.

The motion detection algorithms may be developed to program the robot to detect differences between random patterns, chaotic patterns, systematic patterns, well structured patterns and intended patterns towards an emerging, well defined goal.

This interface may present snips from real social situations and may be used to probe the TD children, for problem solving in a virtual social setting and to enhance various aspects of ToM. Well established paradigms may be used that probe the young children's abilities for pretend-play, deception, implicit false belief, understanding intention, and word-learning. The statistics of both the intended and spontaneous motions that have been harvested and parameterized in natural settings may be used to introduce as the seed and then slowly reshaped in the virtual settings in order to broaden the range of patterns present in the child's behavior as the child co-adapts with the robot. In this way, awareness of automatic body motions during problem solving in the TD children is increased, which largely contribute to the highly automatic inferences in ToM. Since metrics of performance gains have been developed and tested across multiple populations of human and non-human primates, gains in behavioral performance as the child learns can be objectively quantified. This allows for the design of a tool/device to precisely quantify the form of "automatic intelligence" and identify it with automatic behavior. The instant invention may also be used to enhance awareness in TD young children of the cognitive difficulties in others to avoid bullying situations and to foster understanding of others.

Understanding and objectively measuring movements link body and brain. Building this link computationally will be fundamental to foster proper development of the subject's mental abilities in society. The instant approach to movement control and embodied cognition facilitates the objective quantification of behaviors in naturalistic settings—such as the classroom environment and the home settings—and permits the objectively quantitative tracking of movement performance and cognitive-based motor learning gains over time. Since the subject with ASD have social impairments, a framework that spontaneously—without instructions—engages them with virtual agents may first be developed. Subsequently, the actual robots may be introduced to encourage the children's active exploration and initial control over the robots, only to have the robots gradually shift the statistical signatures of variability in the subject with ASD towards typical ranges.

Since the statistical signatures are so far apart in TD and ASD, any robot can be easily programmed to use the natural statistics of movement to distinguish when it is interacting with a TD child from when it is interacting with a child that has ASD. Furthermore, since typical movements can be unambiguously classified into spontaneous and intended based on the effects of dynamics on their trajectories; but since this distinction is blurred in ASD, it will be feasible for a robot to detect motions from each child type and be programmed to respond in compliance. These natural statistical features of physical movements may be exploited to co-adapt robot and child as they interact using the appropriate noise and variability levels and to automatically (without the child's awareness) shift motor variability towards levels that promote facial expressions, body gestures and body language for non-verbal communication thus boosting social interactions. This can be achieved in closed loop using real time movements captured by motion sensors that are paired with other sensory input of the child's preference. Three novel characteristics of the new paradigm include, without limitation: (1) The automatic components of the wholesome movement unit, of which the child has no awareness are targeted—rather than restricting to the study of the intended, goal-directed component; (2) A goal is not specified. Rather, the child discovers the goal of the task through exploration; and (3) The statistics of facial expressions, emotions and body movements (intended and automatic) of both TD children and children with ASD have been parameterized (thereby providing ground truth for training the robots).

The instant methods help blend TD children with peers who have ASD. In the school system the methods will raise awareness and understanding in the TD children of the motor/communication problems in ASD and promote their willingness to approach their peers socially and to interact with them and, crucially, to avoid bullying in general. In turn by measuring and gradually shifting the statistical signatures of movement variability in ASD towards TD levels, the ASD children will be better able to blend in the social scene as others will perceive them within the ranges of socially acceptable motions. Importantly the children with ASD will not have to directly imitate the motions of their TD peers through explicit instructions. They will not be instructed to intentionally do anything. Rather their automatic behaviors will be used and the statistical patterns of their spontaneous movements will be reshaped without their awareness to evoke the transition towards intended behavior related to stimuli of their preference. These children's interactions will contribute to the improvement of their social and communicative skills in the classroom settings and beyond while circumventing the known problems that children with ASD have regarding imitation, verbal communication and cognitive understanding in general.

A mobile child-machine interface system has been developed that enables one to visit the classroom settings and have TD children interact with touch screens and perform cognitive-driven tasks adapted from their curricula. The statistical patterns of natural movements—both voluntary and automatic—were first collected across a variety of natural tasks including those of the classroom settings involving the hands and upper body and others engaging all limbs, the trunk and the head in sports routines such as beginners martial arts. All of the data was first parameterized and may be used as a source to train the robots move naturally in order to facilitate engagement with the children. Unconstrained, natural movements are recorded by the system as the child learns to perfect the task and becomes familiar with the computer environment as a whole. The initial version of this interface was in open loop. Children responded to stimuli presented on the touch screen and pointed at the correct target that matched a given sample evoked by their touch of the screen. The stimuli had perceptual and cognitive features that varied in increasing levels of complexity from purely visual (e.g., color) to more abstract (e.g., geometric shapes) and even yet to more complex features that required mental rotation to correctly match the given sample. The movements of the hand, arm, trunk and head were concurrently recorded with the hand-screen touches and video input from a camera facing the child, with all behavioral events time stamped and logged for further off-line analyses. Movements of the hand homing in on the target and immediately preceding touching the screen were intended towards the target or towards the sample to be matched. These intended movements touched those locations on the screen. Spontaneously retracting motions were automatic in that they were transitional, did not pursue a goal, were not instructed and merely supported the goal-directed component of the whole reach. These motions were being carried passively along as the body spontaneously recovered from the goal-directed portion. They engaged the full body and were very revealing of the dynamics of the task. Their hand trajectories changed dramatically with speed—unlike their intended counterpart aimed towards the targets. The latter could be well characterized as unique geodesics curves on a Riemannian manifold in that they remained on the intended track, were speed- and loads-invariant with low variability and locked in time with the trunk and head immediately preceding the reach initiation as the decision to choose a target was being made.

The instant invention may also be used to evoke automatic cognitive abilities in the children with ASD. This may be done in the context of ToM paradigms, borrowing specific scenarios from it. The instant invention may be used to specifically identify abnormal reflexes in the ASD children, known to be problematic in newborns that go on to develop ASD and AS. The data bank of statistical signatures may be parameterized in both intended and spontaneous automatic movements in TD and used as a template to detect abnormal patters and to correct them in ASD via the robot. The identification of residual reflexes or their absence thereof will guide the programming of movements that the robots will use to co-adapt with the child. It has already been shown that the individual statistical signatures of the natural movement variability in the children with ASD can be shifted towards the normal ranges and that they can perform these experiments in closed loop using real time video-based and self motions as forms of sensory input.

Once the children with ASD are comfortable with the concept of moving in tandem with an external agent and initiating the robot's hand motions in closed loop with the children's hand movements, the recruitment of other robot body parts may be gradually initiated (e.g., NAO has 25 degrees of freedom) by the child. It is known that systematic changes in sensory input reshape the dynamics of their natural movements and these changes can be precisely and objectively quantified across time as the system learns new behaviors. In so doing, it has been possible to decouple DoF that are devoted to intended behavior and that are task relevant from DoF that are incidental to the task, changing spontaneously and subject to different ranges of variability with changes in dynamics. The evolution of the ASD body can be closely monitored as it engages in tandem with the robot so that eventually the child with ASD comes to spontaneously control the ASD robot, without instructions. Fun movements to play may be used that have already been tested in ASD including beginners' martial arts routines and simple instrumental reaching and grasping acts.

The lack of ToM is unique to children with ASD. Children with Down syndrome or other mental disorders do not entirely lack ToM or pretend-play abilities. Moreover some children with ASD can develop deliberate, explicit ToM by 12 years of age and solve the problems that developmental psychology have created to probe their cognitive abilities. They cannot however develop the type of ToM that is implicit, fast, automatic and intuitive. The automatic motions of the children with ASD may be monitored as they interact with their TD peers and the two robots may be used as proxies to promote social exchange. The TD robot information will provide the trajectory in normal development whereas the ASD robot will provide the error data.

The results from the instant methods will lead to new discoveries about how the mind-brain interacts with the body and spontaneously self discovers new solutions to problems. The paradigm of tapping into automatic processes that can be objectively quantified through the statistics of the variability inherently present in natural repeats of unconstrained movements will lead to the understanding of "automatic intelligence" and will broaden the understanding of the spontaneous emergence of ToM during typical development as well as through atypical development. The outcome from the instant methods will provide a set of metrics that enable one to systematically link motor variability and normal/abnormal mental development. It will also enable one to link motor variability with mental illnesses that affect cognitive disabilities specific to improper social interactions. It will create the first comprehensive parameterization of facial expression and emotion statistics ranging from infants to young adults with the corresponding set of body motions, including reflexes, automatic and intended motions. Thus, it will provide the first map identifying the statistics of facial motions and emotions with the corresponding body dynamics across a large range of social and non-social activities. This comprehensive tool will be of utility to the robotics community modeling the phenomena as well as to the clinical community trying to provide the appropriate behavioral therapies.

In accordance with the instant invention, methods for classification leading to diagnosing and/or providing a prognosis for an autism spectral disorder in a subject are provided. In a particular embodiment, the method comprises measuring the motion pattern of the subject upon interaction with an artificial agent, wherein the subject is not provided instruction on how to interact with the artificial agent. The artificial agent provides a stimulus when the subject contacts a region of interest (e.g., a virtual region of interest such a 3D space). A difference in the motion pattern of the subject compared to a healthy individual and/or the presence of a motion pattern associated with an autism spectral disorder indicates that the tested subject has an autism spectral disorder. In certain embodiments, the artificial agent is a dynamic media or interface and may be a robot, three dimensional animate, speaker, or multi-touch surface screen. In a particular embodiment, the artificial agent is a screen and the stimulus is a real-time video of the subject. The methods of the instant invention may further comprise measuring other aspects of the subject (e.g., facial patterns) upon interaction with the artificial agent.

In accordance with another aspect of the instant invention, the methods described herein can be used for determining the sensory capabilities and preferences of an individual. Once determined this sensory modality is used in therapies that examine the patterns of random fluctuations of movement parameters in the movement trajectories of the person's body parts (e.g. hands, head, trunk, limbs, etc.) These random fluctuations over time (over repetitions of the same behavior) serve as a form of re-afferent sensory input that the system integrates with the efferent motor output and utilizes these inputs differently as a function of cognitive complexity in closed loop with cognition. In a particular embodiment, the methods use a set of postures to trigger external media (audio, videos, real time self-videos from a webcam facing the child, or virtual variants of the child embodied in a three dimensional animate that is endowed with the child's physical motions or with noisy variants of it). In a particular embodiment the set of postures thus learned by the subject are associated with intuitive gestures for communication that operate and control external media (e.g. play, rewind, pause, fast-forward, flicker, etc.). In a particular embodiment, the method further comprises measuring a motion pattern of the subject prior to the administration of a therapy (which could be either pharmaceutical or behavioral or both; e.g., to obtain a baseline measurement). In a particular embodiment, the method comprises measuring the motion pattern of the subject upon interaction with an artificial agent as described above, after administering the therapy to the subject to measure performance gains relative to baseline values. The modulation of the motion pattern of the subject after administration of the therapy (e.g., to a normal motion pattern) indicates that the therapy modulates the autism spectral disorder. The direction of this modulation (away or towards typicality, or neutral meaning no change) is evaluated so the effectiveness of treatment can be objectively determined.

In accordance with another aspect of the instant invention, methods of reshaping the improper motion pattern of a subject with an autism spectral disorder are provided. In certain embodiments the subject is allowed to control an artificial agent which initially moves with the stochastic signatures from the dynamics extracted from the physical motions of the subject. Gradually the stochastic signatures of the artificial agent (three dimensional animate or robot) are reshaped so as to harmoniously co-adapt the subject and the artificial agent. In certain embodiments, the method comprises having the subject interact with an artificial agent as described above. In a particular embodiment, the artificial agent is a robot, particularly one programmed to encourage the subject to spontaneously (without explicit instructions or goals) react and move similarly to typically developing children. The subject is in control. The changes work because they are applied to movements that are spontaneous and occur without the subject's intent. These are the movements that do not conserve their motion trajectories as the dynamics of the motion change. The movements that conserve their trajectories and remain invariant to changes in dynamics are the ones under voluntary control and will resist spontaneous changes. Therefore the technique exploits the motions that are collateral, supplemental, and "invisible" to the conscious mind.

As stated herein, the methods described throughout the instant invention can be used for diagnosing, characterizing, classifying (e.g., along a continuum spectrum), assessing, and/or treating a neurological disorder in a subject. In a particular embodiment, the subject is at least 3 or 4 years old. Neurological disorders include neurodevelopmental and neurodegenerative disorders. Specific examples of neurological disorders include, without limitation: Parkinson's disease, parkinsonian syndrome, Autism, Autism spectrum disorder, Huntington's disease, athetosis, dystonia, cerebellar and spinal atrophy, multiple system atrophy, striatonigral degeneration, olivopontocerebellar atrophy, Shy-Drager syndrome, corticobasal degeneration, progressive supranuclear palsy, basal ganglia calcification, parkinsonism-dementia syndrome, diffuse Lewy body disease, Alzheimer's disease, Pick's disease, Wilson's disease, multiple sclerosis, peripheral nerve disease, brain tumor, cerebral stroke, attention deficit hyperactivity disorder (ADHD), Down syndrome, William syndrome, schizophrenias, etc. In a particular embodiment, the neurological disorder is Autism, Autism spectrum disorder, or Parkinson's disease.

In a particular embodiment, the method of the instant invention comprises measuring the motion pattern of a subject upon interaction with an artificial agent, wherein a difference in the motion pattern of the subject compared to at least one control (e.g., a healthy individual and/or an individual with a neurological disorder indicates whether the subject has the neurological disorder and/or the classification or severity of the neurological disorder). In a particular embodiment, the gender and/or age of the subject and the control standards are the same. In a particular embodiment, the artificial agent provides a stimulus when the subject contacts a region of interest. The artificial agent may provide a target or cue to the subject (e.g., a target to touch, such as a dot or light). In a particular embodiment, the artificial agent provides a challenge or test (e.g., match-to-sample test) to the subject that requires the movement and selection of an answer by the subject. For example and as described herein, the artificial agent may present an object and require the subject to touch the object by distinguishing between the object and a second object which differs from the first object by color, shape, orientation, or the like. The subject may or may not be provided instruction on how to interact with the artificial agent. The artificial agent may be a dynamic media or interface. In a particular embodiment, the artificial agent provides a video (e.g., a video of movements by an individual (e.g., karate moves) which can be mimicked by the subject). Examples of an artificial agent include, without limitation a robot, three dimensional animate, speaker, screen (e.g., computer screen), touch screen, tablet (e.g., iPad), and the like. In a particular embodiment, the artificial agent is a screen (e.g., a touch screen).

In a particular embodiment, the motion pattern of the subject's arm is measured. However, any body part can be measured (e.g. hands, head, trunk, limbs, etc.). In a particular embodiment, the difference in size of the body parts (e.g., limb size) of subjects and controls is accounted for (e.g., normalized). The intentional or deliberate motions (e.g., those aimed at a target) of the subject may be measured and compared to standards and/or the automatic or spontaneous motions (e.g., the retracting from a target) may be measured and compared to a standard. Any parameter of the motion of the subject may be measured. Parameters that can be measured include, without limitation: speed profile, max speed, time to reach maximum speed, acceleration, max retraction speed, time to reach max retraction speed, three-dimensional path, accuracy of target touching, percentage correct (when the artificial agent provides a test), overall amount of time for motion, decision movement latency, body part rotation or positioning, and joint angle. The method of the instant invention may also comprise measuring and/or monitoring the facial patterns of the subject during interaction with the artificial agent. In a particular embodiment, the subject is placed in a particular position or orientation (e.g., a primed position) prior to interacting with the artificial agent.

When the artificial agent provides a stimulus (e.g., turns on a stimulus) when the subject contacts a region of interest, the stimulus may be a real-time video of the subject. In a particular embodiment, the stimulus is a video, such as a cartoon video. In yet another embodiment, the stimulus is a three dimensional animate.

As stated hereinabove, the instant invention also encompasses methods for determining the ability of a therapy to modulate a neurological disorder in a subject. In a particular embodiment, the method comprises administering the therapy to a subject and performing at least one of the above diagnostic methods of the instant invention (e.g., monitoring motion upon interaction with the artificial agent) to determine whether the administered therapy modulated (e.g., treated) the neurological disorder (e.g., by comparing to standards or previously obtained standards of the subject). In a particular embodiment, the method comprises performing at least one of the diagnostic methods of the instant invention, administering the therapy to the subject, and performing a second diagnostic method of the instant invention on the subject, wherein a change in the second assay compared to the first assay indicates that the therapy modulates the neurological disorder. For example, if the results of the second assay more closely approximate the pattern of a healthy individual than the first assay, the therapy is effective against the neurological disorder.

In accordance with another aspect of the instant invention, methods of treating a neurological disorder and/or lessening the improper motion pattern of a subject with a neurological disorder such as an autism spectral disorder are provided. In a particular embodiment, the method comprises having the subject interact with an artificial agent which provides a stimulus when the subject contacts a region of interest, wherein the interaction of the subject with the artificial agent lessens the improper motion pattern associated with the neurological disorder.

Definitions

The following definitions are provided to facilitate an understanding of the present invention:

The singular forms "a," "an," and "the" include plural referents unless the context clearly dictates otherwise.

As used herein, "autistic spectrum disorder" or "ASD" refers to autism and similar disorders. Examples of ASD include disorders listed in the Diagnostic and Statistical Manual of Mental Disorders (DSM-IV). Examples include, without limitation, autistic disorder, Asperger's disorder, pervasive developmental disorder, childhood disintegrative disorder, and Rett's disorder. Known ASD diagnostic screenings methods include, without limitation: Modified Checklist for Autism in Toddlers (M-CHAT), the Early Screening of Autistic Traits Questionnaire, and the First Year Inventory; the M-CHAT and its predecessor CHAT on children aged 18-30 months, Autism Diagnostic Interview (ADI), Autism Diagnostic Interview-Revised (ADI-R), the Autism Diagnostic Observation Schedule (ADOS) The Childhood Autism Rating Scale (CARS), and combinations thereof. Known symptoms, impairments, or behaviors associated with ASD include without limitation: impairment in social interaction, impairment in social development, impairment with communication, behavior problems, repetitive behavior, stereotypy, compulsive behavior, sameness, ritualistic behavior, restricted behavior, self-injury, unusual response to sensory stimuli, impairment in emotion, problems with emotional attachment, impaired communication, and combinations thereof.

As used herein, "diagnose" refers to detecting and identifying a disease/disorder in a subject. The term may also encompass assessing or evaluating the disease/disorder status (severity, classification, progression, regression, stabilization, response to treatment, etc.) in a patient. The diagnosis may include a prognosis of the disease/disorder in the subject.

As used herein, the term "prognosis" refers to providing information regarding the impact of the presence of a disease/disorder on a subject's future health (e.g., expected morbidity or mortality). In other words, the term "prognosis" refers to providing a prediction of the probable course and outcome of a disease/disorder or the likelihood of recovery from the disease/disorder.

The term "treat" as used herein refers to any type of treatment that imparts a benefit to a patient afflicted with a disease, including improvement in the condition of the patient (e.g., in one or more symptoms), delay in the progression of the condition, etc.

The following examples are provided to illustrate certain embodiments of the invention. They are not intended to limit the invention in any way.

Example 1

Figure 1:
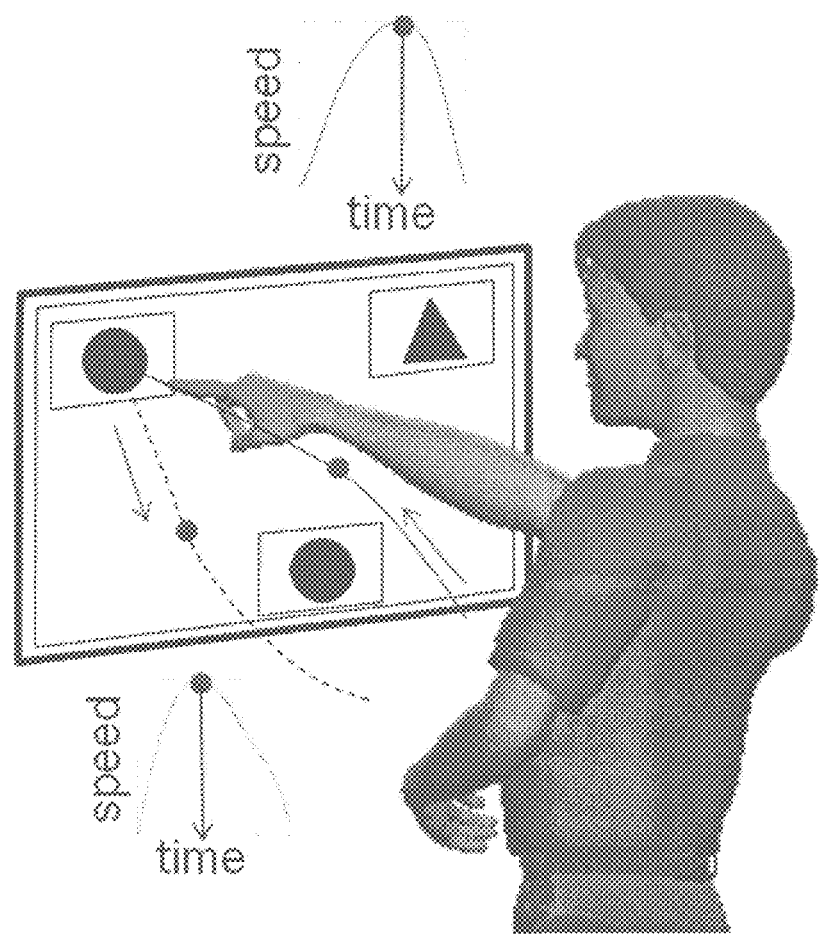

FIG. 1 shows an example of a setup to harness motion trajectories. These motions usually take on the order of 1 second. Typically, only 10-15 minutes are needed to record hundreds of trials and build two frequency distributions, one from the deliberate movements (aimed at the target) and one from the spontaneous transitions (retracting away from the target with no specific aim). The random fluctuations of the maximum speed value are measured along with the random fluctuations of the time to reach the maximum speed value. Sample histograms with fitting distributions are shown in FIG. 2A through FIG. 2D. The spontaneous movements carry the largest amount of cognitive information for children with ASD. For each child, their learning evolution described by their Gamma (a,b) plane trajectories can be tracked as a function of cognitive challenges (FIG. 3A and FIG. 3B). Each one of these cognitive-dependent trajectories (FIG. 3E through FIG. 3F) can be used to assess the individual cognitive improvements of each child with ASD during clinical therapies as a function of time.

To induce cognitive-dependent motor learning, the already-acquired single-peak signature of well-practiced reaches could be spontaneously altered as a function of the cognitive load of the task (Torres et al. (2006) J. Neurophysiol., 96:2613-2632). Here, the challenge of the task was increased from simple perceptual discrimination of color to discrimination of geometric shapes (sometimes making them ambiguous, e.g. square vs. rectangle, circle vs. oval) and also including discriminations that required mental rotation (a banana rotated some number of degrees) in a familiar match-to-sample task. These manipulations induced multiple peaks in the speed profiles (FIG. 3C FIG. 3D) of both movement classes. These changes were quantified individually and as a group. They reshaped the stochastic baseline signature differently for each child and shifted the group's location on the Gamma plane. FIG. 3B shows the shift of each group during the cognitive-dependent motor learning. FIG. 3E through FIG. 3F show the individual trajectories of each child for each of the deliberate and spontaneous learning. Notably, this task evoked much less learning in some children than in others. Further, in the spontaneous learning, some children with ASD crossed over to the TD ranges. The 4 year old child that crossed over was the only one in the ASD1 group beginning to verbalize. Other sensory stimuli or other cognitive tasks can evoke more dramatic changes in some of the children for which this task did not reshape their stochastic signatures as much as it did that of the others.

Example 2

Figure 4:
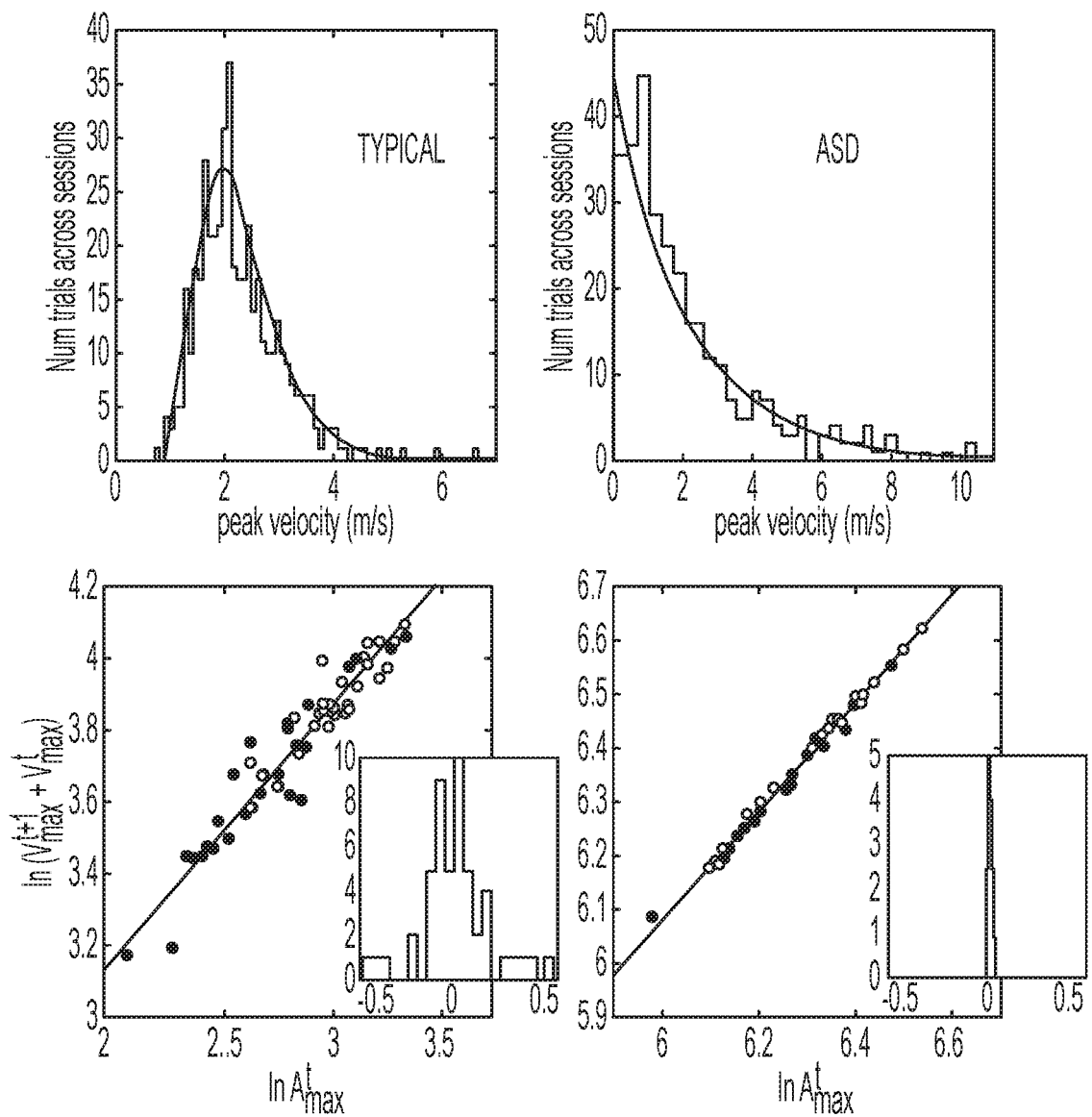
Figure 5A:
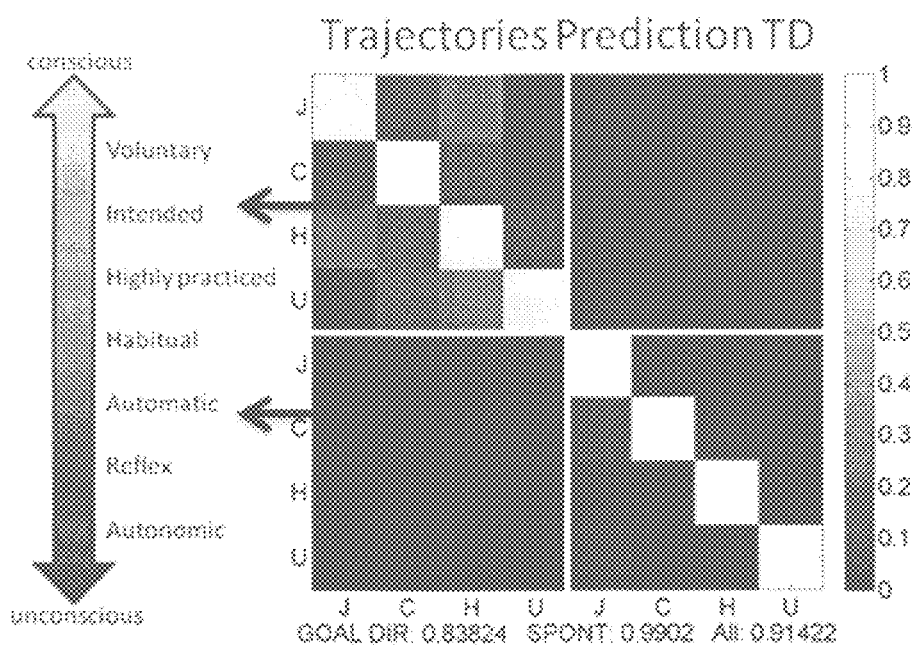
Figure 5B:
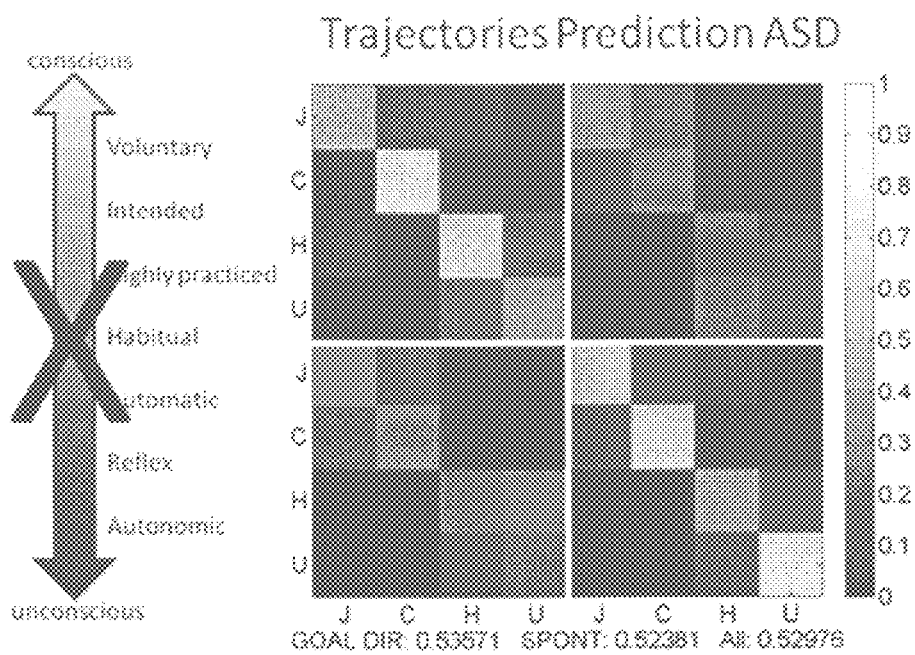
Figure 6A:
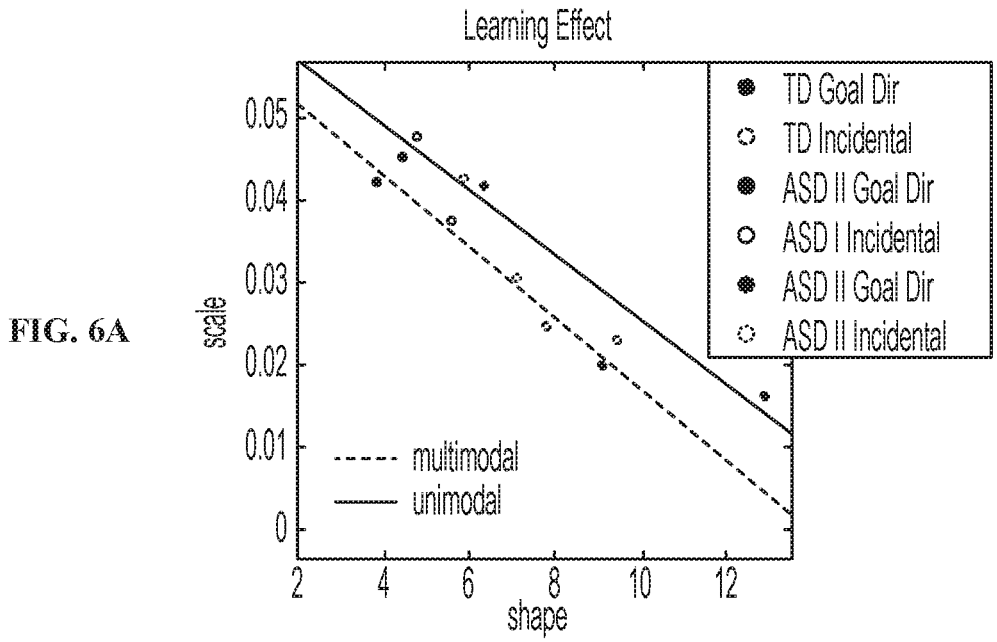
Figure 6B:
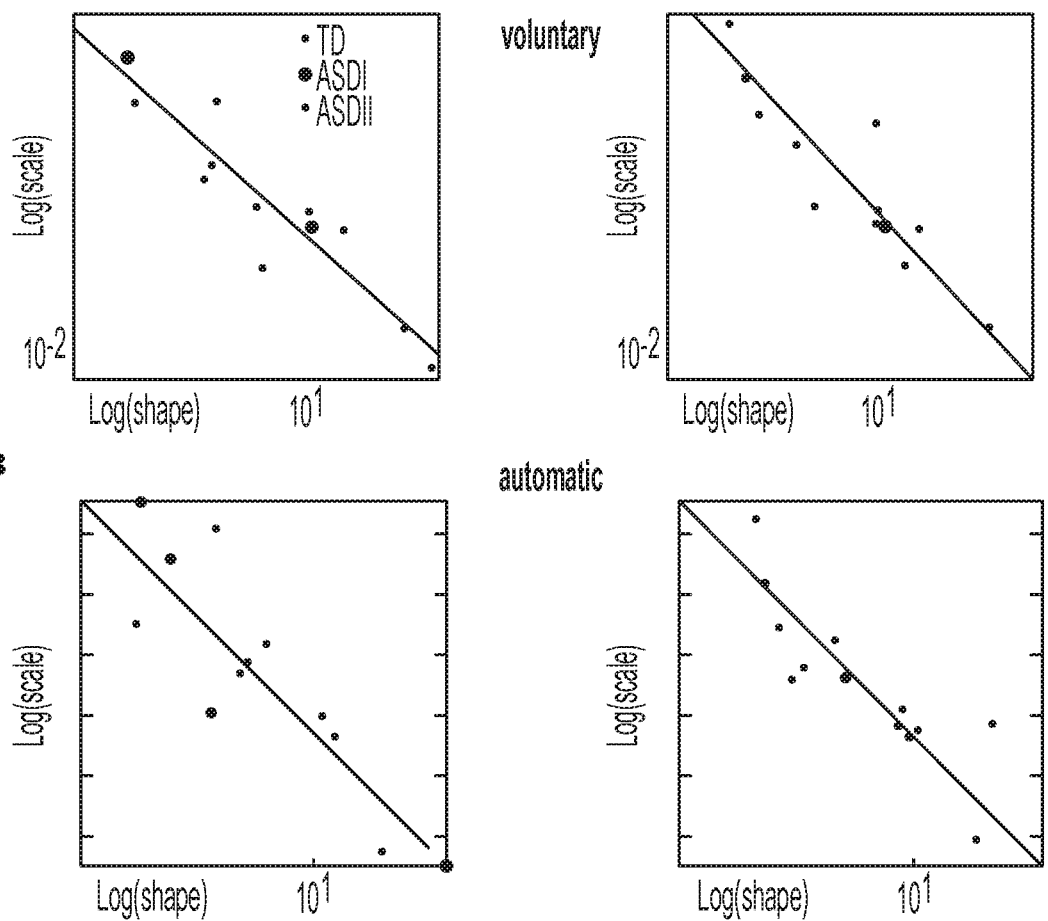

It has been discovered that the distinct statistical signatures of variability (exponential ASD vs. log-normal TD in FIG. 4) and the differential effects that changes in dynamics normally exerted on intentional vs. automatic movements facilitated the accurate prediction of not only the type of action but also the mode of control under which a blindly and randomly chosen hand movement trajectory came from (FIG. 5A and FIG. 5B). This finding has enabled the use of the variability inherently present in natural movements to objectively and reliably diagnose the presence of autism across children of different age groups (FIG. 6A and FIG. 6B). While the variability of intended movements clusters children with ASD far apart from their TD peers, the variability of their spontaneous automatic motions serves to classify each child within a continuum spectrum of disorders according to their sensory preferences as they reshape their movement patterns during motor learning. In the instant paradigm, the "leakage" of cognitive loads was quantified into the children's movements within a familiar pointing task. FIG. 6A shows the group classification whereas 6B unfolds each group into the individual points in phase space obtained from the Gamma fitting across hundreds of movements of each child. Together intended and automatic segments of a movement unit provide a new objective classification tool and a metric of performance to track learning gains in the classroom environment as a function of preferred sensory stimuli.

Example 3

Children interacted with a real-time video of themselves which were projected on the screen between blocks. The task was then adapted to have the children trigger the video images on the screen using real-time biofeedback from their own movements. The output of the sensor attached to their moving hand served as the trigger for the reward (their face's and upper body real time video) in closed loop. This was achieved by creating a virtual region of interest in physical space invisible to the children. The children had to discover this region without instruction in order to trigger the video.

Figure 7A:
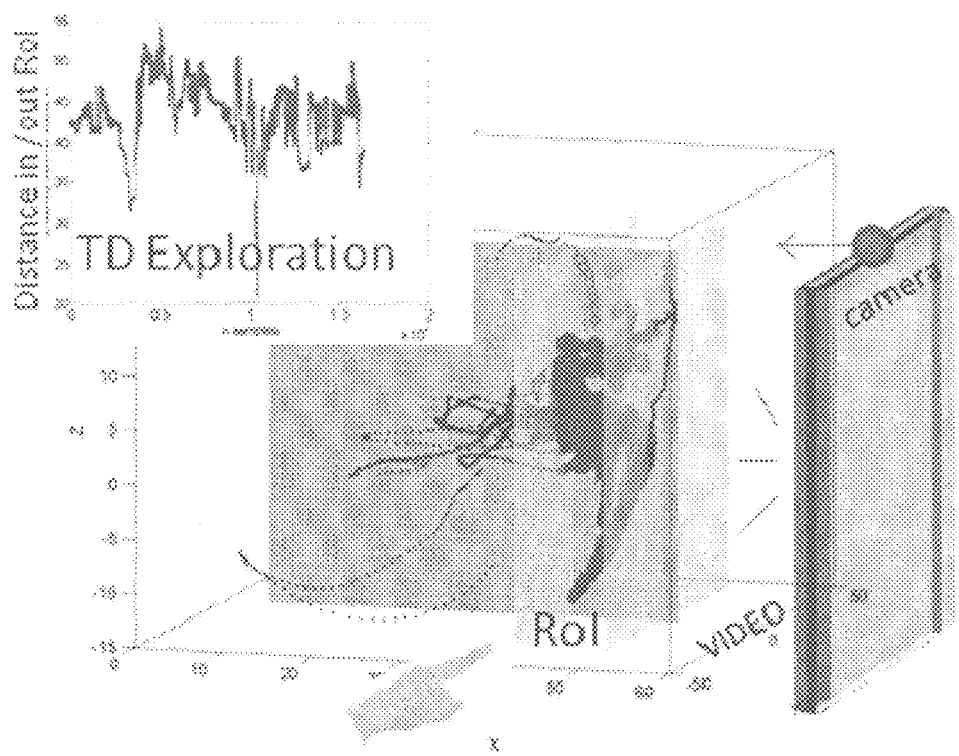

The TD children within two or three sessions lasting a few minutes (up to 15 min) each transitioned from random exploratory movements to more systematic patterns that soon acquired structure. Eventually the TD children intentionally moved the hand in and out of the RoI or sustained the hand inside of the RoI to trigger and/or to sustain their own real-time video showing their faces and upper body in motion (FIG. 7A). Some of the TD children verbalized their realization and explained exactly what was happening.

Figure 7B:
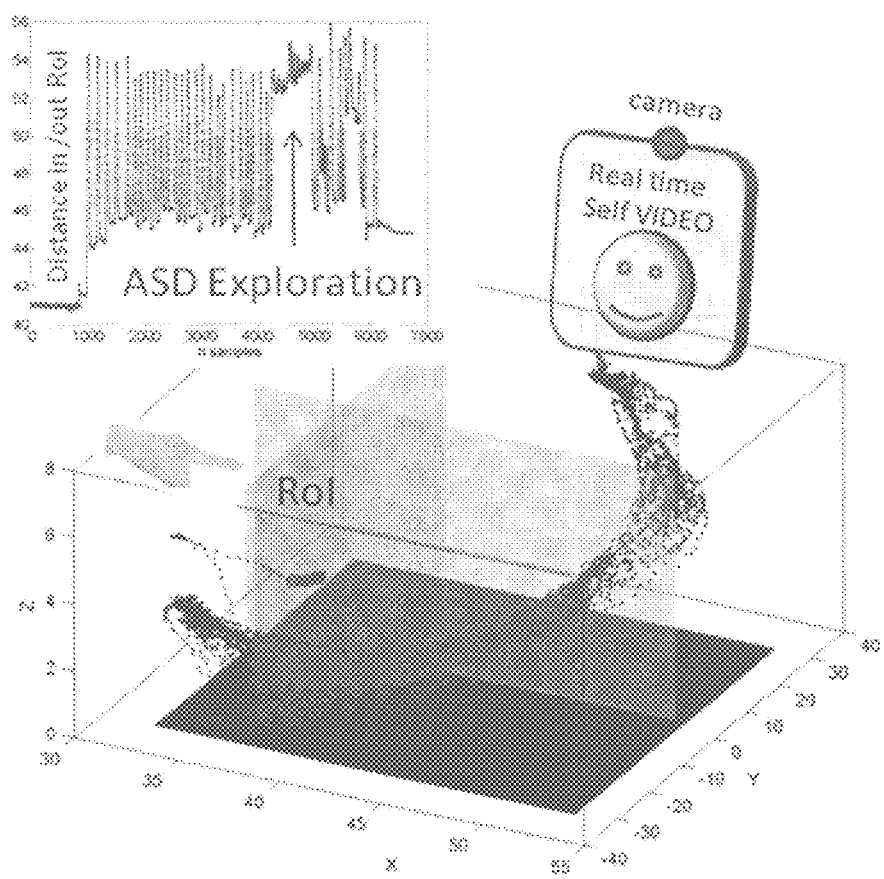

FIG. 7B shows the hand trajectories of a non-verbal, 10 year-old child with ASD as the hand enters and leaves the RoI. Notice the striking differences with the TD patterns in the abnormally low level of noise and variability that makes his motions mechanically as perfect as those of a programmed robot.

Figure 7C:
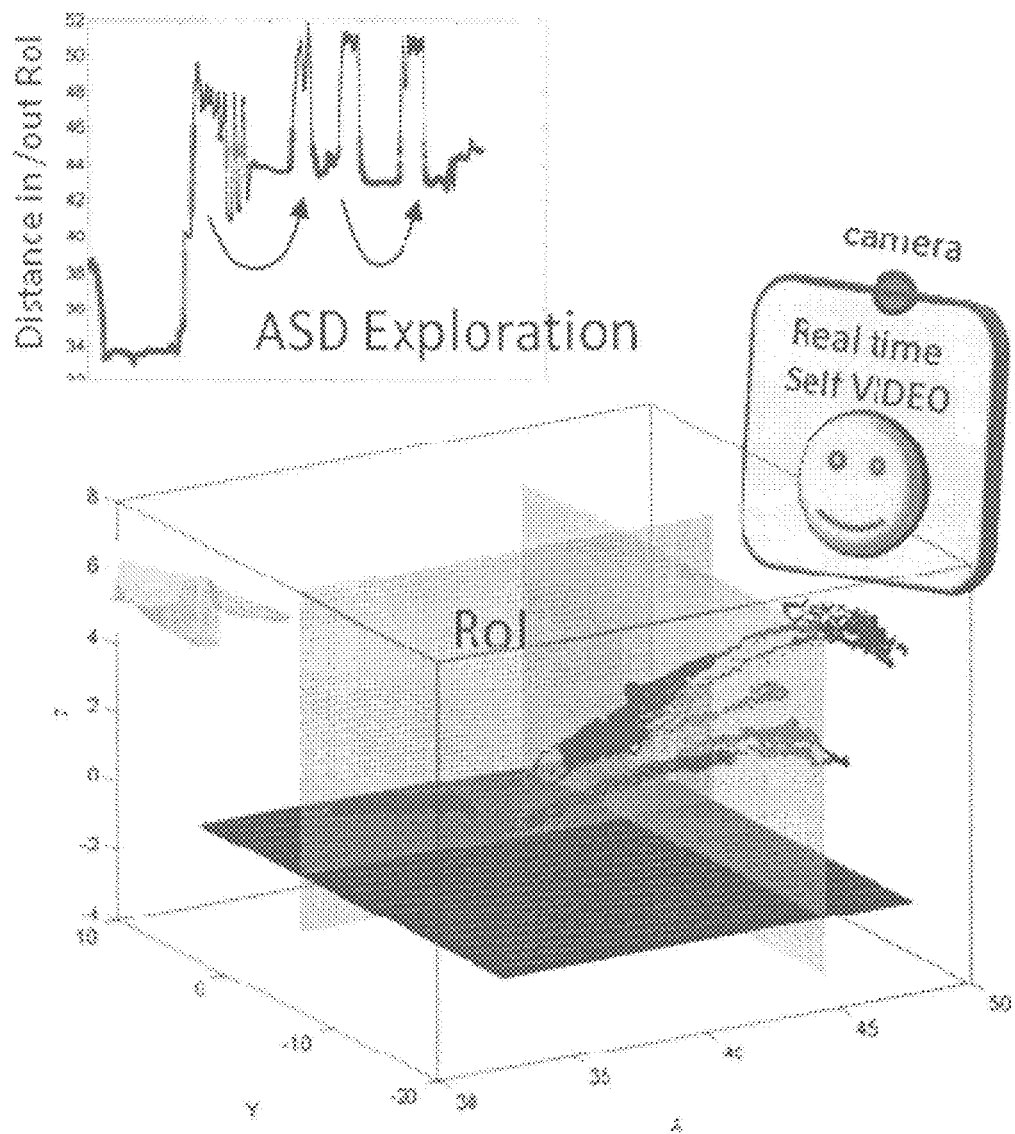

According to their exponential statistical signature these patterns initially lack the differentiation between intended and automatic components that readily emerged in the TD children. This near lack-of-noise/variability was present in several of the children with ASD across all ages (4-15) and for both genders. Importantly within several training sessions (taking only a few minutes a day) the patterns of the children with ASD became more variable (FIG. 7C) and typical learning features such as the multimodal speed profiles in point to point motion segments emerged. These experiments showed that these children can engage in active learning through movement-based therapies that can exploit the Applied Behavioral Analyses (ABA) methods currently dominating ASD training in the pre-school classroom. Importantly ABA which is based on reinforcement learning from the field of psychology can be readily formalized into adaptive reinforcement learning and adaptive dynamic programming frameworks from the fields of computer science and applied mathematics. Real-time physical movements adaptation paired with the real time adapting reward make this conversion from the psychological notions to the computational formalism possible. The introduction of the automatic movement components creates both a computational-research framework for robotics and computer science and a clinical tool for psychology. The introduction of learning based on reinforcement from the statistics of intended and automatic physical movements in closed loop with the reward makes this symbiosis between robotics and cognitive psychology possible and provides proof of concept for the new co-adaptive child-robot paradigm proposed below to target a new form of personalized behavioral therapies that will only require the child's spontaneous exploration without verbal instructions.

Example 4

Herein, objective metrics of sequential movements are provided and a young adolescent with ASD is studied in relation to novice typical controls (TC) as they learned to perform beginners' martial-arts routines. Segments staged to hit an opponent were studied simultaneously performed with supplemental segments. In TC instructed changes in speed had profound differential effects on the intended vs. supplemental segments that were absent in the ASD-case. Moreover the frequency-distribution of velocity and acceleration maxima in TC was well fitted by a Gamma distribution but in the ASD-case the fit was exponential yielding uncannily precise motions with atypically low-range of temporal variability.

The early descriptions of individuals with Autism Spectrum Disorders (ASD) had pointed at an inherent lack of differential responses to people (animate objects) and things (inanimate objects) (Kanner, L. (1943) Nervous child 2: 217-250). More recently, it has been reported that individuals with ASD are impaired at perceiving the actions and emotions of others and at decoding biological motions in general (Blake et al. (2003) Psychol Sci 14:151-157; Kaiser and Shiffrar (2009) Psychon. Bull. Rev., 16:761-777). Interestingly, biological motions possess a spontaneously self-generated component, stochastic in nature that is not present in robotic motions. Predicting the consequences of actions on animate vs. inanimate agents is extremely different in terms of uncertainty. Typically developing children know this distinction somehow by 3 years of age (Gelman and Spelke (1981) Flavell and Ross (eds) Social Science Research Council (U.S.); New York: Cambridge University Press). In the case of children in the spectrum, robotics motions are preferred (Kozima et al. (2007) Frog. Brain Res., 164:385-400), perhaps because they are very predictable much like the types of restrictive and repetitive behaviors that characterize individuals diagnosed with ASD. Since robots are generally programmed by others to fulfill some sets of goals and configurations with great precision, the deterministic nature of their motions makes them very reliable. There is high certainty in predicting the consequences of such motions—in marked contrast with predicting the consequences of spontaneously self-generated biological motions.

Biological movements can be sensed visually through the observation of the motions of others, but they can also be sensed kinesthetically through one's own physical motions. As one moves around and interacts with the world the fluctuations of body positions over time are a form of (kinesthetic) sensory input (sometimes also referred to as proprioception—"one's own conscious or unconscious perception") that generally informs the CNS about internal states of the body and external states of various elements in the environment. Adequately sensing movement variability through the fluctuations of movement parameters across repetitions of the motion can help one understand both internal and external changes and respond consequentially in a reactive or in a predictive manner Since atypical perception of biological motions has been reported in ASD (Blake et al. (2003) Psychol Sci 14:151-157; Kaiser and Shiffrar (2009) Psychon. Bull. Rev., 16:761-777) and motor and visuo-motor integration deficits are known in ASD (Leary and Hill (1996) Ment. Retard., 34:39-53; Jansiewicz et al. (2006) J. Autism Dev. Disord., 36: 613-621; Geschwind, D. H. (2009) Annu. Rev. Med., 60: 367-380; Mostofsky et al. (2009) Brain 132:2413-2425; Rinehart et al. (2006) J. Autism Dev. Disord., 36:757-767; Fournier et al. (2010) J. Autism Dev. Disord., 40:1227-1240; Nayate et al. (2011) J. Autism Dev. Disord., 42:707-17) there is a chance that the kinesthetic sensing in ASD may be also atypical and give rise to atypical perception of internally sensed movements. It is not known in general if the visual perception of external motions is connected in any way with proprioception. A good starting point to investigate this open question is to understand the statistical properties of physical movements using a probabilistic framework. This gives a window into the certainty and the predictability of typical sensory-motor systems and helps uncover atypical scenarios.

In ASD research the perception of external motion—whether biological or mechanical—has been addressed but detailed assessment of actual physical movements remains underexplored. There is a sense that proprioception may be different in ASD (Minshew et al. (2004) Neurology 63:2056-2061; Vakalopoulos, C. (2007) Med. Hypotheses 68:574-600) although more recent work involving high functioning individuals in the spectrum points to potential deficits in the representation of internal models rather than to deficits in proprioceptive sensing (Fuentes et al. (2010) J. Autism Dev. Disord., 41:1352-61; Haswell et al. (2009) Nat. Neurosci., 12:970-972.). Although, internal models and proprioception are necessarily interconnected, there is currently no objective methodology available to systematically quantify in ASD specific deficits in sensory-motor integration and sensory-motor transformations required to develop proper internal models.

The development of objective methods to assess atypical sensory-motor processing could involve movement variability, a ubiquitous property of repetitions of a given motion. The statistical patterns of movement variability in individuals with ASD may reveal some features of their kinesthetic sensing, particularly during the learning of new movements. Variability, in general, has been quite informative of learning and error correction strategies of typical systems (Bernstein, N. A. (1967) The co-ordination and regulation of movements, Oxford, N.Y.:Pergamon Press; Latash et al. (1996) Dexterity and its development, Mahwah, N. J.: L. Erlbaum Assoc.; Newell and Corcos (1993) Variability and motor control, Champaign Ill.: Human Kinetics Pub.), particularly during development when "infants capitalize on inherent variability in order to perform coordinated task-specific activities" (Bernstein, N. A. (1967) The co-ordination and regulation of movements, Oxford, N.Y.:Pergamon Press; Thelen and Smith (1994) A dynamic systems approach to the development of cognition and action, Cambridge, Mass.: MIT Press). Different sources of variability, from both the central and the peripheral nervous system, are known to contribute to the natural variability of typical movements (Faisal et al. (2008) Nat. Rev. Neurosci., 9:292-303; van Beers wt al. (2002) Philos. Trans. R. Soc. Lond., 257:1137-1145; van Beers et al. (2002) Curr. Biol., 12:834-837). Yet, it is not known how these manifest in ASD. In particular one would need to assess if the ASD system can distinguish between the patterns of variability of movements that are deliberately directed to accomplish a goal (or a set of goals) and spontaneously self-generated movements that are incidental to the task goals.

Herein, two fundamentally different movement classes with patterns of variability that map onto different levels of voluntary and automatic control have been identified in TC. Given that kinesthetic sensing of movements gives rise to conscious and unconscious proprioception routed through distinct afferent pathways (O'Rahilly et al. (2008) Basic Human Anatomy: A regional study of human structure. Darmouth) a question related to movement variability is whether movement output variability (which serves as afferent kinesthetic input) can be distinguished in this ASD case—as it is typically distinguished in age-matched controls between (conscious) voluntary and (unconscious) automatic modes of the same act. This question is important because deficits in spontaneous-incidental movements that are below voluntary control could not be solely accounted for by cognitive deficits or deficits in understanding instructions of a task. If the typical distinction between voluntary and automated modes of action was blurred in this ASD case, then deficiencies in the balance between automated and voluntary processes could be established in this individual above and beyond higher-level cognitive impairments. Automated processes are largely controlled by sub-cortical structures that have been identified as problematic in ASD. These include structures involved in unconscious proprioception (cerebellum); unconscious orienting of the body for approach/avoidance behaviors (amygdala) and balancing voluntary and automated control (striatum) (Nayate et al. (2005) Brain Res. Bull., 67:327-334; Mostofsky et al. (2009) Brain 132:2413-2425; Courchesne, E. (1991) Pediatrics 87:781-790; Courchesne, E. (1997) Curr. Opin. Neurobiol., 7:269-278; Schumann et al. (2004) J. Neurosci., 24:6392-6401; Amaral et al. (2008) Trends Neurosci., 31:137-145).

Case Report

JG is a high-functioning verbal, 19 year-old diagnosed with Pervasive Developmental Disorder (NOS) at the age of 3 and with Pervasive Developmental Disorder (NOS)/Autism Spectrum Disorders later at the age of 5. At 10 months he suffered from recurrent ear infections and had tubes placed to drain the ears. This resulted in mid ear damage. He experienced early balance problems and experienced severe language delays but could gesture to ask for things and point at things that he needed/wanted.

His chromosomal analyses for Fragile-X and thyroid function studies were negative. He had no dysmetria or ataxia. At 3 years, 3 months of age he began receiving speech therapy three times a week as well as occupational therapy. At present he has graduated from high school in a fully mainstream setting with a personal classroom aide. His biggest strength is in perceptual organizational/visual processing with very superior range in all psychological testing. He is gifted at drawing and composing three dimensional visual puzzles. He still has difficulties maintaining attention and is extremely disturbed by uncertainty. Any questions related to emotional states or to the future are also very distressing to him.

He came with his sister and observed her performance of the martial arts, then immediately and remarkably, after a few minutes and for the first time ever in his young life he was able to reproduce the entire sequence at once.

His most recent ADOS score were: Communication—6. Autism (Autism cut-off=3, Autism spectrum cut-off=2); Reciprocal Social Interaction—11. Autism (Autism cut-off=6, Autism spectrum cut-off=4); Communication and Social Interaction Total—17. Autism (Autism cut-off=10, Autism spectrum cut-off=7).

He was also administered the Wechsler Abbreviated Scale of Intelligence (WASI). The WASI is a short and reliable measure of intelligence that assesses general intellectual functioning. This abbreviated form was chosen since it is highly correlated with the traditional longer Wechsler Scales and is well suited for research laboratories such as ours. All four subtests were used in this case: Vocabulary, Block Design, Similarities, and Matrix Reasoning. Vocabulary measures the individual's expressive vocabulary, verbal knowledge, and fund of information. Block Design measures spatial visualization, visual-motor coordination, and abstract conceptualization. Similarities scale measures verbal concept formation, abstract verbal reasoning ability, and general intellectual ability. Matrix Reasoning measures non-verbal fluid reasoning and general intellectual ability. Scores are reported as a verbal score, performance score, and full-4 score. WASI scaled scores represent performance of the individual in comparison to people from 6 to 89 years of age. Individual subtest scores are reported as T-scores so that a score of 41-59 is considered within the average range: Vocabulary (31); Block Design (67); Similarities (41); Matrix Reasoning (61). His Verbal IQ was 79; Performance IQ was 125 and Full-4 IQ was 100.

Method

Performance of a second-degree black-belt martial arts expert (22 years old) was measured on all behavioral tasks in order to serve as a reference for 5 novice participants (ages 19-23 years old). Novices included the 19 year-old high functioning verbal participant with ASD. The normal control novices (TC) and the expert were undergraduates at Rutgers University. The Rutgers University Institutional Review Board in compliance with the Declaration of Helsinki approved the protocol for the movement studies. Consent for videotaping was obtained from all participants and also from the parents of the participant with ASD.

Beginners' martial arts routines were performed by the expert and also instructed under his supervision. Four techniques named Jab, Cross, Hook, and Uppercut were used both in isolation and as a fluid interconnected sequence. Each technique had a staged and an incidental segment, which explains why martial arts techniques were chosen as a paradigm to assess potential differences on modes of control. The staged segment was deliberately aimed at an opponent (e.g., extension of a limb toward a target). The incidental segment was a spontaneous transition towards another technique (e.g., retraction of a limb while the other was extended). These interleaved staged and incidental segments were present in both the isolated techniques and in the fluid sequences of each technique. A minimum of 4 sessions for isolated and 4 sessions for sequenced techniques were recorded across different forms of sensory feedback conditions and speeds. A minimum of 10 trials per speed type for each of the isolated and sequenced techniques were recorded (2 speeds×10 trials×4 isolated techniques×4 sequenced techniques for 320 trials minimum in one sensory condition out of 3 described below). The densely sampled trajectory analyses provided statistical power to make a statement about each individual's statistical signature of motor variability. Distributional analyses to be made precise later provided the means to compare the case with ASD against the expert and the other novice participants. From the entire set in a given subject, less than 5% of the trials were discarded due to failure to initiate movement upon cueing it, or due to failure of the experimenter to trigger the recordings. The speed of the movement (slow or fast) was explicitly cued by the experimenter at the start of the movement in a block design. In separate sessions, different forms of sensory guidance were used:

1. Direct imitation: Participants imitated the expert as he performed each technique first in isolation and then in sequence.

2. Simulation (from memory): In the absence of the source of imitation (the expert) the participants had to recall in full illumination the isolated segments of each technique and perform them from memory first in isolation and then in sequence to simulate the defensive attack towards an imaginary opponent.

3. Mirror guidance: In full illumination of the room the participants simulated the techniques from memory but this time in front of a full-body sized mirror both in isolation first and then as the full sequence.

Each participant returned several times to the lab for practice and movement recordings under the expert guidance. Data collected across these visits are reported.

Movements were monitored in real time and captured at 240 Hz using 16 electro-magnetic sensors (Polhemus, Liberty, Colchester, Vt.) and motion-tracking software (The Motion Monitor, Innovative Sports Training, Inc., Chicago, Ill.) (see Appendix for further details). The output kinematics features of the movement trajectories from both hands were analyzed. Sensors were mounted on the forehead (1), trunk (2), both shoulders (2) (acromial positions), both upper arms (2) (brachial positions), both forearms (2) (ante brachial positions), both hands (2) (on the top, manus position, opposite to the palms), both upper legs (2) (femoral positions) and both lower legs (2) (at the crural positions on the front of the shanks). The 16th sensor was used to digitize the body and render the three dimensional replica of the subject. This enabled calibration of the rotations and displacements within the range of motions explored. The professional software to digitize, render in 3D and calibrate the system is provided by the Motion Monitor Sports Inn. FIG. 8A shows a 3D replica model of the expert subjects' body and the axes of the 15 sensors. This real time visualization allowed the experimenters to obtain both real time feedback during the calibration step as well as a posteriori visual confirmation of the correctness and fluidity of the performance after each block of trials. During performance participants were not provided with this feedback. For simplicity only data for the right and left hand are presented.

Analytical Methods

First, the statistical effects of instructed changes in speed on the hand trajectories of intended and incidental segments of each technique were assessed in each TC individual and in the case with ASD. Second, a linear classifier was used to predict which technique and control mode a randomly chosen trial most likely came from based on the patterns of variability of the trajectories' maximum curvature; and compare the performance of the linear decoder in TC vs. ASD. Finally a distributional analysis of the variability of the maximum speed values for each of the goal-directed and incidental segments of the technique were determined to ask if the statistical properties of the movement trajectories of the case with ASD fell in a different statistical class than those of the TC individuals.

Statistical Analyses of Hand Trajectories in Three Dimensions

The Wilk's lambda statistic has the likelihood ratio test $$\Lambda = \frac{\det(E)}{\det(E+H)}$$

written in terms of the 'within' sum of squares and products matrix E and the 'total' sum of squares and products matrix (E+H). The matrix $$E = \sum_{ij} y_{ij} y_{ij}^t - \sum_i \frac{1}{n} y_{i.} y_{i.}^t$$

where $y_{ij}$ is a sample point and $$y_{i.} = \sum_j^n y_{ij}$$

is the total sum of the i-th sample. The matrix $$H = \sum_i^k \frac{1}{n} y_{i.} y_{i.}^t - \frac{1}{kn} y_{..} y_{..}^t$$

where $$y_{..} = \sum_i^k \sum_j^n y_{ij}$$

is the overall total. This test is similar to the univariate F-test. It is a multivariate generalization of the univariate F-distribution (and generalizes the Hotelling's T-square distribution as the F-distribution generalized the Student's t-distribution (Mardia et al. (1979) Multivariate analysis, NY:Academic Press)).

It was used in each three dimensional vector along the hand trajectory. The use of determinants reduces the test statistic Λ to a scalar, making it possible to decide whether the separation of mean vectors is significant. When $\Lambda \leq \Lambda_{\alpha,d,vH,vE}$ (Λ small), the null hypothesis is rejected. In $\Lambda_{\alpha,p,vH,vE}$, α is the level of confidence, d is the number of variables or dimension, vH=k−1 and vE=k (n−1) are the degrees of freedom for hypothesis and error respectively, k is the number of conditions and n the number of trials.

The Wilk's lambda rule rejects the null hypothesis of mean equality for $\Lambda \leq \Lambda_{\alpha,d,vH,vE}^*$ where α=0.05, d=3, and $v_H=2-1$, $v_E=2(10-1)$, are the degrees of freedom for hypothesis and error terms respectively for the hand paths. Herein, the number of samples k=2, (slow vs. fast within each control type, intended or incidental). Each block has 10 trials. Thus the number of points per sample-condition is n=10. $\Lambda_{\alpha=0.05,d=3,\ vH=1,vE=18}^* =0.803$ (taken from (Rencher, A. C. (1995) Methods of Multivariate Analysis, New York: John Wiley and Sons; Appendix B p. 427). Values of Λ that cannot reject the null hypothesis as such that $\Lambda > \Lambda_{\alpha,d,vH,vE}$ Movement Classification A simple leave-one-out cross-validation algorithm (Quian Quiroga et al. (2006) J. Neurosci., 26:3615-3620) was used to ask—based on the hand trajectory curvature—which technique (Jab, Cross, Hook or Uppercut) and segment type (strike or retracting) a randomly selected trial most likely came from. Each technique had a goal-directed (strike) and a supplemental (retracting) segment with different levels of control and functionality. Each hand trajectory also had different curvature, so it was then determined to what extent the variability of the maximum curvature changed when the segment was intended than when it was spontaneously supplementing the technique.

For each technique type (a total of 4 techniques) 55 trials were used for a total of 220 trials per movement type (a total of 2 movement types). Trials were represented as points in an m-dimensional space, each coordinate corresponding to the parameter of choice (maximum bending (meters)) input to the decoding algorithm for each of the m subjects (m=6, one expert and 5 novices). One at a time, data from each trial picked at random was used to predict the trajectory parameter from a technique and movement type (chance p<=⅛, 4 techniques and 2 movement types), based on the parameter-distributions derived from all the remaining trials (leave-one-out cross validation) and was assigned to the class of its nearest neighbor in the m-dimensional space using Euclidean distance (Duda et al. (2001) Pattern Classification, New York:Wiley).

For assessing statistical significance of the decoding results, a value of 1 was assigned to correctly predicted trials and a value of 0 to the incorrectly predicted ones. The mean of the sequences of correctly and incorrectly classified trials were compared statistically using a non-parametric Wilcoxon rank test (Zar, J. (1996) Biostatistical Analysis, Upper Saddle River, N.J.:Prentice-Hall) and represented graphically as confusion matrices. Upon analyses including all 6 participants at once, each individual separately (m=1) was separately examined to determine the worst and the best performance. The individual analysis was performed on the data from the case with ASD to ask if one could blindly classify his movements into goal-directed and spontaneous segments for each technique without confusion.

Distributional Analysis

Figures 9A, 9B, 9C, 9D:
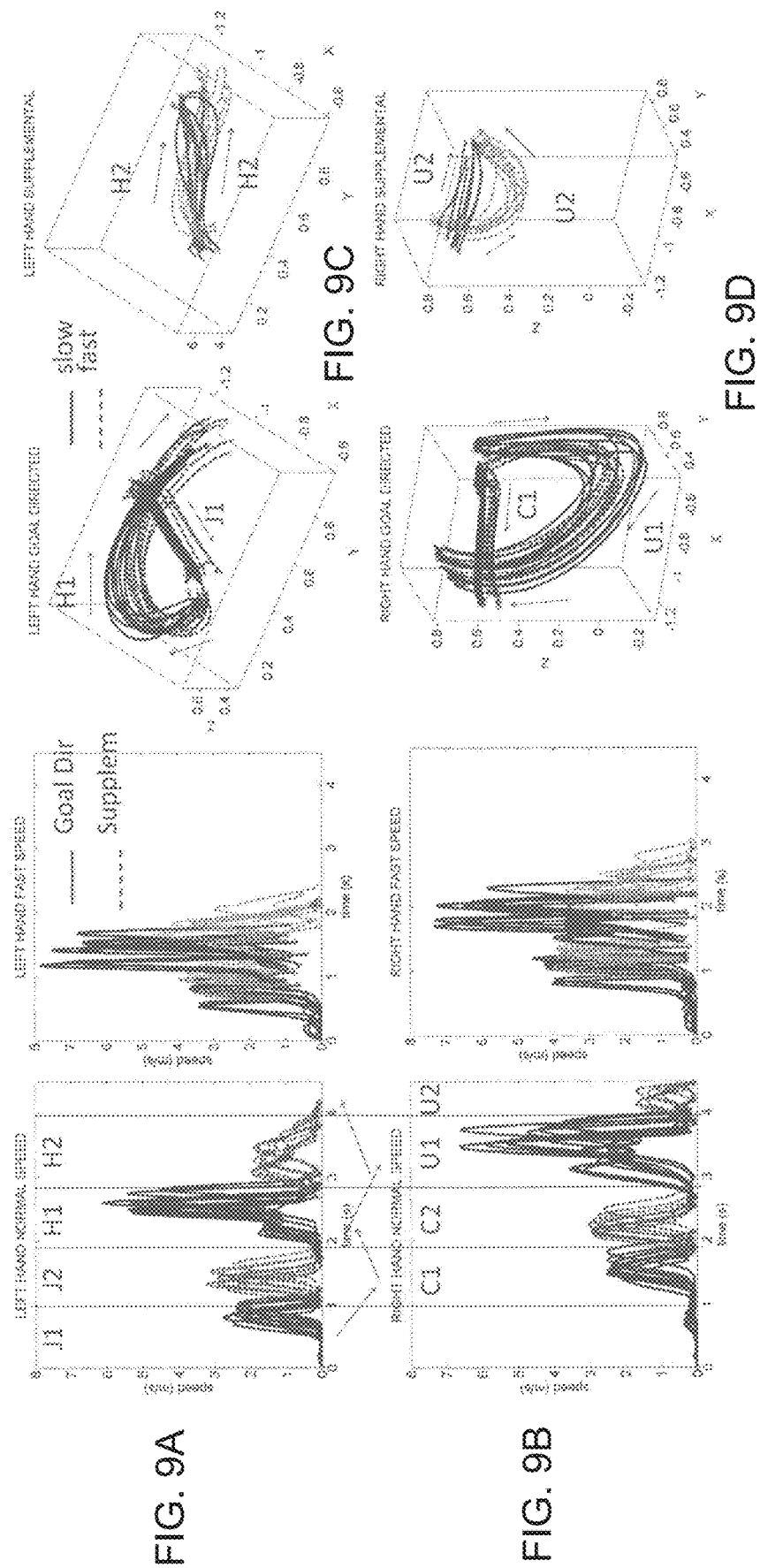

The speed profiles along the motion trajectories were obtained. To this end the Euclidean norm (the length) of the velocity vector tangential to the curve described by the hand movements was measured in each of the three dimensional hand trajectories of FIG. 9A and FIG. 9B and obtained the instantaneous speed scalar value. Each sub-segment of each technique had a maximum value which was determined along with the time at which this value was attained from the technique's movement onset. The hand velocity signaled movement at above 5% of the maximum velocity value of the segment. Likewise, the sensors software directly outputs the acceleration vectors in three dimensions as well as their instantaneous norm to analyze the instantaneous acceleration profiles. In-house designed Matlab software obtains their maximum scalar values for each sub-segment of the technique. Across all repetitions and sensory conditions, the histograms of these maximal values of speed and acceleration were constructed to investigate the statistical properties of their frequency distributions. The histograms and estimation of the bin size for the parameters of interest were obtained using Matlab routines based on well established algorithms for optimal bin-size estimation with $W=3.49 \sigma N^{-1/3}$ (Scott, D. (1979) Biometrika 66:605-610; Izenman, A. J. (1991) J. Amer. Stat. Assoc., 86:205-224) where W is the width of the histogram, $\sigma$ the standard deviation of the distribution (the estimated standard deviation s was used) and N is the number of samples.

Movements

The first isolated technique is called a Jab. The Jab starts with the front hand extending towards the imaginary opponent's nose (J1), keeping the hand in a tight fist, making sure that the elbow does not hyperextend; the hand should be retracted while it is still slightly bent (FIG. 8A). At the same time that the Jab is being retracted (J2) the Cross is being extended forward (C1). Again the imaginary target is used and the Cross is directed towards the nose. Simultaneously, the body is twisting, beginning with the back foot, then the torso and ending with the back of the hand extending forward. Because the body is already twisted this motion naturally sets up the staged portion of the Hook (H1) aimed at the opponent. As the Cross (right hand) reverts back to its original position (C2) the left forearm is made into a C-shape with the hand in a fist and the palm facing down, and the body untwists itself, using the momentum of the body rather than the force of the hand to achieve the intended goal (to reach the opponent's face). As the body untwists itself in an incidental H2, the knees bend slightly in preparation for the intended Uppercut (U1). After the knees are bent and the left hand is returning to its original positioning to protect the face, the right hand fist shoots up in a motion that resembles throwing a bowling ball, but the hand is kept tighter aligned to the body and the palm facing the body. The incidental portion U2 brings the hand back and the body adopts the defense position again (FIG. 8K bottom panel-end of the cycle). It is important to note that all routines where done in the presence of an expert instructor in order to minimize risk of injury.

Results

Differential Effects of Speed on the Goal-Directed Vs. Supplemental Movement Trajectories Present in TC are Absent in the ASD Case Regardless of expertise level or of the complexity of the technique, the changes in speed affected the goal-directed and the supplemental segments of each technique differently in TC. FIG. 9A through FIG. 9D shows the performance of the expert. FIG. 10A through FIG. 10H shows the performance of a TC novice. Notice that as in the expert, the effects of speed were different in the goal-directed segments (the trajectories are conserved) than in the incidental segments of the technique (the trajectories changed), albeit with more variability in the novice than in the expert's motions. In each technique for the novice in FIG. 10A through FIG. 10D the trajectories from the intended segments remained similar despite changes in speed ($\Lambda > \Lambda^*$) for each point along the path, but the corresponding incidental trajectories split according to speed type ($\Lambda \ll \Lambda^*$) (Rencher, A. C. (1995) Methods of Multivariate Analysis, New York:John Wiley and Sons)—Wilks A-test, a 0.05). This was the case particularly for the highly curved movements (Hook and Uppercut).

FIG. 11A through FIG. 11H shows the performance of the individual with ASD. Important to notice is that unlike in the TC the different instructed speeds had no differential effects between the staged and the incidental segments of the techniques. In the TC these differences were particularly evident in the different trajectories of the incidental segments. By contrast in the ASD case whatever the effect of speed was in the staged segments, it was present as well in the incidental segments of each technique. For example FIG. 11A from the ASD case shows how the staged trajectories of the Jab split into slow and fast curve families and these families are also present in the incidental transitional movements with similar speed effects in both modes (all reported values at a=0.05 level) (in both intended and incidental the $\Lambda \ll \Lambda^*$). Contrast this with the Jab in FIG. 10A from the TC novice. In the novices—as in the expert—the trajectories of the staged Jab forward remained similar despite changes in speed ($\Lambda > \Lambda^*$) for each point along the path, but the corresponding incidental trajectories split according to speed type ($\Lambda \ll \Lambda^*$). This was the case particularly for the highly curved movements (Hook and Uppercut). As in the expert performance, the novice performance conserved the intended course of action in the physical curves but the incidental trajectories changed according to speed type. FIG. 10C FIG. 10D show typical examples from the TC. Contrast this with the FIG. 11g FIG. 11D of the ASD case, where the speed effect was similar in the two modes.

The incidental trajectories in ASD were as similarly affected by the speed as the staged ones were, and had different shapes than those of the novice. In the ASD case the incidental trajectories were more variable but not to the point of splitting into different families of curves ($\Lambda \ll \Lambda^*$). Statistically speaking (Rencher, 1995)—Wilks A-test, $\alpha=0.05$, they were not significantly different along the path as in each of the TC.

The lack of differentiation between intended and incidental movement trajectories in the ASD case was further investigated below using a linear classifier.

The Movement Trajectories of the ASD Case Cannot Differentiate Between Goal-Directed and Automatic Levels of Functionality The leave-one-out cross-validation procedure revealed that it was possible to accurately predict for a randomly chosen trial not only which technique the trial came from but also, without confusion, if a given technique segment was from the strike portion or from the retracting portion. Using the maximum bending of the trajectory the predictive value of the trials was high (0.83 for the strike and 0.99 for the transitional retracting ones). FIG. 11A through FIG. 11H shows the results in the form of confusion matrices for the group of subjects (A); for the worst individual performance (B) and for the case with ASD (C). Rows are actual values from the data sets. Columns are assigned values from the leave-one-out cross-validation algorithm using nearest-neighbor criterion. The 4 upper diagonal values represent the predictability level of each technique within the intentional-strike mode. The 4 lower diagonal values represent the same for the spontaneous supplemental segments of each technique. Off-diagonal values within each mode (4-technique quadrant) indicate if there is confusion of one technique with another. Off-diagonal values in the 2-mode quadrants indicate if there is confusion between goal-directed and spontaneous segments.

Three main results stand out: (1) The retracting movements do a better job at distinguishing the techniques both for the group performance and for the individuals' performance (this is also reflected in Table 1); (2) In TC the strikes of each technique (goal-directed segments) are never confused with the spontaneous retracting segments. Even for the worst individual's decoding performance the distinction remains (this is shown in FIG. 11A-group performance and 11B worst-individual performance); (3) The case with ASD cannot distinguish the goal-directed from the spontaneous segments albeit the prediction of the technique type is above chance. The variability in his hand trajectories can distinguish a Jab from an Uppercut but cannot distinguish if the Jab segment was its intended strike or its retracting supplemental segment.

Notice that FIG. 11A shows the results from a population analysis including all 6 participants, so it makes a statement about the overall variability in this group of people regarding these techniques and movement types, for the hand trajectories' maximum bending. The same analysis for each individual yielded a result that depended on the level of training. The expert had the highest predictive accuracy of technique-plus-movement type but one subject yielded 0.55 in the strike segments, 0.75 in the spontaneously retracting segments and 0.65 mean diagonal. These values were still well above chance ($p<=1/8$) yet much worse than the expert's (overall diagonal 0.85) and than other subjects who seemed to have learned at a faster rate. These disparate levels of decoding performance were expected. The surprise was in the TC cases how well the decoding algorithm captured the differences in movement types with no confusion between groups of movements even in the worst case (FIG. 11B) but how poor the decoder performed in the case with ASD. Even though the individual techniques within each movement type could be confused in most novices, the two movement types across all techniques were not confused. This clearly established two movement classes which corresponded to the strike and retracting portions of the techniques and which the ASD system could not distinguish.

TABLE 1

Predictive values of the Linear Decoder. The predictive values of the leave-one-out cross validation procedure on which technique and movement type a blindly chosen trial most likely came from. Chance is 1/8. (Max K stands for maximum curvature, Max S stands for maximum speed).

| | Movement Functionality | | |
|---|---|---|---|
| | Goal-dir | Supplem | Diagonal |
| Expert | 0.75 | 0.85 | 0.93 |
| Novice 1 | 0.73 | 0.78 | 0.83 |
| Novice 2 | 0.70 | 0.80 | 0.89 |
| Novice 3 | 0.61 | 0.59 | 0.66 |
| Novice 4 | 0.55 | 0.65 | 0.75 |
| Novice 5 | 0.69 | 0.69 | 0.70 |
| Ensemble | 0.83 | 0.91 | 0.99 |
| ASD Max K | 0.70 | 0.69 | 0.70 |
| ASD Max S | 0.53 | 0.52 | 0.52 |

Exponential Distribution of Velocity and Acceleration Maxima in ASD

Figure 13A:
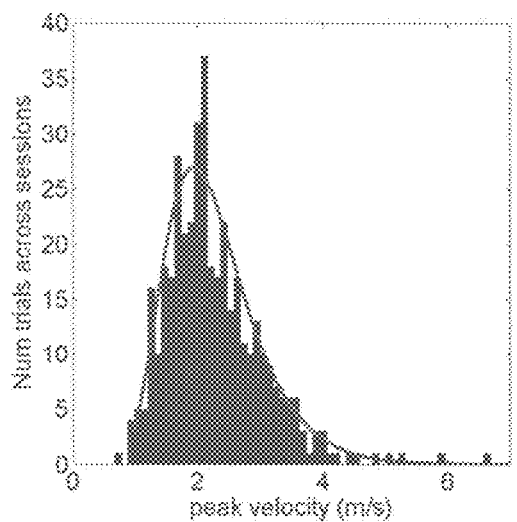

The distributions of the maximal speed values across repetitions and sessions turned out skewed (non-Gaussian) across TC subjects. They also differed between staged and incidental movements. In the typical system both the goal-directed and the incidental movements yielded distributions well fitted by the Gamma family. FIG. 13A through FIG. 13D show the histogram of the pooled data for the intended (staged) segments from all trials across sessions (see Analytical Methods for bin size determination). FIG. 13A refers to a TC (novice) and FIG. 13B refers to the ASD-case.

In the typical novices the distribution of the peak velocities was skewed. The log of the peak velocity yielded a normal distribution with maximum likelihood (m.l.e.) from a lognormal fit $\mu=0.76$ (2.14 m/s), $\sigma=0.32$ with 95% confidence intervals [0.69 0.83] and [0.28, 0.38] for the goal directed segments and $\mu=0.54$, $\sigma=0.29$ with 95% confidence intervals [0.47 0.60] and [0.26, 0.35] for the incidental segments. Parameters from a Gamma fit are also reported in FIG. 13A for the novice and in FIG. 13C for the entire set of 6 participants. Across subjects speed ranged between 0.97 and 7.91 m/s in the intended segments and between 0.60 and 4.96 m/s in the incidental segments incidental to the main techniques. The expert motions were significantly much faster (could reach up to 9 m/s).

Figure 13B:
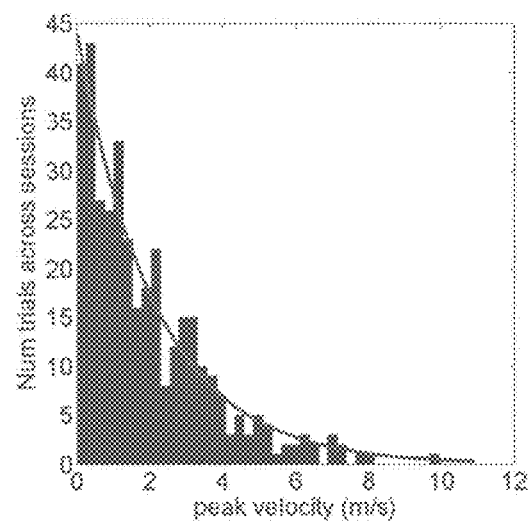
Figure 13C:
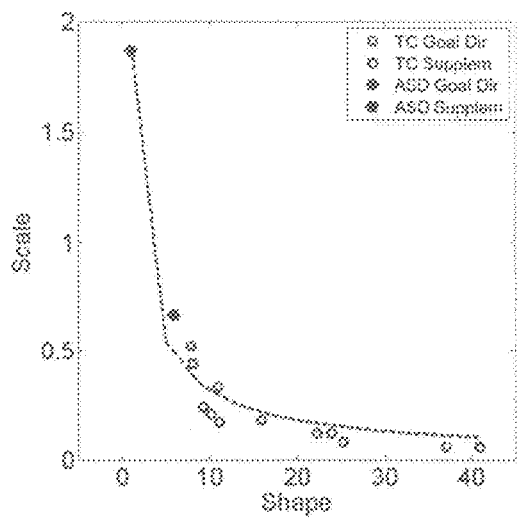
Figure 13D:
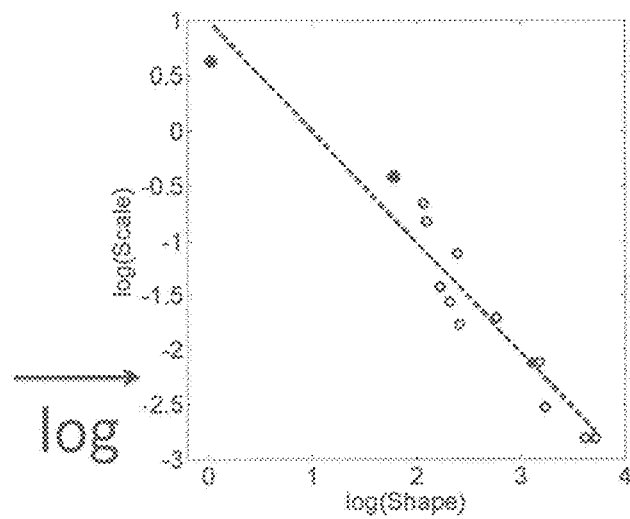

In the participant with ASD the staged movements across techniques, sessions and speeds yielded a distribution of peak velocities (m/s) well fitted by a Gamma in the exponential range. An exponential fit yielded m.l.e. $\mu=1.94$ and confidence intervals [1.76, 2.16]. This is shown in FIG. 13B. In the incidental movements from the retracting Jab m.l.e. from the Gamma fit was obtained with shape 5.93, scale 0.66, 95% confidence intervals [5.16 6.82] and [0.93 0.66] respectively. Notice in FIG. 13C that the supplemental movements of the ASD case were closer to those of the TC group. There is a significant gap between the Gamma fitting parameters of his goal directed and his supplemental segments even though the trajectories of these movements were connecting similar regions in space when striking forward and retracting back to the initial location. In FIG. 13C a power model yielded a good fit to the scatter and taking the log of the Gamma parameters in FIG. 13D showed a good linear fit. Notice also that most movements in the ASD case had low values and narrow variability across repeats and sessions.

It was found that the case with ASD had two striking features that differed fundamentally from the TC. First, the marked differences in TC between movement classes (intended goal-directed and spontaneous supplemental) were blurred in the system with ASD. Second, the system with ASD moved with high repeatability in a very deterministic fashion, lacking the natural dynamics fluctuations that were quantified in age-matched TC (including his sibling—who was as new to martial arts as he was). Both the lack of differentiation between intended and automatic motions and the exponential nature of the speed variability unveiled here in the case with ASD invite further inquiries into the physical movements of ASD sensory-motor systems. The inability to parse apart the goal-directed and the automatic portions of each technique in the ASD system suggest that his performance could not be solely attributed to cognitive impairments or his misunderstanding of the instructions to move. The spontaneous segments of the technique in particular were not directly instructed or voluntarily guided. They were rather spontaneous and incidentally supported the intended strikes of each technique.

The instructed changes in speed had similar consequential effects on the coexisting staged and incidental movements of the ASD case. An open question is whether his system can detect differences between goal-directed and spontaneous movements in general. Such differentiation typically manifests early in life when infants make a transition from spontaneous to goal-directed behavior (Smith and Thelen (1993) A Dynamic systems approach to development: applications, Cambridge, Mass.: MIT Press) unless there is early neurodevelopmental damage (Karmel and Gardner (2005) Ideggyogy Sz 58:315-323; Karmel et al. (2010) Pediatrics 126:457-467; Gargner et al. (1990) Dev. Psychol., 26:563-575) which in ASD and Asperguer's also coincides with delays in the evolution of reflexes (Teitelbaum et al. (2004) Proc. Natl. Acad. Sci., 101:11909-11914; Teitelbaum et al. (2002) J. Dev. Learn. Dis., 6:15).

The patterns of motor variability of this participant with ASD belong in a different statistical class from the TC. In particular his goal-directed motions were more mechanical and reliable than those of the TC. In contrast his supplemental movements were closer in Gamma parameter space to those of the TC. Since ASD is such a broad spectrum and the TC scatter showed a continuum in Gamma parameter space, the gap between the TC and the ASD case that was quantified here can be filled in as a continuum within a group of participants on the autism spectrum.

Example 5

Herein, it is investigated whether fundamental differences emerged between segments of complex movement sequences performed at different instructed speeds. To this end, 5 novices and 1 karate expert were tested as they performed beginner's martial arts routines. It was found that if one blindly took these segments and separated them according to the variability of trajectory parameters, one could unambiguously group two classes of movements between the same two space regions: one type that remained quite conserved despite speed changes and another type that changed with speed level. These groups corresponded to functionally different movements (strike segments explicitly directed to a set of goals and spontaneously retracting segments supplementing the goals). The curvature of the goal-directed segments remained quite conserved despite speed changes, yet the supplemental movements spanned families of trajectories with different curvature according to the speed. Likewise, the values of the hand's peak velocity across trials were more variable in supplemental segments, and for each participant, there were different statistical signatures of variability between the two movement classes. This dichotomy between coexisting movement classes of natural actions calls for a theoretical characterization. The present experimental results indicate that two separate sets of principles may govern these movement classes in complex natural behaviors, since under different dynamics the hand did not describe a unique family of trajectories between the same two points in the 3D space.

Herein, the possible differences between the effects that changes in dynamics may exert on the variability of hand trajectories described by complex sequential body motions that interleave staged and supplemental movements are investigated. To this end, segments in movement trajectories described by the hands during the performance of beginner's martial arts routines by a martial arts expert and 5 novice controls (NC) were used. Within these routines, there are strike and retracting movements. Strikes are staged segments corresponding to punches directed toward an imaginary opponent. Retracting segments are transitional untwisting movements co-occurring, as the system overtly focuses on staging another punch with the other hand. First, it was established that across subjects and for each participant (independent of expertise level) given a randomly selected trial it is possible to blindly group movements into two distinct classes and to predict with high accuracy what segment type and technique the trial most likely came from. To further establish specific separable aspects of each class according to the functionality of a movement within a technique, the statistical patterns of variability of several hand trajectory parameters was then evaluated in each participant.

Methods

Participants, Apparatus, and Behavioral Task—See Example 4

Determination of the Instantaneous Speed/Acceleration Profiles and Maxima

Movement trajectories were decomposed into the goal-directed and supplemental segments according to expert performance of the isolated techniques and of the techniques in sequence (J-C-H-U). Hand trajectories were decomposed into the staged and supplemental segments of each technique in the sequence. Instantaneous speed profiles corresponding to each segment were generated. To construct these profiles, the norm (length) of the velocity vector tangential to the curve described by the movements in each of the 3D hand trajectories was measured and the instantaneous speed scalar value was obtained. Each sub-segment of each technique had a maximum value which was determined along with the time at which this value was attained from the technique's movement onset. The hand velocity signaled movement at 5% of the maximum velocity value of the segment. Likewise, the sensors software directly outputs the acceleration vectors in 3D as well as their instantaneous norm to analyze the instantaneous acceleration profiles. The software also obtains their maximum scalar values for each sub-segment of the technique. Across all repetitions and sensory conditions, the histograms of these values was constructed to investigate the statistical properties of their frequency distributions.

Movement Classification—See Example 4
Statistical Analyses of Hand Trajectories in Three Dimensions—See Example 4 Distribution Analysis—See Example 4

The Gamma distribution is a two-parameter family of continuous probability distributions. Its probability density function is given by the expression:

$$y = f(x \mid \alpha, \beta) = \frac{1}{\beta^\alpha \Gamma(\alpha)} x^{\alpha-1} e^{-\frac{x}{\beta}}$$

with shape ($\alpha$) and scale ($\beta$) parameters. If $\alpha$ is a positive real number $\Gamma(\alpha) = \int_0^x t^{\alpha-1} e^{-t} dt$.

By varying the shape and scale parameters, one can go from a Gaussian-like distribution, which was found in typical-intact systems to the exponential distribution (when $\alpha=1$) which was have found in the compromised systems. Importantly, the distributions and different parameter values are differentiated solely by the statistical properties of empirical data (i.e., the velocity maximum in this case). The specific nature of a given statistical distribution allows probabilistic knowledge of what value the random variable (the maximum velocity here) will be in the next trial with different levels of certainty—with the exponential (the most random of the distributions) and the Gaussian distribution (needing only two moments to characterize the parameter's behavior) at the extremes. It is in this probabilistic context of certainty and predictability that the data has been framed to objectively assess the individuals' variability within the Gamma parameter (phase) space for the two movement types. Gamma parameters are thus expected to differ between the two types of movements for each participant. Furthermore, the expert's distance between the points corresponding to the 2 movement types in the Gamma phase space is expected to differ more than that of the novices—who are still learning these techniques.

Results
Randomly Chosen Trials can Predict which Technique and Movement Type the Trial Came from, Based on the Hand Trajectory's Maximum Bending The leave-one-out cross-validation procedure revealed that it was possible to accurately predict for a randomly chosen trial not only which technique the trial came from but also, without confusion, whether a given technique segment was from the strike portion or from the retracting portion. Using the maximum bending of the trajectory, the predictive value of the trials was high (0.83 for the strike and 0.99 for the transitional retracting ones). The results can be depicted in the form of confusion matrices for the group of subjects (A) and for the worst individual performance (B). Rows are actual values from the data sets. Columns are assigned values from the leave-one-out cross-validation algorithm using nearest-neighbor criterion. The 4 upper diagonal values represent the predictability level of each technique within the strike mode. The 4 lower diagonal values represent the same for the transitional retracting segments of each technique. Off-diagonal values within each mode (4-technique quadrant) indicate if there is confusion of one technique with another. Off-diagonal values in the 2-mode quadrants indicate if there is confusion of the type of mode.

Two main results stand out: (1) The retracting movements do a better job at distinguishing the techniques both for the group performance and for the individuals' performance; (2) The strikes of each technique (goal-directed segments) are never confused with the spontaneous retracting segments. Even for the worst individual's decoding performance, the distinction remains. Notably, the results from a population analysis including all 6 participants makes a statement about the overall variability in this group of people regarding these techniques and movement types, for the hand trajectories' maximum bending. The same analysis for each individual yielded a result that depended on the level of training. The expert had the highest predictive accuracy of technique-plus-movement type but one subject yielded 0.55 in the strike segments, 0.75 in the spontaneously retracting segments, and 0.65 mean diagonal. These values were still well above chance ($P \leq \frac{1}{8}$) yet much worse than the expert's (overall diagonal 0.85) and than other subjects who seemed to have learned at a faster rate. These disparate levels of decoding performance were expected. The surprise was how well the decoding algorithm captured the differences in movement types with no confusion between groups of movements even in the worst case. Even though the individual techniques within each movement type could be confused in most novices, the two movement types across all techniques were not confused. This clearly established two movement classes which corresponded to the strike and retracting portions of the techniques.

The learning/expertise stages of each individual and of the group were in congruence with the other analyses. The group's variability in the hand trajectories' maximum bending could accurately discern between movement types and technique, albeit with higher accuracy in the technique for the spontaneous transitional segments. In this sense, the spontaneous transitions were far more informative.

Different Effects of the Changes in Speed on Goal-Directed Versus Supplemental Segments Manifested in Expert and Novices Alike Given the results from the classifier—which unambiguously separated two groups of movements with different functionality—and that this separation corresponded to the goal-directed strike and the supplemental retracting segments of each technique, it was asked whether the instructed speed had differential effects on these two movement classes.

Across participants—despite levels of expertise—the trajectories from the supplemental (retracting) segments incidental to each technique divided into different families of trajectories according to the instructed speed. The trajectories from the supplemental segments changed their curvature with the speed. By marked contrast, the goal—directed trajectories maintained their geometric features despite different speeds. This result was congruent with the decoder, which for each individual and also as a group showed better predictive value for the spontaneous transitions interleaving the goal-directed strikes.

Speed profiles and the corresponding 3D trajectories from the expert performance of the full fluid sequence across 20 trials were also determined. The supplemental spontaneous trajectories from the Hook (H2) and from the Uppercut (U2) as the system transitioned to other staged technique with the opposite hand. These trajectories dramatically changed with the speed and grouped into different families of curves even though they were preceded by the goal-directed curves, the strike segments of each technique that had preserved their geometric features (bending and orientation) despite speed changes.

With regard to the performance of a typical novice, the effects of speed were different in the staged segments (the trajectories are more conserved) than in the supplemental segments of the technique (the trajectories changed), albeit with more variability than the expert's motions. In each technique for the novice, the trajectories from the goal-directed segments remained similar despite changes in speed ($\Lambda > \Lambda^*$) for each point along the path, but the corresponding supplemental trajectories split according to speed type ($\Lambda \ll \Lambda^*$). This was the case particularly for the highly curved movements (Hook and Uppercut). As in the expert performance, the novices' performance conserved the goal-directed curves but the supplemental trajectories changed according to speed type. These effects were congruent across subjects and consistent in other parameters of the hand trajectories—as described later.

The decoder's blind distinction between strike and retracting motions of each technique had a correspondence with the effects of instructed speed on the hand trajectories of each movement type. The supplemental motions of each technique had systematically higher predictive value across subjects and for the group—since different families of trajectories for each technique emerged with changes in speed. Their patterns of variability not only changed significantly, they actually split into different families of trajectories.

In the strike segments specifically aimed at a set of goals, the decoder's prediction showed more confusion for each subjects and for the group than the supplemental segments. In the goal-directed trajectories, there was more conservation and less variability. In this sense, their bending patterns across speeds were less informative. Next, the temporal coverings of these curves were examined and the statistical patterns of variability of the maximum hand velocity along each technique's segment were assessed.

Skewed Distributions of the Peak Velocity Values from the Hand Trajectories

The distributions of the maximal speed values across repetitions and techniques were skewed across subjects with different degrees of skew well fitted by the continuous 2-parameter Gamma family. In both goal-directed and supplemental cases, taking the logarithm of the peak velocity turned the distributions normal. Across novices, the hand speed ranged between 0.97 and 7.91 m s$^{-1}$ in the goal-directed segments and between 0.60 and 4.96 m s$^{-1}$ in the supplemental segments incidental to the main techniques. The expert motions were significantly faster (up to 9 m s$^{-1}$). They also differed between staged and supplemental movements in the Gamma parameter (phase) space. This is shown across all subjects with the power fit, goodness of fit values reported in the figure caption (absolute value of the exponent for goal-directed 0.93 was below 1, but above 1 (1.64) for supplemental motions and maximal separation between the 2 m.l.e. sets of parameters for the expert). The goodness of fit was best in the supplemental movements as well. These results were congruent with the decoder's and with the different patterns of trajectory variability for the two movement types of each technique.

This work investigated patterns of movement variability during the performance of complex beginner's martial arts routines. First, it was shown that across repeats of these complex sequences and for this group of participants, one could randomly choose a trial and predict with high accuracy the type of technique and segment functionality that the randomly chosen trial most likely came from. Based on the maximum bending of the hand trajectory, a simple linear classifier did not confuse which strike and technique a blindly chosen trial came from. These separable movements also had different purposes. The strike segments corresponded to staged segments performed toward a goal (e.g., hit the face area of an imaginary opponent). The transitional retracting movements supplemented the main goals. A main hypothesis is posed in this work: speed changes will have a different effect on the movement trajectories of the goal-directed segments than on those from the supplemental segments, incidental to each staged technique, with marked differences in their statistical patterns of variability.

The evidence supports this hypothesis. There are two fundamentally different classes of movements to be simultaneously controlled, serving different functions. The instructed changes in speed affected their trajectories differently. These effects were quantified in the maximum bending and in the maximum speed of the trajectories from both movement types. The class of movement explicitly subserving a set of goals (goal-directed) tended to conserve the physical curves of the trajectories and had different latencies and different temporal profiles. The supplemental class of movements manifested different trajectories—each corresponding to a speed level (i.e., to a given latency and temporal profile family).

These findings held independent of the level of training or skill of the participant. The different instructed speeds in the expert and novices alike had a fundamentally different effect on the movement segments that were staged and deliberately aimed toward a goal than the effects they had on the supplemental transitions of each technique. Specifically, when moving the hand between the same two locations in space, the system made different uses of the sensory input provided by the movement (i.e., from the kinesthetic sense of body position and body movement) when the motion was goal-directed than when it was supplemental. When instructed to move faster, the system scaled the tempo of the movement along a statistically similar physical path if the motion was staged to punch the opponent. When retracting the hand as the other hand simultaneously deployed the next punch, the retracting path to the same initial spatial location spanned a significantly different physical trajectory for different instructed speeds. Each speed level spanned curves with a distinct geometry: different path length, different curvature, different orientation, etc. Likewise, there was a gradient of variability in the speed parameters that differed between the two blindly separated groups of movements. Specifically, the values of the maximum speed along the hand trajectories manifested two distinct signatures of variability according to the Gamma-distribution family's m.l.e. These signatures were different for each subject and had different values for the strike than for the retracting segments. The two movement types were at a larger distance in the Gamma-distribution parameter space in the expert's case compared to novices. This suggests that the more the system practices, the farther apart the statistical signatures of variability from these two movement types may become.

Skewed distributions of the peak velocity not previously reported in complex sequences were also found. These new findings in complex sequential motions performed by humans paired with the finding that the log of the parameter distributes normally may be of interest to the computational community. There are fundamental statistical differences between symmetric and skewed distributions in terms of additive versus multiplicative effects (Limpert et al. (2001) Bioscience 51:341-352). Both the log-normal and the Gamma family provided good fits to the kinematics data. These results invite investigation of the statistical patterns of variability from other movement variables and their roles as task-dependent control parameters in stochastic models of optimization with constraints.

The present results have therapeutic value in clinical research. Here, in more complex sequential movements, this dichotomy between task-relevant and task-incidental aspects of the movements was used to identify in the patterns of movement variability the most adequate movement-based feedback to guide a system. This turned out to be from the supplemental movements. Using the present objective metrics, one will be able to track learning gains in patients.

The ability to track learning gains in patients to identify the most effective form of sensory-motor feedback for a given individual can facilitate the identification of relevant movement parameters to tailor personalized therapies that exploit the best learning predispositions and the best sensory capabilities of each given individual. In this sense, the present methodology may be used in spectral developmental disorders—such as Autism—and in spectral neurodegenerative disorders as well—such as Parkinson's disease. Both disorders—whether present at the beginning or at the end of the human lifespan—produce a constellation of sensory-motor deficits with variable degrees of severity from individual to individual. Thus (all things being equal in a task), the personalized signature of motor variability (e.g., the Gamma parameterization of variability providing a continuum of signatures across subjects) can indicate where the individual falls in relation to typical controls along a continuum gradient of variability for each movement type. In turn, this can indicate which form of sensory-motor feedback could potentially be more suitable for a given patient within a given spectrum. Additionally, since supplemental movements are a by-product of or support goal-directed behaviors, they require no explicit instructions. This is advantageous since the majority of the patient populations from whom one can assess naturalistic movements may have difficulties following precise instructions. Thus, one could target these spontaneous supplemental motions to track performance gains.

The conservation versus non-conservation of the movement trajectories with speed changes can have implications for theoretical work in movement control. Two qualitatively different solutions emerged to move between the same two regions of space: one which gave rise to a unique curve with multiple temporal profiles and latencies (goal-directed case) and another (supplemental case) which gave rise to different families of curves, each one of which had a unique temporal profile and latency.

Example 6

Materials and Methods
Collecting the Deliberate-Intended and the Automatic-Unintended Segments—See Examples 4 and 5
Distributional Analyses—See Examples 4 and 5
Data Extraction Position data were directly obtained from the electromagnetic sensors and first-order (velocity) changes in position over time obtained using the smoothing and derivative functions from the Spline toolbox in Matlab. For each trajectory the instantaneous length of the velocity vectors was obtained using the Euclidean norm. The values of velocity maxima were computed and 5% of the peak velocity used as a cutoff to separate pauses from movement and to delineate movement segments. Two movement types were examined:

1. Intended-deliberate movements (those aimed at the target) began from some position, were directed to the target region and culminated on a screen touch of one of the 2-targets of choice. The screen touch at the target was logged and time-stamped. Backtracking from the stop at the touch screen point to the first full stop yielded the goal-directed, deliberate segment.

2. Unintended-automatic movements began immediately after the screen touch, were not directed toward any specific goal, and consisted of the spontaneous retracting arm movements supplementing the main goal-directed component of the pointing behavior. Tracking the trajectory from the screen touch on to the next full stop determined the automatic segment.

Importantly, the children controlled the flow of the experiment as they advanced to the next trial by touching the screen only after they made a decision. There was no time constraint to perform the task. This self-paced style was germane to all children but it was particularly relevant in order to keep the low-functioning non-verbal children with ASD fully engaged in the task.

Instantaneous velocity profiles were calculated from the hand trajectories as well as relevant parameters that vary across repetitions as each movement unfolds. These included the absolute maximum speed value and the % of movement time to reach this peak velocity in each of deliberate and automatic segment types of the TD, ASDI, and ASDII participants detailed in the next section. FIG. 1 shows the hand trajectories from a typical session and the flow of the trajectories from two representative children in the study. Movement trajectories are rich in parameters that reveal the variability of the motor system, yet the relevance of each parameter is task dependent. A common analysis performed in the motor control literature is on the endpoint variability of reaches (van Beers et al. (2004) J. Neurophysiol., 91:1050-1063; Harris et al. (1998) Nature 394:780-784). Although the scatter of endpoints around the target provides an important source of information in tasks that require precise pointing accuracy, the present task did not have such a constraint. Rather, the goal was to match to the given sample a target that took up a broad region of the touch screen. This was a two-choice decision-making task with a systematically manipulated cognitive component. Such manipulations affected cognitive parameters—decision-making time and % correct choice, to be reported later—that evolved in parallel with the motor learning. Herein, it is addressed how the maximum speed of movements was altered by variable cognitive loads. In the context of natural behavior, such as those assessed in the present task, the variability of the dynamically unfolding curve (the distance traveled by the hand within a time period) for the instant purposes is far more informative than the variability of a single static point at the end of the reach.

Another important aspect of the analyses is the number of samples and the unit-time relevant to the parameters of interest. The time to attain the peak velocity was on average in the order of 100-200 ms and each of the trials took on the order of 15,000-20,000 ms to be completed. These included the time to make the decision and the movement time. The latter took on the order of 1000 ms for each of the deliberate and the automatic segments. The tests took 15-20 minutes (1,200,000 ms) each session and the experiments were conducted in the course of 12 sessions per child. Across days over 2,500 trials were gathered per subject which densely sampled the space of interest for each subject and generally captured the underlying phenomena across each of the subpopulations of interest. This can also be appreciated in the goodness of fit of the regression with $R^2=0.98$ and $rmse=10^{-3}$. As is known in Statistical Ergodic theory, doing averages over long periods of time gives statistically equivalent results to those obtained by doing averages over an ensembles of samples; in this case humans subjects are equivalent to members of an ensemble.

In order to assess cognitive learning and changes in Gamma-space movement parameters over time, trials were categorized from being multimodal or unimodal. Trials were multimodal if they consisted of multiple velocity peaks and smooth troughs with no full stops from the start of the movement to the target location in deliberate-intended segments, and from the target location back to the resting position, for automatic-unintended segments. FIG. 3C and FIG. 3D show examples of multimodal peaks and of the resulting unimodal trials with a single peak re-acquired upon practice. Importantly, the % of trials with two, three, four and five peaks, was quantified in each group for multimodal trials. Additionally, the % of multimodal trials in which the absolute maximum speed (as opposed to a local speed maximum) occurred at the first peak was quantified.

Assessing the Cognitive and Motor Learning Progressions in Parallel

It was first established that there was an increase in the cognitive load and then the systematic effects were assessed in tandem with this systematic increase on the motor learning that was quantified in the speed profiles. Color, shape, or rotation are sample stimuli used to manipulate the cognitive load.

Cognitive Learning: The higher complexity in the stimuli increased the cognitive load of the task. To show this the evolution of 2 parameters was examined in each experimental block: the % correct choices and the decision time. The % correct-choices is the number of correct matches out of the total number of trials in each block. The decision time is the time from the stimulus onset (when the hand touched the start button on the screen) until the hand touched the screen at the target.

$$\text{Total Decision Time} = \text{cognitive decision} + \text{movement decision} \quad (1)$$

The cognitive decision time in (1) is from the stimulus onset to the movement onset. The movement decision in (1) is from the movement onset to the stop of the movement at the target (the screen touch). This is the duration of the movement.

It was hypothesized that if the cognitive load systematically increased from color discrimination to shape discrimination to mental rotation, then the total decision time (1) would also increase in that order. This contributed increase would be by both the increase in the cognitive decision and in the movement time. Likewise, it was hypothesized that the % correct-choice would decrease as the complexity of the task increased (i.e. there would be more errors in the task that required mental rotation than in the simpler color discrimination task). Evidence was found supporting both hypotheses. Table 2 lists the means and standard deviations for both Gamma-parameters as well as the means and standard deviations of the reduction in the decision time across trials and longitudinally for each task as the children learned.

TABLE 2

Systematic changes in cognitive performance occurring in parallel with motor (speed) learning.

|  | Color Mean (SD) | Shape Mean (SD) | Orientation Mean (SD) |
| --- | --- | --- | --- |
| Percent Correct | .96 (.21) | .92 (.27) | .82 (.38) |
| Decision Time (ms) | 2730.0 (2823.3) | 3260.8 (2814.9) | 3673.5 (4313.8) |

TABLE 2-continued

Systematic changes in cognitive performance occurring in parallel with motor (speed) learning.

|  | Color Mean (SD) | Shape Mean (SD) | Orientation Mean (SD) |
| --- | --- | --- | --- |
| DT reduction (ms) | 1190.7 (2618.2) | 822.1 (2011.9) | 1126.8 (4159.8) |
| P-value Dt reduction | .0001 | .001 | .03 |

It is important to note that the contribution of the movement decision time to the overall decision time was nearly constant in each child once the speed became unimodal after movement practice. The practice of the movement registered significant reductions in the movement time for each child group (rank sum test, p<0.05). The median reductions ranges for each group were TD (0.51, 0.70) s, ASDI (0.52, 0.85) s and ASDII (0.57, 0.78) s. This quantity subtracted from the total decision time yields the cognitive decision time. Contributions to the overall reduction of the total decision time once the speed is unimodal and stable (low variability in the movement time) are made by reductions in the cognitive decision time. This was the time elapsed from the presentation of the stimulus, which were time stamped with the touch at the start button on the screen, to movement onset, which could be extracted from the hand speed profile because it was time stamped and all behavioral events were logged including the target touch on the screen. Thus one could align the physical stop of the hand motion speed to the physical target location on the monitor, and to the corresponding pixel-area of the target stimulus on the screen, all synchronously timed by the same CPU. Pair-wise significant differences was found between TD and ASDI (p<0.002, X2=9.32) and ASDI-ASDII (p<0.05, X2=3.07) but not between ASDI and ASDII (p<0.19, X2=1.71).

Along with the reductions in the cognitive decision time, $F(2, 4636) = 28.67$, $p < 0.001$, there were corresponding increases in choice-accuracy as measured by the percent correct, $F(2, 4636) = 83.04$, $p < 0.0001$. As indicated by post-hoc tests, each group was significantly different from each other group for both measures. Besides improving daily, the children improved their overall performance longitudinally as evidenced by a significant reduction in the decision time with practice once the speed profile became unimodal and the movement duration was steady. As the speed profiles evolved to the unimodal signature of well-practiced reaches so did their cognitive proficiency at the task. There were systematic opposite effects in the increase in % of choice-accuracy with the increase in cognitive load: The higher the complexity of the stimulus the lower its %-gain. The children overall made fewer errors and took less time to make the cognitive decision as they practiced the task and transitioned from multimodal to unimodal speed profiles ($\chi2=21.18$, p<0.0007 cognitive conditions of color, shape, and mental-rotation compared pair-wise in each child type between early multimodal and late unimodal speeds). The most important result here was that in the children with ASD these signs of improvement in cognition were detected in their automatic retracting movements rather than in their deliberate movements.

Motor Learning: In the motor learning domain which occurred in parallel with the cognitive learning the cognitive-dependent effects were also assessed. Equation (2) describes the main cognitive-dependent components of the movement decision term in (1):

Movement decision=Time to peak velocity+remaining movement time (2)

Recall that the movement decision component in (1) is from the onset of the movement to the stop at the target, which were time-stamped by the screen touches. After the movement onset marked by an increase in speed above 5% of the speed maximum, the portion of the movement that is closest to the pre-movement cognitive decision in (1) is within the time to reach the peak velocity. This is a space-position dependent quantity subject to systematic changes across space with cognitive complexity (Torres et al. (2006) J. Neurophysiol., 96:2613-2632; Torres, E. B. (2010) Behav. Brain Funct., 6:21; Torres et al. (2010) J. Neurophysiol., 104:2375-2388). The remaining movement time in (2) is subject to feedback error correction, which depends on the evolution of the preceding cognitive-dependent time to peak velocity and on the ongoing motion. It was important to precisely quantify the number of peaks and the time to the first peak. This was particularly relevant to (2) when the maximum velocity was at the first peak.

Within each deliberate and automatic trajectory, the frequency of the number of velocity peaks was quantified per trial in each participant and pooled across all participants in a group to characterize the overall patterns of random fluctuations of the evolutions of the speed parameters in each group. It was determined if each group manifested a different frequency of such multimodal speed profiles during the learning progression. The frequency of occurrences of the absolute global speed maximum at the first peak was also quantified and the time to attain it.

To objectively quantify individual statistical signatures of speed variability across tasks in relation to the expression (2) the patterns of random fluctuations were examined in the values of the velocity peaks and of the time to reach the peak for each child across all trials. Since these movements were not time-constrained, they had a variable duration. Each child selected their own pace. Therefore the % of time to the peak velocity per movement segment was measured. To this end for each child the total duration of each individual deliberate and automatic trial segment was obtained. For each trial and segment the time to reach the peak velocity was measured and divided it by the total duration of the segment.

Results from the Evolution of the Cognitive-Dependent Motor Learning to Re-Acquire the Unimodal Profiles after Movement Onset The examination of the number of peaks per trial in each group revealed differences between the TD children and the children in the ASDI group who were close in chronological age. However, the older children in the ASDII group had similar patterns as those of the TD. In the learning progression of deliberate movement segments 78% of the TD trials had two peaks as opposed to 56% in ASDI. The frequency of two peak trials in the TD group was close to the ASDII which had a two-peak frequency of 80%. However, the reason why TD had more two-peak trials than ASD1 was that, the number of three peak trials was twice as frequent in ASDI (32%) than in TD (16%). TD pattern of three-peak trials was comparable to ASDII (17%). Likewise, four-peak trials were more than twice as common in ASDI (11% ASDI vs. 4% TD) and ASDII had 1%. Five-peak movements were seldom observed (2% in TD, 1% in ASDI and 2% in ASDII). The automatic movements had comparable percentages. These results indicate that the rate of cognitive-dependent learning was faster in the TD and ASDII groups than in the ASD I group.

Besides the frequencies of the number of local speed maxima per group, the frequency with which the first peak was the absolute global maximum was also measured. The locations over trials of the absolute global maximum in space and in time play an important role in the decision trajectory after movement onset. As any other cognitive process, decision-making can be characterized by two types of processes: fast-intuitive-automatic and slow-deliberate-intentional. The deliberate movement-decision can be assessed as the movement unfolds towards the target. A steady initial speed profile can be indicative of more certainty in the deliberate-slower-unfolding decision which is concurrently taking place with the hand movement. It was hypothesized that multiple local maxima before attaining the absolute global maximum would suggest hesitation in the initial phase of the otherwise familiar pointing act. As the movement becomes well-practiced, and the system has visited all possible choice-scenarios and learned to decide quickly, the fast-automatic intuitive decision process takes over. The % correct-choice increases and the cognitive decision time in the initial portion of the reach, which is embedded in the total movement time of (2), decreases. The speed profile becomes unimodal indicating a highly automated and well-practiced (re-acquired) pointing task where the cognitive choices have been correctly learned. Evidence was found in support of this hypothesis and analyzed within each child type the progression of the deliberate learning and that of the spontaneous learning that took place without specific instructions in the automatic retracting motions.

In the deliberate segments there was a higher frequency of first peak absolute maxima for the TD (76%) and ASDII (74%) groups, than the ASDI group (65%). In the automatic retracting segments the three groups had comparable frequencies of the absolute maximum being the first of multiple peaks, thus indicating more similarities across groups in these types of automatic movements than in the deliberate ones (TD 78%, ASDI 74%, ASDII 77%). This result was congruent with the stochastic signatures uncovered across groups and individually. The automatic motions of the children with ASD were closer in the Gamma plane to those of the TD children than the deliberate movements were. During the learning process in the TD and ASDII groups the local speed maxima were present mainly in the deceleration phase of the reach during the deliberate segments; whereas, the ASDI group had overall more variability in the initiation of the automatic retraction.

The medians and ranges of the values of Peak Velocity, Time to Peak Velocity, Overall Movement Time and % of Total Time to Peak Velocity for the deliberate movements of each of the three types of match-to-sample tasks were determined. The same values for automatic movements were also determined. In general, there was a tendency for these parameters to change with the incremental increase in the cognitive demands of the tasks. For example as task difficulty increased, the velocity of deliberate reaches and that of automatic reaches decreased ($\chi2=8.39$, $p<0.015$; $\chi2=11.88$, $p<0.003$) and the movements took longer ($\chi2=13.92$, $p<0.001$; $\chi2=34.98$, $p<0.001$). Both the TD children and the children with ASD showed these effects of having to adjust to the cognitive demands of the task. However the extent of these effects was significantly different in another measure (the speed-area ratios) across TD and ASD groups.

Additional Metric of Motor Learning: The Area Speed Ratio

To quantify any systematic effects of the differing cognitive loads on the speed profiles the area under the speed curve up to the speed maximum (acceleration phase) was measured and divided by the total area under the speed curve, thus producing a speed-area ratio. When the speed-area ratio equals ½ the speed profile is symmetric in time. It takes the same amount of time to accelerate and reach the maximum speed as it takes to decelerate and stop at the target. This is the well known "bell shaped" speed profile observed in well-practiced point-to-point movements (Abend et al. (1982) Brain 105:331-348; Morasso, P. (1983) Biol. Cybern., 48:187-194). When the area-speed ratio is <½ it means that the acceleration phase is shorter than the deceleration phase—either as a steady increase in speed up to the maximum speed or with some slowing down-speeding-up additional local peaks before attaining the global maximum. These types of skewed profiles have been reported in non-human primates during highly curved reaches to avoid physical obstacles in three dimensions. Another possibility is that the speed-area-ratio is >½ in which case the acceleration phase is longer than the deceleration phase. This type of skewed speed profile prevails in orientation-matching during reach-to-grasp experimental tasks in three dimensions that require mental rotation.

Results from the Analyses of the Speed-Area Ratio: Task Complexity Modulates the Speed-Area Ratio The skewness in the time to reach peak velocity gradually increased with task complexity. The analyses revealed a prevalence of symmetric profiles with speed-area ratios in the ½ range during the (simpler) color discrimination task, and more skewed profiles due to larger areas under the speed curve during the acceleration than the deceleration periods. Skewed profiles were more prevalent in the more complex tasks. The monotonically decreasing trend in the change of the speed area ratio was present in the TD population for the deliberate segments and was inverted for the automatic segments. By marked contrast this monotonic trend was absent from both ASD groups.

The systematic effects of cognitive load on the ratios were significantly different between the TD children and the children with ASD from both groups, (Kruskal-Wallis test, $\chi 2=18.07$, $p<0.001$). In the TD cases the trend could be explained by a systematic increase in the time to reach the peak velocity from the color to the shape to the condition that demanded mental rotation. Post Hoc analysis (rank sum test) revealed the largest effect between color and mental rotation conditions ($p<0.0001$, z-value 2.61). The more difficult the task stimulus, the longer it took to reach the peak velocity, resulting in increasingly skewed speed profiles with systematically longer initiation segments—a systematic increase in the acceleration phase and a decrease in the deceleration time. These trends explained the significantly lowered values in the speed-ratios for the stimulus that required mental rotation (ratios <½) (a prevalence of shorter deceleration than acceleration areas under the curve) as compared to the simpler color discrimination stimulus that resulted in ratios close to ½ (with ratios for the shape condition somewhere in between).

In the case of automatic movements, the TD children showed a reversed effect (as compared to the deliberate movements) on the ratios with a monotonic increment from color to rotation conditions. In these movements the effect was also significant (Kruskal-Wallis test, $\chi 2=9.17$, $p<0.01$) with the largest difference between color and mental rotation conditions ($p<10-5$, z-value $-4.27$). When moving away from the touch screen they reached the peak velocity significantly faster in the more difficult conditions (shape and rotation) than in the simpler color-discrimination task. Consistently the ratios monotonically increased with the increase in task complexity.

In the ASDI group, the trend observed in the TD children was absent during deliberate movements (Kruskal-Wallis test, $\chi 2=2.33$, $p=0.32$) and also absent in the automatic movements (Kruskal-Wallis test, $\chi 2=3.35$, $p=0.19$). The trend present in the TD group was also absent from the hand movements of the children in the ASDII group during the deliberate segments (Kruskal-Wallis test, $\chi 2=3.46$, $p=0.18$) yet the effect was significant at the 0.05 level during the automatic segments (Kruskal-Wallis test, $\chi 2=6.40$, $p=0.04$). Task complexity did significantly modulate the speed profiles of the movements of the children with ASD (inducing a transition from multi- to uni-modal as in the TD children) but in the deliberate segments the specificity of the effects could not be discriminated as a function of the type of stimulus, as in the TD group. In other words, the deliberate segments' speed area ratios in ASD could not tell one whether the task involved color discrimination or mental rotation, but these ratios could do so in the TD group. The parameter was also more informative in ASD when the automatic segments were examined. This feature of the ASD automatic motions was further examined. To do so a parameter related to the area speed ratios—the time was used to reach the peak velocity. As it turns out during the automatic segments the time to peak velocity provided critical information that helped to accurately discriminate the stimulus type that a randomly chosen automatic trial came from across all three groups.

Time to peak velocity is a good predictor of the stimulus trial type of both movement classes in TD but only of the automatic movement class in ASD Dramatic differences in the time to reach the velocity peak between TD and ASD cases were found. These trends generalized to all other children and were amenable to further investigate systematic effects of the cognitive load on the movement speed. The time to the peak velocity is directly related to the speed-area ratio as it determines the maximum value of the velocity and influences the value of the numerator in the ratio.

For the analyses from each movement type (deliberate or automatic) the trials from each group of children (TD, ASDI and ASDII) were merged and the time to peak velocity of a trajectory was used as input to the decoding algorithm in order to predict the stimulus type. For each stimulus type 150 trials (the minimum number of trials collected from one child for one stimulus type) were used in any given condition (for a total of 450 trials per movement type). Three stimulus types were used: color, shape and rotation.

Trials were represented as points in an m-dimensional space, each coordinate corresponding to the number of milliseconds to reach the absolute maximum value of the speed, for each of the m children in a group (TD m=5, ASDI m=5, ASDII m=6). One at a time, data from each trial picked at random was used to predict the stimulus' time to peak velocity, based on distributions derived from all remaining trials (leave-one-out cross validation) and was assigned to the class of its nearest neighbor in the m-dimensional space using Euclidean distance. For assessing statistical significance of the decoding results, a value of 1 was assigned to correctly predicted trials and a value of 0 to the incorrectly predicted ones. The mean of the sequences of correctly and incorrectly classified trials were compared statistically using a non-parametric Wilcoxon rank test and represented graphically as confusion matrices.

Decoding Results

The confusion matrices revealed results consistent with those from the statistics of the speed-area ratios. In the TD children it was possible to predict which stimulus type a randomly chosen trial came from: whether it came from the color, shape, or rotation set. The accuracy level of the decoder was well above chance (0.64>0.33) when taken all three stimuli per movement segment type and even higher (0.88>0.5) when predicting the type of movement segment (deliberate vs. automatic) for each stimulus type. In the TD group the decoder did not confuse color with shape or rotation, for the two movement types, deliberate and automatic. By marked contrast the trials from the ASDI and the ASDII groups had lower predictive value and there was confusion in the deliberate cases. Interestingly their automatic movements showed better predictive value than their deliberate ones. This was a result consistent with the Gamma-distributional analysis.

The results from the linear decoder were also consistent with the statistics of other temporal parameters from the hand trajectories. However, of all parameters the time to peak velocity was the most informative about the stimulus type that a randomly picked trial most likely came from. Other related trajectory parameters used as input to the decoder were used. These were the values of the Peak Velocity, the Overall Movement Time and the % of Total Time to Peak Velocity. The same values were determined for the automatic movements. In general as movements shifted from multi-modal to unimodal speed profiles there was a tendency for deliberate and automatic movement time to decrease ($\chi2=118.44$, $p<0.001$; $\chi2=26.28$, $p<0.01$) and movement velocity to increase ($\chi2=588.71$, $p<0.001$; $\chi2=487.13$, $p<0.001$).

The differential effects in stimulus type based on movement type (deliberate vs. automatic) were best evidenced in the time to peak velocity. The time to peak velocity was the most informative parameter to predict from which stimulus type a trial most likely came and whether the trial was from a deliberate segment or from an automatic segment. This was not surprising in the TD children given the marked differences in frequency distribution between deliberate (normal) and automatic segments (highly skewed). In the children with ASD the predictive power was higher in the automatic movements than in the deliberate ones. This result was congruent with the results from the Gamma plane for one child, which extended to other children. It was also evident in the results from the Gamma plane analyses of the groups. The automatic motions of the children with ASD were, in general, closer in proximity to those of the TD children than the deliberate ones.

The improvements in motor performance paralleled faster decision-making and fewer errors in their choice-discrimination (FIG. 14A). This cognitive development took place concurrently in the intended and in the unintended-automatic segments. While the intended segments were informative of children's deliberate cognitive learning, their automatic ones informed of their intuitive cognitive learning (Senju et al., Science 325:883-885). The stochastic signatures of speed variability in both movement types were reshaped in each group (FIG. 14B). Notably during spontaneous learning the stochastic signatures of the children with ASD shifted with a faster rate towards the TD regime than during the deliberate learning. This could also be appreciated in their individual learning trajectories in the Gamma (a,b) plane. There the connected paths are plotted across conditions for each individual child: baseline-unimodal, multimodal-learning and well-practiced unimodal (FIG. 14C). These cognitive-dependent motor manipulations gave rise to different learning rates for each child. This was clearly captured by the new objective metrics introduced here, both individually and as a group.

It has been shown that by reshaping the conscious-deliberate and the unconscious-automatic movement types one can influence cognitive performance and change the course of learning very precisely in both TD children and in children with ASD. Through movement practice the children became more accurate and faster at their decision-making performance with marked individual differences. Likewise by varying the cognitive load of the task, their movements, both intended and automatic, can be reshaped in closed loop with deliberate and intuitive cognition. By bridging cognition and movements in this way, and providing personalized objective metrics of performance gains, one can individually tailor therapies to better exploit the sensory capabilities and the learning predisposition of each child. One can also monitor the learning trajectories of both individuals and of groups. It has been shown that automatic-unintended movements provide the means to objectively quantify changes in a type of intuitive cognitive learning that occurs beyond one's awareness. This quantification is independent of deductive inferences, and works even when the children are non-verbal, and labeled as "low-functioning" ASD.

Example 7

Current diagnosis of Autism Spectrum Disorder (ASD) (American Psychiatric Association (2000) Diagnostic and statistical manual of mental disorders: DSM-IV-TR, 4th Ed. Washington, D.C.: Amer. Psych. Assoc.) does not make provisions to distinguish between boys and girls despite known gender differences in typical developmental trajectories across a broad range of parameters, from physiological to cognitive milestones, including language. Typically-developing boys are known to generally lag behind girls initially, but eventually boys catch up (Stromswold, K. (1998) Hum. Biol., 70:297-324) and, by adulthood, some gender differences in reaction time (RT) may emerge whereby males are reportedly faster (Adam et al. (1999) Ergonomics 42:327-335; Der et al. (2006) Psychol. Aging 21:62-73), suggesting parallel learning paths.

In children who have already been diagnosed with ASD, girls, particularly those without marked cognitive impairments, may have been formally identified at a later age than boys, which may have impeded referral for early interventions (Giarelli et al. (2010) Disabil. Health J., 3:107-116). From this, it seems important to develop non-invasive tests related to cognitive performance (e.g., decision-making tasks) that can be easily administered in clinical settings with minimal intrusion to identify possible systematic gender differences across children of different ages. This information would be extremely valuable given its implications for the correct standardization of gender-based cognitive metrics, the fact that the diagnosis of ASD is centered at cognitive impairments (ADOS (Berument et al. (1999) Br. J. Psychiatry 175:444-451); GARS-2 (Campbell, J. M. (2005) J. Autism Dev. Disord., 35:25-35; Lecavalier, L. (2005) J. Autism Dev. Disord., 35:795-805)) and the observation that there is a large gender difference in the prevalence of ASD—approximately 4.3:1 boys to girls (Newschaffer et al. (2007) Annu. Rev. Public Health 28:235-258). Besides correcting for potential gender bias in the timing of diagnosis to allow for earlier interventions for girls, it is important to understand gender differences when designing educational curricula, since many of the general cognitive deficits in ASD relate to decision-making processes and executive function (Ozonoff et al. (1991) J. Child Psychol. Psychiatry 32:1081-1105).

Used since the mid-nineteenth century, mental chronometry—the analysis of reaction time and response time—has become the cognitive metric of choice to index task complexity, task difficulty, and the efficiency and speed of cognitive processing. Although gender differences in RT have been well-documented in typically-developing populations, little is known about their presence (or absence) in ASD. Furthermore, gender differences in brain development have been used to anchor cognitive theories of ASD (Baron-Cohen, S. (2002) Trends Cogn. Sci., 6:248-254; Baron-Cohen et al. (2003) Philos Trans R Soc Lond B Biol Sci., 358:361-374) with support obtained from self-report surveys, inventories and meta-analyses (Lai et al. (2011) PLoS One 6:e20835), but no operational definition has been provided that permits fast and automatic objective assessments of gender differentiation in clinical settings or in the classroom environments within 10-15 minute time windows, and with minimal disruptions of the children's daily schedules.

This work introduces a simple computerized-task adapted from a curricular activity in natural classroom settings that permits rapid identification of gender-differences during the performance of a decision-making task. Broad gender- and cognitive-performance differences in ASD are highlighted in relation to typically-developing peers.

Materials and Methods

Participants

Informed consent was obtained from the parents of all participants. All experiments were conducted according to the principles expressed in the Declaration of Helsinki. Twenty-nine children (11 female, 18 male) participated in the study. Children were divided into three groups. 13 children (6 female, 7 male, M=4.2 years (range=3.4-5.2 years)) in the TD group were of typical-development and had no history of developmental delays of any kind. Children with ASD were recruited from the Rutgers University Douglass Developmental Disabilities Center. The ASDI group was composed of 6 children (2 female, 4 male, M=6.4 years (range=4.9-7.7 years)) who had been diagnosed with ASD and were of similar age to the TD group. The ASDII group was a group of 10 children (3 female, 7 male, M=11.9 years (9.2-15.7 years)), also diagnosed with ASD, who were significantly older in chronological age than either the TD or ASDI groups. Licensed clinicians administered the Stanford-Binet $5^{th}$ Edition intelligence test to the ASDI (M=42.5 (SD=2.9), range=40-45) and ASDII (M=45.8 (SD=15.6), range=40-90) groups. A diagnosis of autism was confirmed by the same licensed clinician using the Autism Diagnosis Observation Scale (Lord et al. (2000) J. Autism Dev. Disord., 30:205-23) (communication+social scores for the ASD1 (M=18.5 (SD=1.9), range 17-21) and ASDII (M=14.2 (SD=2.6), range=11-18) groups). The Gilliam Autism Rating Scale $2^{nd}$ Edition (Gilliam, 2006) was used to confirm diagnosis where appropriate (two non-verbal teenage girls for whom none of the four ADOS modules currently available are appropriate: M=116.5 (SD=10.6), range=109-124).

Procedures

To minimize interference with their daily routines, the experiments were conducted in the classroom settings where the children attended school. Curricular activities were adapted to a computer interface that were built which time-stamped and logged all behavioral events of relevance. These included the touches of the screen indicating the child's voluntary choice to start the experiment, the start of the stimulus presentation displaying the two choices, the child's voluntary choice of target, and the accuracy of the choice. Built-in video cameras recorded the child's face, which were used for further analyses and for further validation and records of the experimental sessions.

Children were seated in front of a 21" touch screen computer monitor (Dell, 4 ms delay with a resolution of 1920×1080) used to display the tasks. Tasks were run using MouseTracker software (Freeman et al. (2010) Behay. Res. Methods 42:226-241). Software produced and designed in-house was used to time-stamp and log the motion caption data, the behavioral events (screen touches), video, and stimulus presentation times, all of which were recorded by the same CPU. This report focuses on the screen touches defining the parameter of interest, to be defined later.

The task consisted of receptive identification match-to-sample (MTS) variants. Three different MTS were used—color, shape, or orientation. All three tasks shared common features: a sample was always displayed at the bottom, center of the screen. Two targets were displayed in the upper left and the upper right corners of the screen. One of the two targets always matched the sample. In the first task—color discrimination—the stimuli of the samples and target were square patches of various colors (e.g., red, orange, yellow, green, blue, purple, pink, black, white, and brown). There were 12-20 trials per session. In the second task—shape discrimination—the stimuli were various black shapes (e.g., square, rectangle, diamond, triangle, circle, oval, arrow, heart, star, and crescent moon). There were 16-32 trials per session. Here some trials displayed ambiguous pairs (e.g. circle vs. oval and square vs. rectangle). Lastly, the third task required mental rotation: an image of a banana was rotated (0, 90, 180, or 270°). There were 36 trials per session. Each participant performed hundreds of trials across sessions.

Figure 15B:
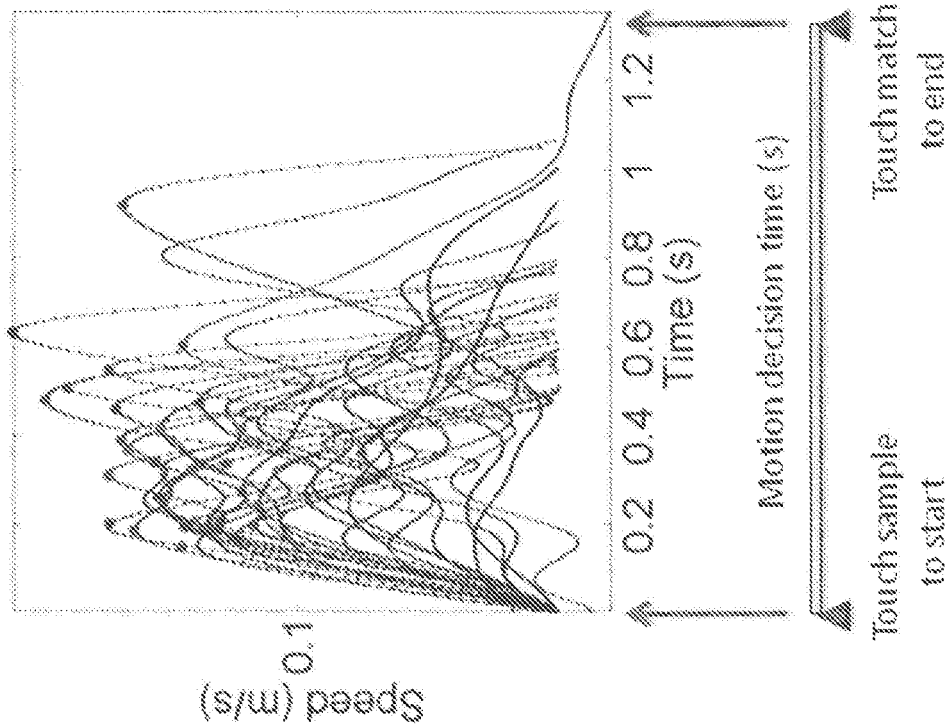
Figure 15A:
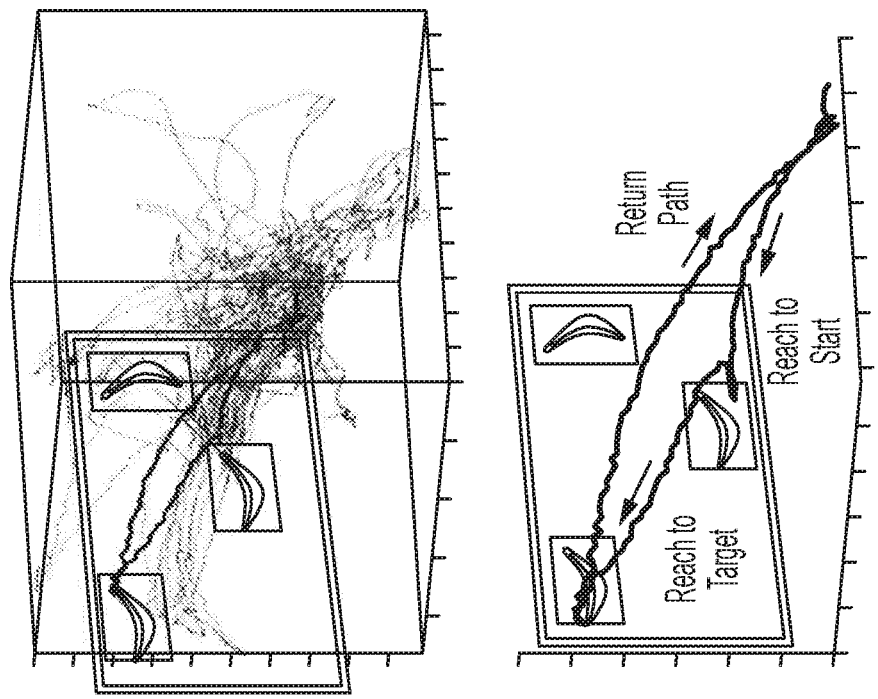

Once seated in front of the touch screen, the child voluntarily pressed the 'start' button at the bottom center of the screen in order to begin each trial. The sample (a color, shape, or object rotated in a particular orientation) appeared in place of the start button. One second later, the two targets appeared in the upper left and right corners of the screen. For each trial, the child was to touch the target that matched the sample. The trajectory of the hand movement was continuously recorded from the first screen touch, initiating the trial with the stimulus presentation, to the second screen touch at the targeted choice. These motions were not always directed toward the targeted choice, as they included part of a decision-making processes that was often still unfolding after movement onset. Uncertainty was reflected in the speed profiles of these reaches, a fact that was exploited by examining the stochastic signatures of the variability of the movement decision response time (denoted here DT reported in seconds (s) or in milliseconds (ms)). The DT defined here is a parameter that comprises the reaction time (RT) to the stimulus, the decision-making time, and the movement time to the targeted choice. FIG. 15A shows sample hand movement data during a session, continuously recorded from the initial trial to the final trial. FIG. 15B shows examples of speed profiles from various trials extracted from the touch of the start button to the touch of the chosen target. Once one target was successfully touched, the stimuli disappeared and a preferred cartoon image appeared to reinforce task performance. No feedback was provided about the correctness of the choice. After a three second delay, the start button reappeared on the screen to prompt the next trial. The child controlled the pace of the experiment as he or she decided when to initiate each trial. The stimuli sets were presented in random order. Tasks were conducted one or two at a time over a period of several weeks. The order of color, shape, and rotation tasks was counterbalanced across participants.

Analytical Procedures

Physical arm-hand movements (rather than arm-static key presses) was measured and the frequency distributions of the DT (defined above) was examined. The psychophysical literature that examines reaction time (RT) data uses the ex-Gaussian distribution, characterized by 3 parameters, to address skewed distributions often encountered in human studies of RT (Lacouture et al. (2008) Tutorials Quant. Meth. Psych., 4:35-45; Whelan, R. (2008) Psychol. Record 58:475-482). The ex-Gaussian is a convolution (mixture) of a Gaussian and an Exponential distribution characterized by the mean (centrality tendency), and standard deviation (dispersion), to capture the left hump of the skewed frequency, and the tau parameter to describe both the mean and the standard deviation of the exponential component (the right tail) often encountered in human RT data.

Here, the Gamma family with only two parameters, the shape (a) and the scale (b), was chosen. Recent work has shown that the Gamma distribution provides the best distribution family fit to the broad range of skewed frequency distributions spanned by parameters of the hand movement speed. These included the values of the peak velocity (m/s) and the time to reach the peak velocity (ms) which were well-described using maximum likelihood estimation (m.l.e.). Herein, the overall distributions of DT for each group and each individual, which contained both the RT and the movement's decision elapsed time revealed highly skewed distributions which were well fit by the m.l.e. of the (a, b)-Gamma parameters. These m.l.e. parameters were then plotted as points on the Gamma plane to gain insights on the patterns of variability of the DT of each ASD group in relation to the TD controls, and also to gain insights on the stochastic signature of each individual within each subgroup. It was specifically addressed whether there were marked gender differences within each group and between the groups, and if the cognitive load of each MTS task produced different effects between the genders. Thus, each ASDI, ASDII, and TD group was broken down into the boys' and girls' sub-groups and their stochastic signatures of DT variability were estimated within 95% confidence regions for each m.l.e. Gamma parameter. Further analytical methods are provided hereinabove.

Results

The three groups of interest, TD, ASDI, and ASDII, were first examined as a function of gender by pooling the DT (s) across all conditions (color, shape, and rotation) to gain an understanding of the overall trend of the data per gender and of the statistical signatures of variability in this parameter for each gender of the TD, ASDI, and ASDII groups. Frequency histograms were obtained per gender-group, and the maximum likelihood estimates (m.l.e.) of the shape(a) and scale(b) parameters of the Gamma probability distribution were obtained for each gender-ensemble within 95% confidence intervals (FIG. 16A and FIG. 16B). These are reported on Table 3. Since highly skewed distributions were obtained, the non-parametric Kruskal-Wallis (ANOVA) test was used to assess gender effects in the TD, ASDI, and ASDII groups. The log of the movement duration time (ms) was used to assess the effects.

TABLE 3

Entries are the maximum likelihood estimates (m.l.e.) for the Gamma shape and scale parameters with 95% confidence intervals for boys and girls in each experimental child-type group (refers to FIG. 16A and FIG. 16B frequency histograms)

| | m.l.e. (shape, scale) | 95% CI (shape, scale) | |
|---|---|---|---|
| TD boys | (2.20, 1.43) | 2.0216 | 1.3053 |
| | | 2.3998 | 1.5824 |
| TD girls | (1.85, 1.80) | 1.6861 | 1.6186 |
| | | 2.0430 | 2.0174 |
| ASDI boys | (1.56, 3.12) | 1.4181 | 2.7839 |
| | | 1.7219 | 3.4981 |
| ASDI girls | (2.26, 1.81) | 2.0214 | 1.5991 |
| | | 2.5428 | 2.0672 |
| ASDII boys | (2.09, 1.34) | 1.9333 | 1.2325 |
| | | 2.2655 | 1.4742 |
| ASDII girls | (3.10, 0.50) | 2.7924 | 0.4457 |
| | | 3.4534 | 0.5613 |

The Gamma m.l.e. shape and scale were plotted on the Gamma plane for each group split by gender in order to gain insights on the stochastic differences within each group, and also between groups, with a focus on the differences between boys and girls with ASD relative to differences between TD boys and girls (FIG. 17D FIG. 17F). The same analyses on the Gamma plane were then performed on the individual members of each group to gain insights into the variability in DT of each individual within his or her gender for each developmental group. The pooled data was then unfolded into the individual conditions (color, shape, and rotation) to assess the effects of increasing the cognitive load on the DT for each group. This analysis was also performed on the Gamma plane for each gender group within the (TD, ASDI, and ASDII) to gain insights into the patterns of the ensemble previously found when grouping each gender-group across all experimental conditions. Table 4 summarizes the Gamma fitting m.l.e. of the parameters and 95% confidence intervals for each group split by gender. The descriptive statistics are reported in the text and captions for the ensemble data pooled across conditions and broken down into individual conditions. Table 5 reports changes in stochastic signatures as a function of stimulus type. Finally, the Gamma analysis was performed on the log-transformed data to uncover possible scaling effects.

TABLE 4

Power fit to the scatter from the individual Gamma fits. Table 4 refers to Power model $f(x) = ax^b$ to fit the scatter of points from the individual boys and the individual girls comprising each of the TD and ASD groups.

| | Power Model Coeff | 95% CI (a, b) | R-square, rmse |
|---|---|---|---|
| TD boys | 4.30, −1.26 | (−5.04, 13.65) | 0.3, 0.5 |
| | | (−3.685, 1.161) | |
| TD girls | 7.81, −1.92 | (6.139, 9.496) | 0.97, 0.2 |
| | | (−2.402, −1.445) | |
| ASD boys | 6.39, −1.86 | (1.383, 11.4) | 0.65, 0.6 |
| | | (−3.125, 0.6133) | |
| ASD girls | 531, −6.24 | (−1346, 2409) | 0.93, 0.2 |
| | | (−10.05, −2.444) | |

TABLE 5

Gamma m.l.e. parameters per cognitive load type, per child-type gender group. Table 5 refers to the plots in FIG. 18D FIG. 18F. The m.l.e of the Gamma parameters for each experimental condition (color, shape, rotation) pooled across all boys of each child-type group and all girls of each child-type group. The first parameter in the third column of the table is the shape and its 95% confidence interval is the first 2-element column vector on the fourth column of the table. The second parameter of the third column of the table is the scale. Its 95% confidence interval is the second 3-element column vector in the fourth column of the table.

|  |  | m.l.e. (shape, scale) | | 95% CI (shape, scale) | |
| --- | --- | --- | --- | --- | --- |
| color | TD boys | 2.2451 | 1.2560 | 1.8909 | 1.0363 |
|  |  |  |  | 2.6656 | 1.5223 |
|  | TD girls | 2.7484 | 0.8005 | 2.2452 | 0.6412 |
|  |  |  |  | 3.3643 | 0.9993 |
| shape | TD boys | 2.7941 | 1.1766 | 2.3832 | 0.9885 |
|  |  |  |  | 3.2758 | 1.4005 |
|  | TD girls | 2.3551 | 1.4702 | 1.9796 | 1.2115 |
|  |  |  |  | 2.8018 | 1.7840 |
| rotation | TD boys | 2.0372 | 1.6270 | 1.7862 | 1.4018 |
|  |  |  |  | 2.3236 | 1.8885 |
|  | TD girls | 1.6110 | 2.5437 | 1.3873 | 2.1353 |
|  |  |  |  | 1.8708 | 3.0302 |
| color | ASDI boys | 1.5910 | 3.2895 | 1.3144 | 2.6291 |
|  |  |  |  | 1.9259 | 4.1157 |
|  | ASDI girls | 2.4178 | 1.2737 | 1.9680 | 1.0134 |
|  |  |  |  | 2.9703 | 1.6010 |
| Shape | ASDI boys | 2.0343 | 2.5005 | 1.7225 | 2.0709 |
|  |  |  |  | 2.4024 | 3.0192 |
|  | ASDI girls | 2.5898 | 1.6746 | 2.1065 | 1.3333 |
|  |  |  |  | 3.1841 | 2.1032 |
| rotation | ASDI boys | 1.3034 | 3.4116 | 1.1178 | 2.8313 |
|  |  |  |  | 1.5199 | 4.1108 |
|  | ASDI girls | 2.3323 | 2.0646 | 1.9326 | 1.6741 |
|  |  |  |  | 2.8146 | 2.5462 |
| color | ASDII boys | 2.2236 | 1.1709 | 1.9441 | 1.0072 |
|  |  |  |  | 2.5432 | 1.3613 |
|  | ASDII girls | 2.4822 | 0.5650 | 2.0250 | 0.4509 |
|  |  |  |  | 3.0426 | 0.7079 |
| shape | ASDII boys | 1.9098 | 1.5418 | 1.6987 | 1.3486 |
|  |  |  |  | 2.1471 | 1.7626 |
|  | ASDII girls | 4.8949 | 0.3154 | 4.1393 | 0.2643 |
|  |  |  |  | 5.7884 | 0.3763 |
| rotation | ASDII boys | 2.0284 | 1.3352 | 1.7022 | 1.0945 |
|  |  |  |  | 2.4170 | 1.6287 |
|  | ASDII girls | 2.4999 | 0.6256 | 1.9703 | 0.4806 |
|  |  |  |  | 3.1719 | 0.8143 |

Movement Decision Time (DT)

Highly skewed distributions were obtained (FIG. 16A and FIG. 16B) for DT. The log-transformed data, which had a tendency towards normality, was examined to assess gender effects and the effects of cognitive load. However, the log-transformed data failed the $\chi^2$ goodness of fit test for normality ($\chi^2=20.11$, $p<10^{-4}$), so the non-parametric Kruskal-Wallis (ANOVA) test was used. The three groups were split by gender to see if DT distributions were different between boys and girls. There was no significant effect of gender on the performance of the TD girls and boys ($\chi^2=0.5$, $p<0.44$, 1359 trials, see FIG. 17A). Girls had a median DT of 2.28 s (range=0.4-37.09 s); whereas, boys had a median DT of 2.32 s, (range 0.3-28.9 s). However, both the ASDI ($\chi^2=10.18$, $p<0.001$, 1021 trials) and ASDII ($\chi2=218.0$, $p<10^{-49}$, 1079 trials) groups differed significantly. Girls had faster median DT than boys in both ASDI (3.01 s (range 0.2-30.5 s) vs. 3.31 s, range (0.6-52.9 s)) and ASDII (1.21 s (range 0.19-10.28 s) vs. 2.20 s (range 0.3-27.5 s), see FIG. 17B and FIG. 17C).

The maximum likelihood estimation of the Gamma parameters revealed that boys and girls in both the ASDI and ASDII groups fell further apart from each other than the TD boys and girls (FIG. 17D). The lack of separation in the TD group is underscored by the non-significant Kruskal-Wallis test above (also see FIG. 17E). However, unfolding the boys and girls in the ASDI and ASDII groups reveal clear differences in the Gamma plane (FIG. 17F).

Differences between groups were found between the different stimulus conditions for color ($\chi^2=57.16$, $p<10^{-13}$, 1,007 trials), shape ($\chi^2=117.6$, $p<10^{-26}$, 1,199 trials), and rotation ($\chi^2=168.06$, $p<10^{-37}$, 1,463 trials, FIG. 18A through FIG. 18C). FIG. 18D through FIG. 18E reveals that the separation between boys and girls in DT can be accounted for by the color condition in ASDI and the shape condition in ASDII.

Figure 19A:
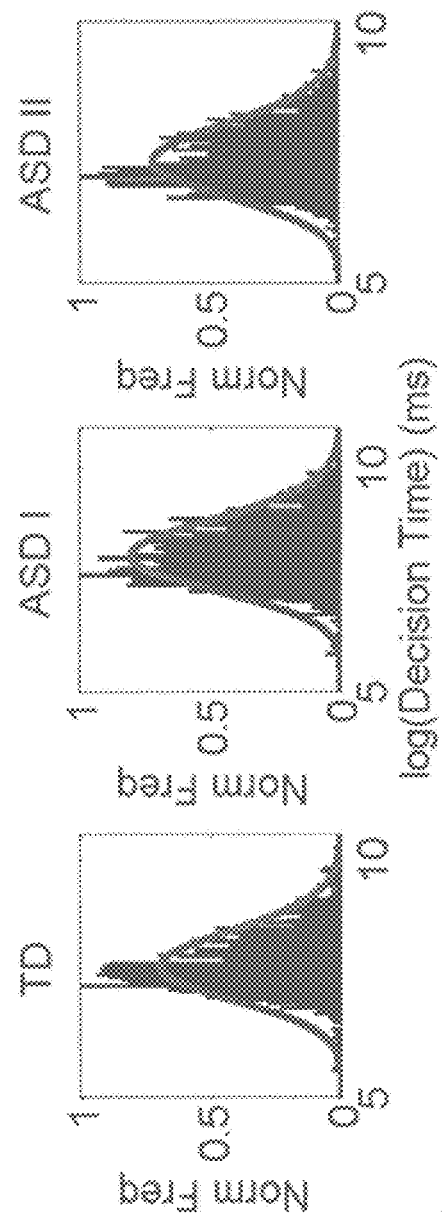
Figure 19B:
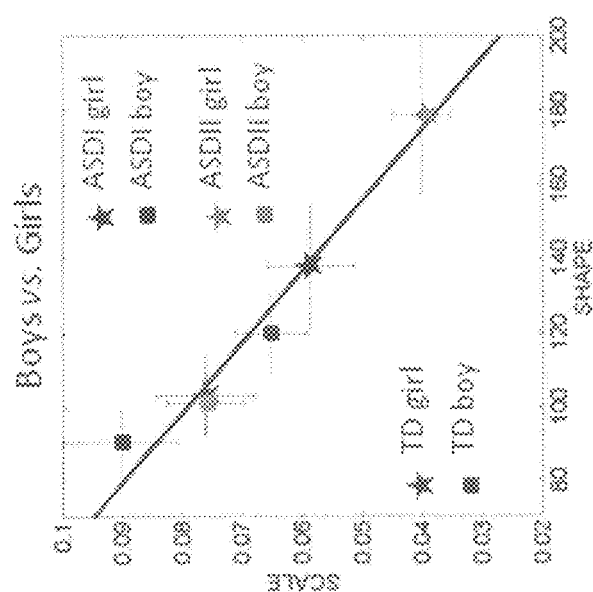

Lastly, the log-transformed DT (FIG. 19A) data is displayed on the Gamma plane (FIG. 19B) and revealed a tight fit, with TD children of both genders falling between the boys with ASD (to the left/Exponential side of the scale parameter range) and the girls with ASD (to the right/Gaussian side of the scale parameter range). Extreme differences that had been so apparent between girls and boys in both ASDI and ASD II groups were absent in the TD children. While the TD separation falls in the skewed range of the Gamma parameter plane (multiplicative effects (Limpert et al. (2001) BioScience 51:341-352)) the girls with ASD scale with age towards the Gaussian range (additive effects) and the boys with ASD are in the exponential range. The FIG. 19B shows that as the girls with ASD get older, they move farther from the typical girls. In marked contrast the younger boys with ASD start out far apart from the TD children, consistent with a higher chance of detecting their abnormalities earlier on during clinical diagnosis. The extreme gender difference found here questions if there may be potential confounds skewing the accuracy of the reported 4.3:1 boys to girls ratio (Newschaffer et al. (2007) Annu. Rev. Public Health 28:235-258).

Accuracy

Overall, participants chose the correct target 91.0% of the time. Examining differences in accuracy between groups revealed that accuracy for the TD group was 92.4%, 86.9% for the ASDI group, and 92.0% for the ASDII group. A Kruskal-Wallis ANOVA revealed an effect of group on accuracy ($\chi^2=30.72$, $p<0.001$, 4,976 trials). Post hoc tests revealed that the ASDI group was less accurate than the ASDII ($p<0.001$) and the TD ($p<0.001$) group; however, the TD group did not differ from the ASDII group. Girls (93.7%) were more accurate than boys (89.3%): $\chi^2=27.67$, $p<0.001$, 4,976 trials. The cognitive complexity of the discrimination task was partially revealed by comparing accuracy for the three types of trials: color (95.2%), shape (94.5%), and rotation (83.4%). A Kruskal-Wallis ANOVA revealed an effect of trial-type accuracy ($\chi^2=175.94$, $p<0.001$, 4,976 trials). Post hoc tests revealed that accuracy was significantly less for the rotation condition than for both the color ($p<0.001$) and the shape condition ($p<0.001$); however, the color and shape conditions did not differ from each other.

This study investigated gender differences in the movement decision time (DT (s)) across two different age groups of children with ASD in relation to TD controls. A simple paradigm and a metric are presented that allows for fast measurements of parameters that relate to decision making processes during the performance of natural pointing movements. This paradigm was adapted from curricular activities performed in classroom settings during short 10-15 minute blocks. The outcome revealed striking differences between the boys and girls with ASD that were absent in the TD children.

Embedding the decision-making-RT time epoch within natural movements which end at the goal (e.g., the touch of the targeted choice) enables one to set an upper-bound on the full decision-making process. The Gamma family (with only two parameters) can also be used to characterize the range of skew of the frequency distributions and capture the full range of human variability present in the broad spectrum of human cognition, from exponential to normal. Utilizing these methods, one can not only see where an individual with ASD falls relative to members of his or her ASD group, but, more importantly, one can see where she or he falls in the broad spectrum of human diversity. This can result in a more inclusive model of all types of autism, permitting comparative analyses on the Gamma-plane scatter of other populations. These could include those with a diagnosis of autism linked to known genetic disorders (e.g. Fragile-X, Phellan-McDermid syndromes) as well as others with non-autistic disorders with known genetic origins (e.g. Williams and Down syndromes) to gain insights into the autism phenomena from a bigger-picture perspective.

The girls with ASD in the study were significantly faster than the boys with ASD, and overall faster than the TD children. In the case of ASDI they were also comparable to their peers, the TD girls of similar age. Importantly besides the decision time, the DT parameter also includes the movement time when sensory feedback from movement would be obtained. In the case of the boys however, the exponential distribution of DT suggests that the sensory feedback from a previous hand motion would carry no predictive information for future trials because the exponential is the most random, memoryless distribution. The boys would have to keep repeating their movements to seek sensory feedback—likely absent from the highly random fluctuations of the timing of their hand motions. The boy's DT stochastic signatures would help to explain the higher frequency of repetitive stereotypic behavior (RSB) detected earlier in boys. The girls with ASD at the opposite Gaussian range of the Gamma family would explain their milder RSB consistently reported from meta-analyses of large samples (Mandy et al. (2011) J. Autism Dev. Disord., 42:1304-13; Volkmar et al. (1993) J. Autism Dev. Disord., 23:579-591), also possibly contributing to greater likelihood of delayed diagnosis. Given that sensory feedback travels through the spinal cord to the central nervous system through two pathways: the slower spino-thalamic pathway for thermoreceptors and nociceptors to modulate temperature and pain; and the faster dorsal-column-medial lemniscal pathway for tactile and kinesthetic information; the instant results open the question of whether sensory-feedback is processed extremely different in girls and boys with ASD. That is, whether girls are more prone to pain-temperature disturbances and boys more prone to movement-tactile disturbances.

Notably, the results hold across different age groups, with marked gender differences in the early stages of development (before 4 years of age). The observed gender differences are congruent with reports in the developmental literature on early disparity between boys and girls (Stromswold, K. (1998) Hum. Biol., 70: 297-324). Across development, from young, pre-school children to college-level participants, a power relation spanning several orders of magnitude was found that captured the systematic evolution of the statistical signatures of spatio-temporal percepts from the movement (endogenously sensed) as a function of perceptual demands (exogenously sensed). These movement signatures had a systematic correspondence with the evolution of decision making parameters such as the latency and accuracy across age groups.

Across ages, performance was unambiguously different when the pointing motion was devoid of cognitive loads, as in the simple biomechanical pointing task. This was the case despite the fact that this task shares similar biomechanical demands and kinematics with the decision-making variant of the pointing task. The implications of this result are that the different percepts experienced by the human kinesthetic system can be precisely characterized by power relations using the stochastic signatures of somatosensory processes, measured at the motor output. This readout conveys information about cognitive demands and perceptual goals when the action is deliberate and in the cases where the action is automatic. This information can serve to physically measure the types of mental processes that cognitive psychologists have previously proposed.

Example 8

A cohort of 56 participants ranging from 3.5 to 30 years of age with varying intellectual capabilities was examined Individuals with ASD had an IQ range between 40 and 110. For the typically developing (TD) individuals, IQ is reported 90 and above, with education spanning from kindergarten to college levels. For each participant, thousands of trials (per stimulus type) from both movement classes were collected to build frequency distributions for the values and times of the speed maxima. The unit time to reach the peak velocity was 100-200 ms. Each movement was completed within 1 second. The relevant parameters of the movement were densely sampled across 20-minute sessions for each subject with a minimum of 2 sessions per day. The younger children took 12 sessions during their play time spread out across several weeks to avoid disrupting their routines. The older participants could complete the experiments across 2-4 sessions broken into morning and afternoon blocks, so as to avoid fatigue. The thousands of trials measured over time provided high quality statistical data for each individual in the cohort studied.

Figure 20A:
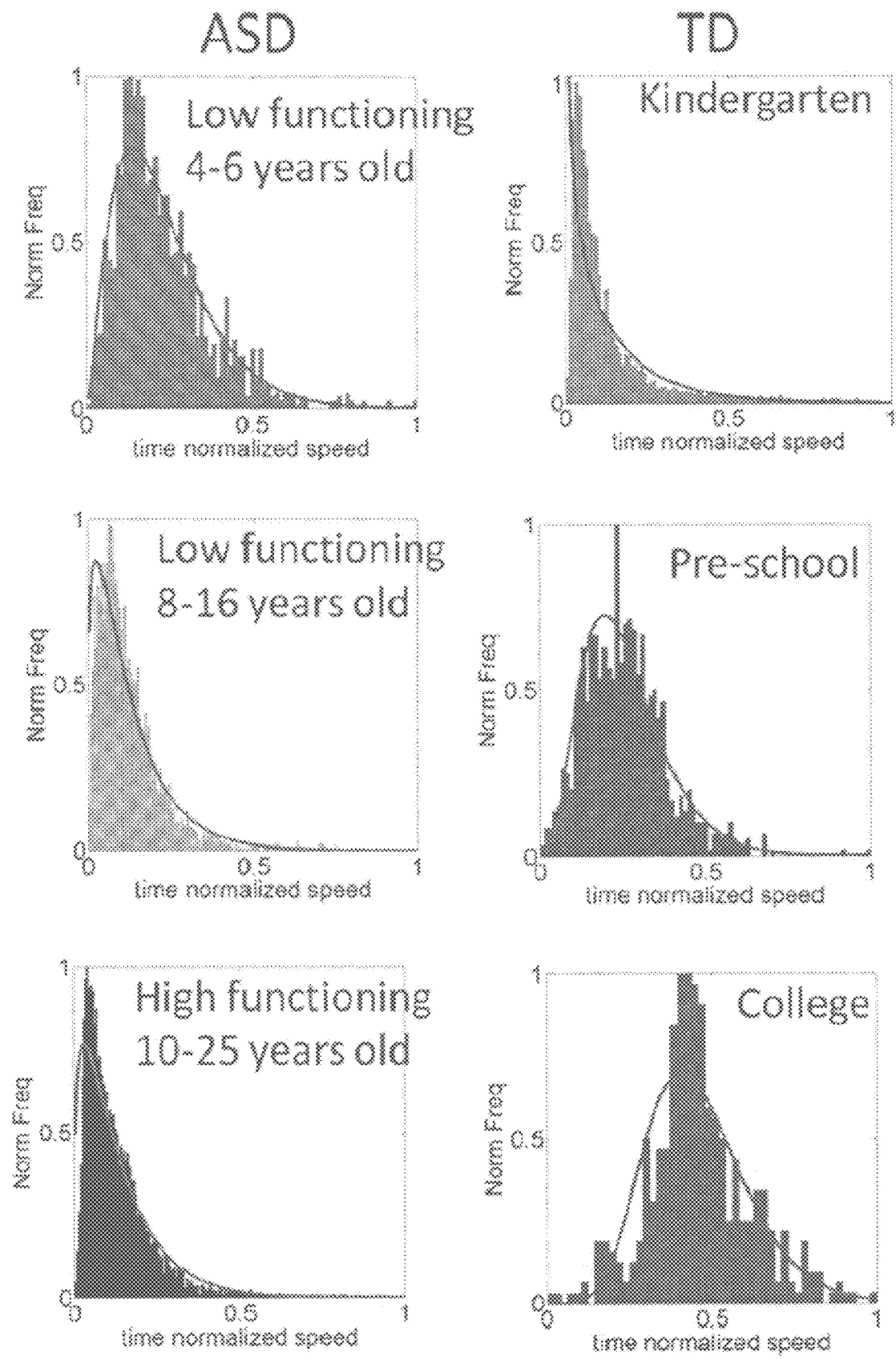

The trajectories of the hand toward and away from the target are rich in other important parameters that can also be used to objectively track performance trial-by-trial. The stochastic signatures of the maximum speed amplitude and its timing revealed differences in somatosensory-motor patterns. Aside from these parameters, the trial-by-trial time-normalized path length as the hand approached and left the target was analyzed. This is the distance traveled by the hand from the onset of the movement, when the speed steadily increased, until the movement offset, when the speed was near zero, divided by the latency of the movement. This parameter is an important physical quantity of movement trajectories that amounts to the averaged speed on a trial-by-trial basis. FIG. 20A shows the frequency histograms of the time-normalized path length parameter across the six self-emerging clusters of the scatters from FIGS. 20B (intended) and 20C (unintended). Each point in the scatter represents the unique stochastic signature of each participant labeled in the (a, b)-Gamma plane. This labeling is determined according to the mle of the parameters from the continuous Gamma probability distribution family Each self-emerging cluster in FIG. 20B was determined by coloring the scatter by age and IQ level.

Figure 20C:
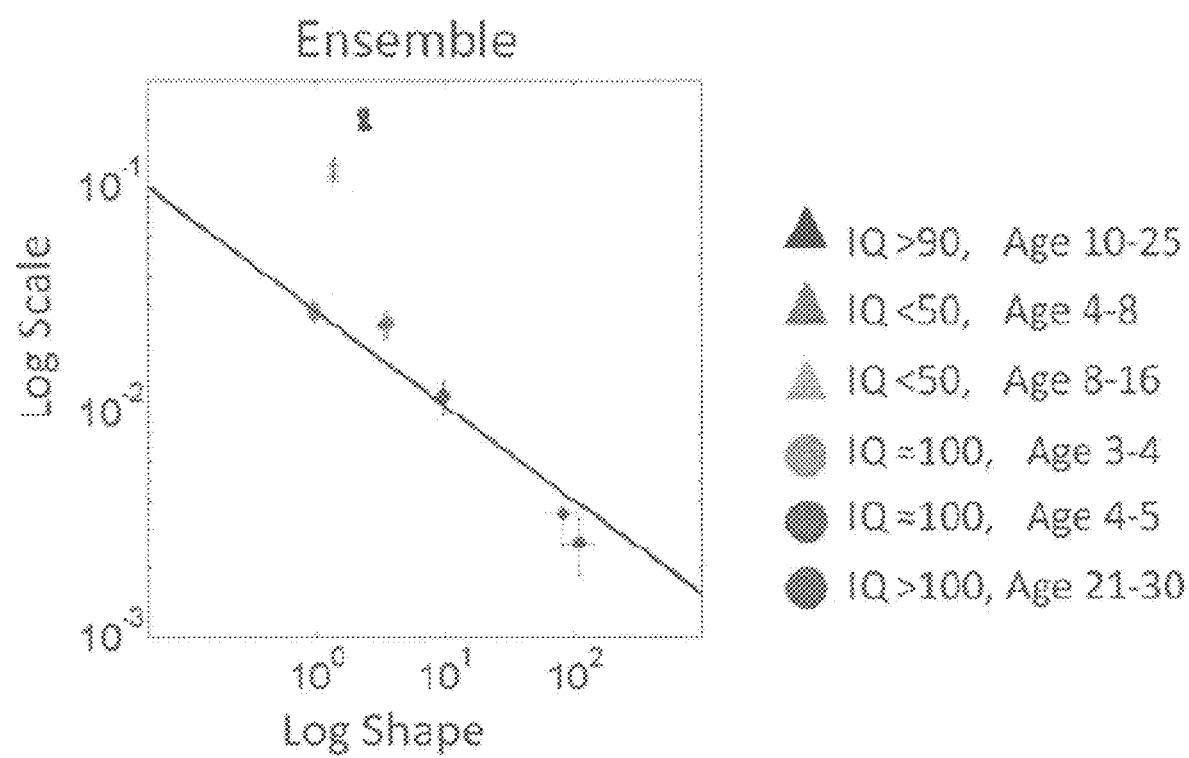

The lower panels of FIG. 20B show details of TD and ASD clusters from the overall scatters of the top panels. These are depicted using log-log scales spanning several orders of magnitude along both axes of the (a,b)-Gammaplane. Significant correlations were found between the a-shape and b-scale parameters with age and IQ, respectively. These correlations differed between TD and ASD clusters. The schematic arrows in the zoomed-in panels of FIG. 20B are meant to illustrate these correlations. FIG. 20C shows the (a,b) values for each of the self-emerging clusters in FIG. 20B corresponding to the frequency distributions of FIG. 20A. It is critical to note that these clusters emerged as the scatter was colored by age and IQ. They were not determined a priori but rather revealed by the inherent stochastic signatures of the somatosensory-movement data. In the TD cohort, the clusters separated according to their academic level, with clear differences based on age and IQ. In the cohort with ASD, the verbal individuals with higher IQ clustered separately from their non-verbal counterparts. Interestingly, two of three exceptions to this rule (best appreciated in the zoomed-in lower panel from the retractions) were the individuals scoring highest on the repetitive-stereotypical behavior subscale of the ADOS. The IQ of these individuals is in the 80-90 range and they have some verbal abilities, yet their somatosensory-motor stochastic signatures placed them with the non-verbal individuals with IQs below 50. The third outlier whose signatures fell close to the young TD cluster was recently mainstreamed to a regular kindergarten. Notice also that the clustering with respect to age for the TD cohort and the cohort with ASD branched in opposing directions. Older individuals with ASD diverged from the Gaussian ranges of the (a,b)-Gamma-plane quantified in college-level adults. By marked contrast, younger children with ASD fall closer to the cluster of the younger TD children, emphasizing the potential for a developmental change and the importance of early interventions. This is also appreciated in FIG. 20C, which depicts the stochastic signatures of the ensemble according to the self-emerging clusters.

A power-law fit was found for the stochastic signatures of the TD participants from kindergarten to college ages. The data was fitted to $f(x)=ax^b$ with a=0.028 and b=−0.420, with 95% confidence intervals [0.025, 0.030] and [−0.492, −0.347], respectively. The goodness of fit parameters were SSE=4.63×10−6, R2=0.992, adjusted R2=0.991 and RMSE=0.0010076.

The clusters found in the line fit span several orders of magnitude. They serve to blindly characterize the kindergarten-to-college transition with respect to this somatosensory-motor integration metric within a typical developmental trajectory. Notice that the point representing the cluster of young non-verbal children with ASD fell close to the line. This is in marked contrast to the points representing the clusters of older participants with ASD, with and without verbal capabilities, localized off the typical developmental path, as shown in the scatter in 20B.

Figure 21A:
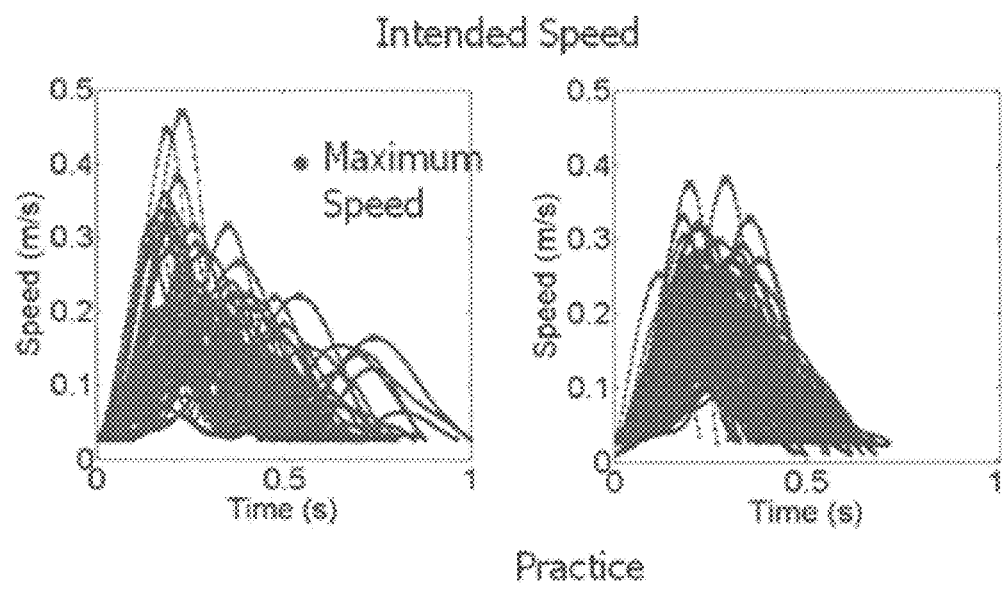
Figure 21B:
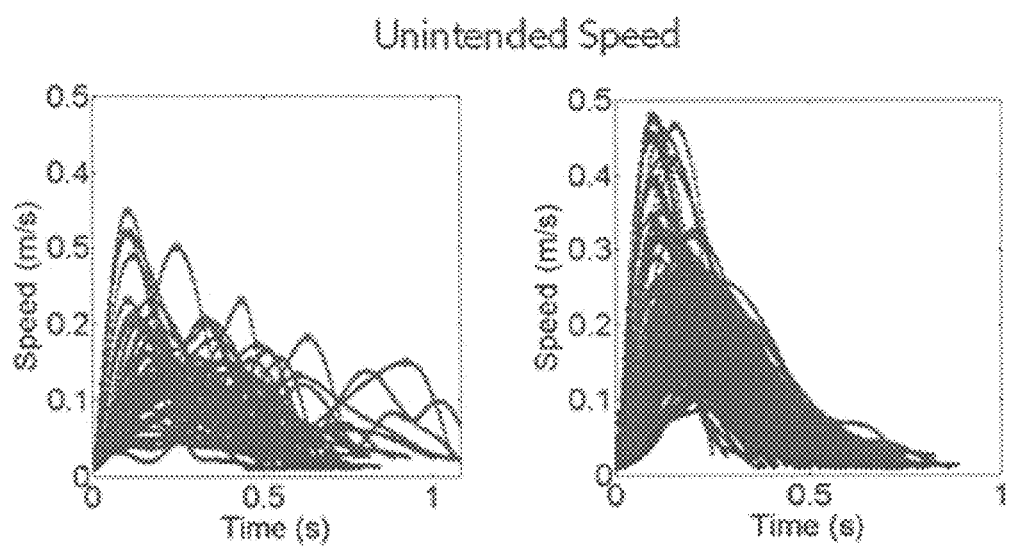
Figure 21E:
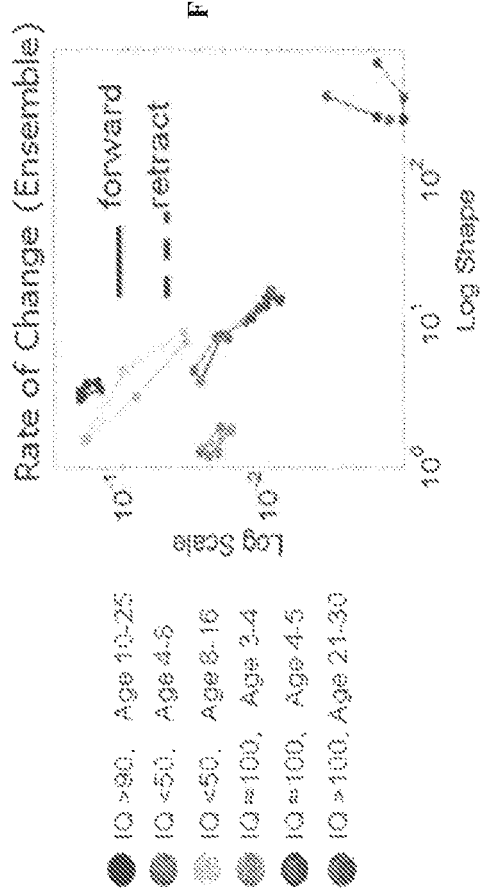
Figure 21C:
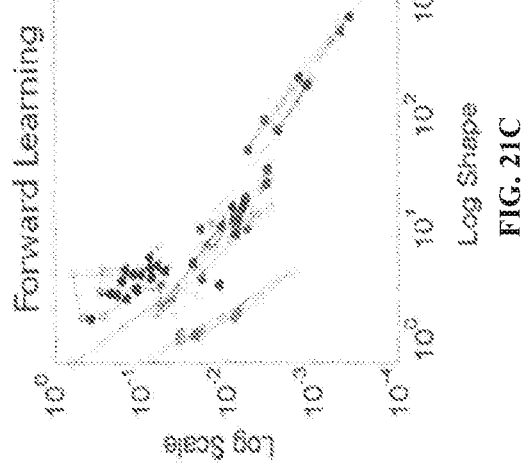

The changes in the cognitive/perceptual stimulus affected the hand speed profiles. They shifted from unimodal to multimodal; decreased the accuracy of the responses in the children (Kruskal-Wallis p<0.05, $\chi2$ 14.99), and increased the latency of their decision making responses (Friedman test, stimulus effect p<4.9×10−102, $\chi2$ 482.41, cluster effect p<8.5×10−97, $\chi2$ 458.16). Examples of multimodal speed profiles are shown in FIGS. 21A (intended) and 21B (unintended). These changes manifested in both TD and ASD groups. After minutes of practice, the speed profiles recovered their unimodality and the movements themselves became faster. This is shown on the right panels of FIG. 21A and FIG. 21B. The stochastic signature of each individual was also tracked by task: the discrimination of color, the discrimination of geometric shapes, and the discrimination of rotated objects that were otherwise identical (FIG. 21C and FIG. 21D). Some participants systematically shifted towards the Gaussian range of the Gamma plane (positive gain), while others moved back (negative gain) or had near-zero gain on the Gamma plane with variable rates. The overall behavior of the ensemble could also be objectively quantified. This is shown in FIG. 21E for each of the self-emerging clusters. Notice that on this logarithmic scale the cluster comprised by the older nonverbal participants with ASD experienced the largest overall shift toward the typical ranges.

Figure 21F:
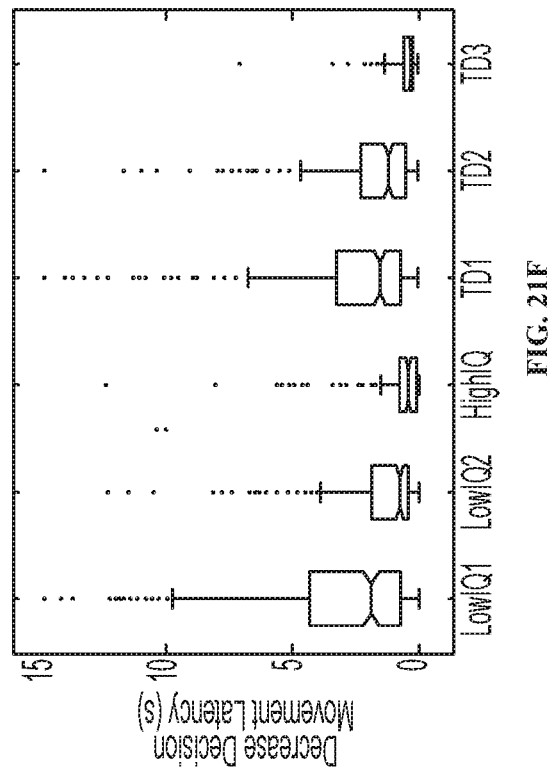
Figure 21D:
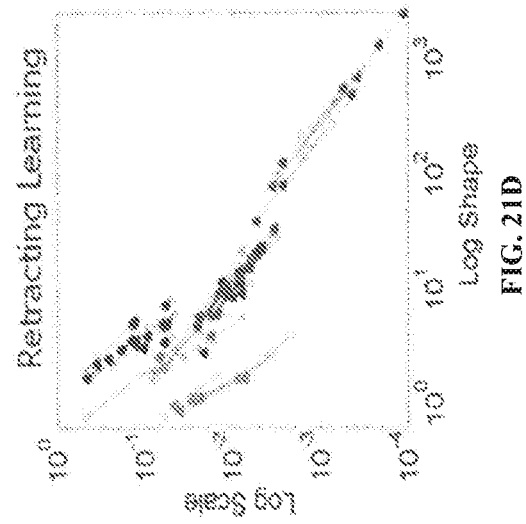

FIG. 21F shows the decrease in latency(s) in initiating the intentional movement when comparing the 150 earlier trials to the 150 later trials. Children with ASD and lower IQ experienced the largest improvements in combination with the largest shifts in the somatosensory-motor integration stochastic signatures along a different course of performance gains for the incidental movements (FIG. 21E).

It has been shown herein that there is a continuum of human somatosensory motor performance that changes as a function of cognitive/perceptual manipulations. Such changes are systematic with age and IQ across several orders of magnitude of the log-log (a,b) Gamma plane. This continuum can be well characterized with a power relation that captures the developmental trajectory of typical individuals and localizes self-emerging statistical subtypes of individuals with a diagnosis of ASD relative to the self-emerging statistical subtypes of TD individuals. In particular the metric automatically detects verbal and non-verbal individuals with ASD. This is the first power relation that captures a connection between the somato-sensation of natural body movements and cognitive performance. This relation expresses the internal kinesthetic sensation that gives rise to a percept of the body. This percept is objectively quantifiable at the motor output and separable in movements that have different levels of intentionality. The manifestation of this relation is fundamentally different for individuals with a diagnosis of ASD. Their stochastic signatures of sensory-motor integration and decision making are in different statistical classes than those from controls. Each individual in the spectrum is unique and learns this task in a unique manner, a result that would have been missed had homogeneity been assumed a priori, formed groups accordingly, and assumed an underlying probability distribution common to the ASD cohort.

It has been shown that the stochastic signatures from the different self-emerging statistical classes in ASD can be shifted towards typical statistical regimes, particularly in unintentional movements that require no verbal instructions. Movement practice made the children faster and more accurate in their decision-making. Moreover, there were marked individual differences in their gains, which could be quantitatively track over time. The metrics permit objectively tracking the impact that changes in cognitive stimuli have on somatosensory-motor performance in real time for a single person and experimental session as well as longitudinally. The metrics can be applied to automatically track progress during sessions with a teacher or therapist and also before and after drug clinical trials.

Learning programs can be personalized to better exploit the somatosensory-motor capabilities and the cognitive learning predispositions inherently present in each child. In particular, automatic-unintended movements which occur spontaneously and exist embedded in communicative pointing gestures provide a means to objectively quantify changes in a type of spontaneous cognitive learning that occurs without explicit instructions, largely beneath awareness.

This quantification can be performed independent of deductive inferences, and works even for children that are non-verbal and labeled as "low-functioning" ASD. These new metrics along with a new formal statistical framework offer a transformative view of this highly heterogeneous disorder.

Example 9

When performing instrumental activities of daily living, one may voluntarily monitor some portions of the movement while other portions spontaneously change, without much conscious awareness. For example, during a reach, once the goal is acquired, one often deploys a motor program that launches the hand forward and retracts the arm to the resting position without consciously thinking about which joints are rotating, flexing, extending, adducting, or abducting. Often both covert-spontaneous and overt-intentional modes of action work together, and one can easily multitask fluidly, without completely freezing one movement in favor of another. This is not the case in patients with Parkinson's disease (PD) (Isoda et al. (2007) Nat. Neurosci., 10:240-248; Hikosaka et al. (2008) Frog. Brain Res., 171:375-382; Hikosaka et al. (2010) Trends Cogn. Sci., 14:154-161; Heilman et al. (2011) Clinical neuropsychology, Ed 5. Oxford, UK: Oxford UP), who typically have more problems initiating internally evoked (endoevoked) than externally evoked (exoevoked) movements, a phenomenon called "akinesia paradoxical" (Heilman et al. (2011) Clinical neuropsychology, Ed 5. Oxford, UK: Oxford UP). Assessing the movements of participants with PD allows one to test hypotheses about the role of basal ganglia—cortical circuits in mediating intentional versus more automated controls of action. The basal ganglia are critical not only for the initiation and maintenance of movements, but also for the learning and maintenance of procedural memories (Jog et al. (1999) Science 286:1745-1749; Lehericy et al. (2005) Proc. Natl. Acad. Sci., 102:12566-12571; Yin et al. (2009) Nat. Neurosci., 12:333-341). The loss of dopamine in the posterior regions of the putamen—a region of the basal ganglia associated with the control of habitual behaviors and procedural memories—forces PD patients to more heavily rely on conscious planning and intentional guidance (Chevalier et al. (1990) Trends Neurosci., 13:277-280; Albin et al. (1995) Trends Neurosci., 18:63-64; DeLong et al. (2009) Parkinsonism Relat. Disord., 15:S237-S240). In contrast, conscious-intentional guidance—thought to be mediated by the caudate and rostral putamen (Middleton et al. (2000) Brain Cogn., 42:183-200; Yin et al. (2004) Eur. J. Neurosci., 19:181-189; Yin et al. (2005) Eur. J. Neurosci., 22:505-512; Yin et al. (2005) Eur. J. Neurosci., 22:513-523; Yin et al. (2006) Behav. Brain Res., 166:189-196)—appears to be relatively spared from the degenerative process early in the course of PD (Kish et al. (1988) N. Engl. J. Med., 318:876-880). Because of this dichotomy, it has been suggested that many of the behavioral difficulties, including bradykinesia (slowness of movement), lack of flexibility in switching between tasks, and an inability to multitask, can be at least in part traced back to the deterioration of this endogenous/automated control system. A recent hypothesis suggests that abnormal function of the automated control system may also "impede the expression of goal-oriented actions" in PD patients (Redgrave et al. (2010) Nat. Rev. Neurosci., 11:760-772).

This postulate has been challenged by studies of habitual learning (Frank et al. (2005) Neurology 65:1101-1103; Shohamy et al. (2006) Neuropsychologia 44:774-784), but the results have been confounded with medication status. Furthermore, using carefully controlled tasks, other studies have shown in-tact trial-and-error, habitual learning in PD patients (Swainson et al. (2006) Neuropsychologia 44:1290-1304; de Wit et al. (2011) J. Cogn. Neurosci., 23:1218-1229). Thus, it is unclear whether the deficits were due to impaired procedural/habitual learning or impaired memory or attentional processes (Swainson et al. (2006) Neuropsychologia 44:1290-1304).

Here, the performance of participants with PD, tested off dopaminergic medications, and age-matched normal controls (NCs) were compared as they reached forward to an external target and retracted toward the initial posture. The balance between voluntary and automated modes of controlling the degrees of freedom (DOF) of the arm was addressed.

Methods

Participants

Nine patients with PD (one female, eight males) and nine age-matched healthy subjects performed 3D pointing motions (forward and back) in the dark. Standard kinematic analyses of the forward hand motions of these subjects were presented (Adamovich et al. (2001) Neurosci., 104:1027-1041). Briefly, the PD patients were all mild to moderate in degree (Hoehn and Yahr Stages 2 and 3) with mean (SD) United Parkinson's Disease Rating motor scores of 25.96 (5.34). All patients had clinically typical PD, as reviewed by at least one movement disorder specialist, and their motor disabilities were responsive to antiparkinsonian medications. No patient had any off-state action tremor or dyskinesia of more than minimal amplitude. All subjects were right handed and reached with their right arm. PD patients were studied in the "off" state (had not taken their antiparkinson medication for at least 12 hours before testing).

Description of Procedures or Investigations Undertaken

The subjects were seated with their right arm flexed at the elbow, with the forearm semipronated and vertical such that the hand was on a sagittal plane that was ~10 cm to the right of the subject's ear. The subjects faced a programmable robot arm (Hudson Robotics; CRS 255A) that presented targets in 3D space. A small light-emitting diode was attached to the tip of the robot's arm and served as the target. Two optoelectronic cameras (Northern Digital) were used to record positions of five infrared emitting diodes (IREDs) that were affixed to the following segments of the subject's limb: the acromial process of the scapula (shoulder), the lateral epicondyle of the humerus (elbow), the ulnar styloid process (wrist), as well as on the nail of the index fingertip and on the robot arm tip. The subjects were asked to fully extend their right forefinger and to not move it with respect to the wrist. Two-dimensional coordinates of the IREDs were monitored by each camera. Data from both cameras were sampled at 100 Hz and stored as 2D binary files. Then they were low-pass filtered using a Butterworth filter with a cutoff frequency of 8 Hz, and three-dimensional coordinates were reconstructed.

The robot randomly presented five targets in two planes. Four targets formed a diamond in a frontal (coronal) plane. The geometric center of this diamond was on a sagittal plane that was defined by the subjects' right shoulder but was ~43-48 cm in front of the right shoulder. The two diagonals of the diamond were ~50 cm long. The fifth target was located on a sagittal plane directly in front of the right shoulder, but ~12 cm further from the shoulder than the four target diamond. Exact distances from the shoulder were individualized for each subject by first positioning the furthermost (fifth) target at a distance approximately equal to the length of the subject's arm with the subject's fingers being clenched. This positioning of the subject relative to the target prevented the subject from having to fully extend the arm to reach any of the targets.

All subjects reached using their dominant right forelimb. Their initial limb position, as mentioned above, was with their right arm flexed at the elbow, with the forearm semi-pronated and vertical such that the hand was on a sagittal plane that was ~10 cm to the right of the subject's ear. The subjects attempted to "touch" the target with their right forefinger and returned their arms to their initial positions in one smooth movement, without pausing at the target. Three conditions were designed to examine the contributions of visual cues during the forward-reaching movement, including extrapersonal vision (target cue), or a body-centered visual cue (the moving forefinger), versus no cues (darkness). In each of the three conditions (No Vision, Target Vision, Finger Vision), targets were initially transiently presented as points of light within 3D space in a completely darkened room.

In the body-centered visual cue condition, the moving hand's location was marked by a point of (light emitting diode) light placed on the tip of the forefinger. In the other conditions (target cue and total darkness), this body-centered cue was not present. In the target cue condition, the target light remained illuminated during movement, but the moving finger could not be seen. In the no cue condition (No Vision), neither the finger nor the target light was illuminated during the reaching movement.

In all three experimental conditions, the robot arm held the target position for 1.5 s, during which time the subject was able to view the target. Then a short auditory signal (tone) instructed the subjects to close their eyes in the No Vision condition, at which time the robot arm retracted. A second auditory tone 1 s later signaled subjects to "touch" the memorized target location with their forefinger and then to bring their arm back to the initial position in smooth continuous movements without "corrections" near the target. The subject's eyes were closed throughout the movement.

In the Finger Vision condition, the timing of target presentation and response initiation was the same as in No Vision condition; however, the LED on the fingertip remained illuminated and visible throughout the movement. During the Target Vision condition, the LED on the forefinger was turned off, but the target light remained on, and the experimental condition was otherwise the same as the former conditions. The intensity of the target LED on the robot arm was adjusted to prevent the possibility of the subject seeing his/her forefinger at a distance ~1-2 cm from the target. In addition, a strong overhead light was turned on between trials to prevent dark adaptation. Thus, the only available visual information throughout the movement in this condition was the point/light target.

Statistical and Analytical Measures

To address the hypothesis of voluntary versus automated control, the arm joints and the DOF decomposition were focused on. However, the degrees of freedom of the arm map to the position orientation of the hand. Thus, two additionally related sets of parameters were examined: the end point error around the target and some symmetry related to coordinate transformations between visual targets and arm joint configurations.

Results

Forward Motions to an External Target

End Point Errors

Figure 22:
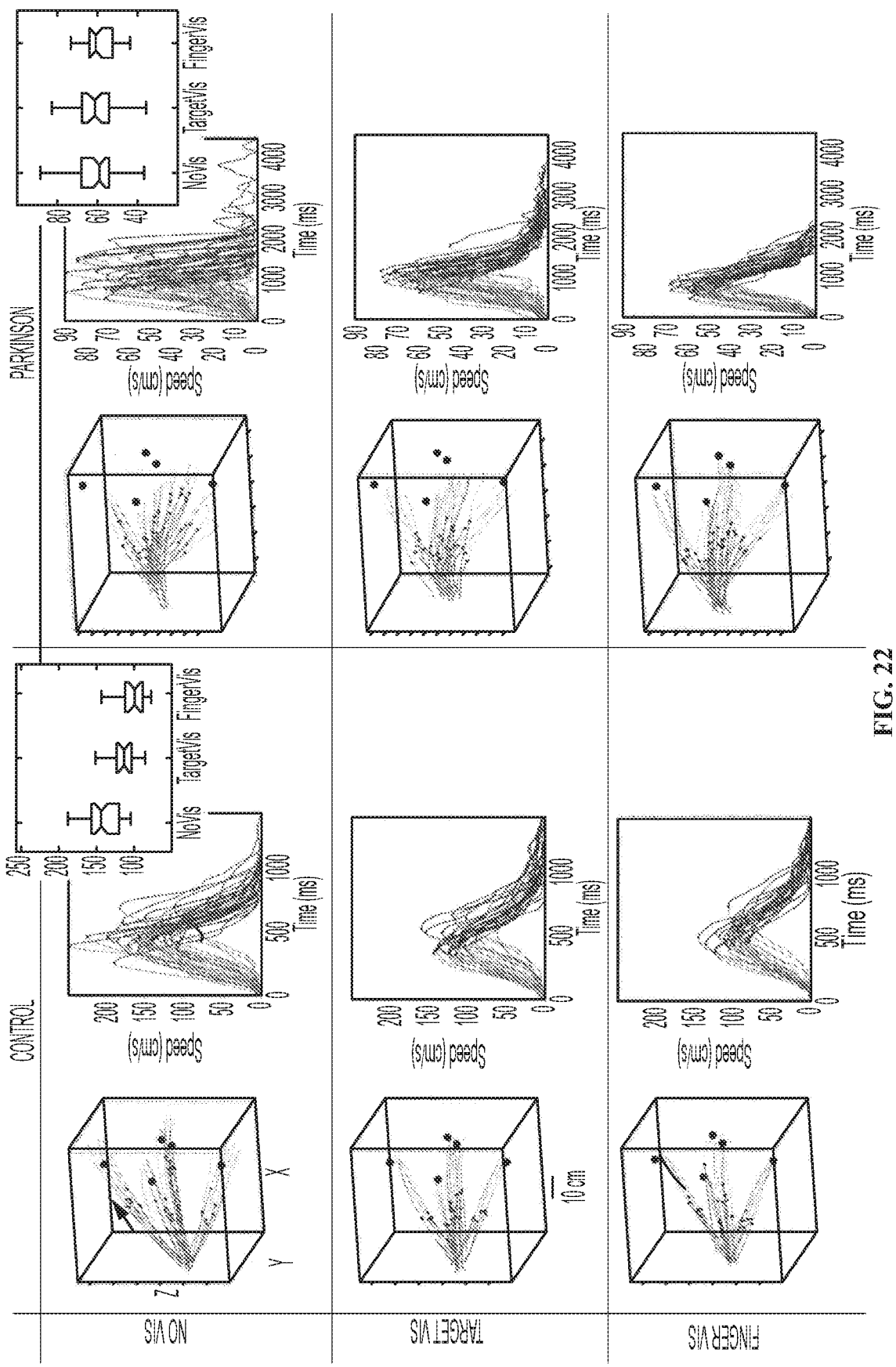

Hand trajectories from a typical NC and a typical PD patient are depicted in FIG. 22 along with the speed profiles. Notice the significant effects of the form of sensory guidance on the peak velocity value in NCs ($p<10^{-10}$). These effects were not significant in the participants with PD ($p>0.8$). The initial segments mark the first pulse of the reach up to the velocity peak.

Figure 23:
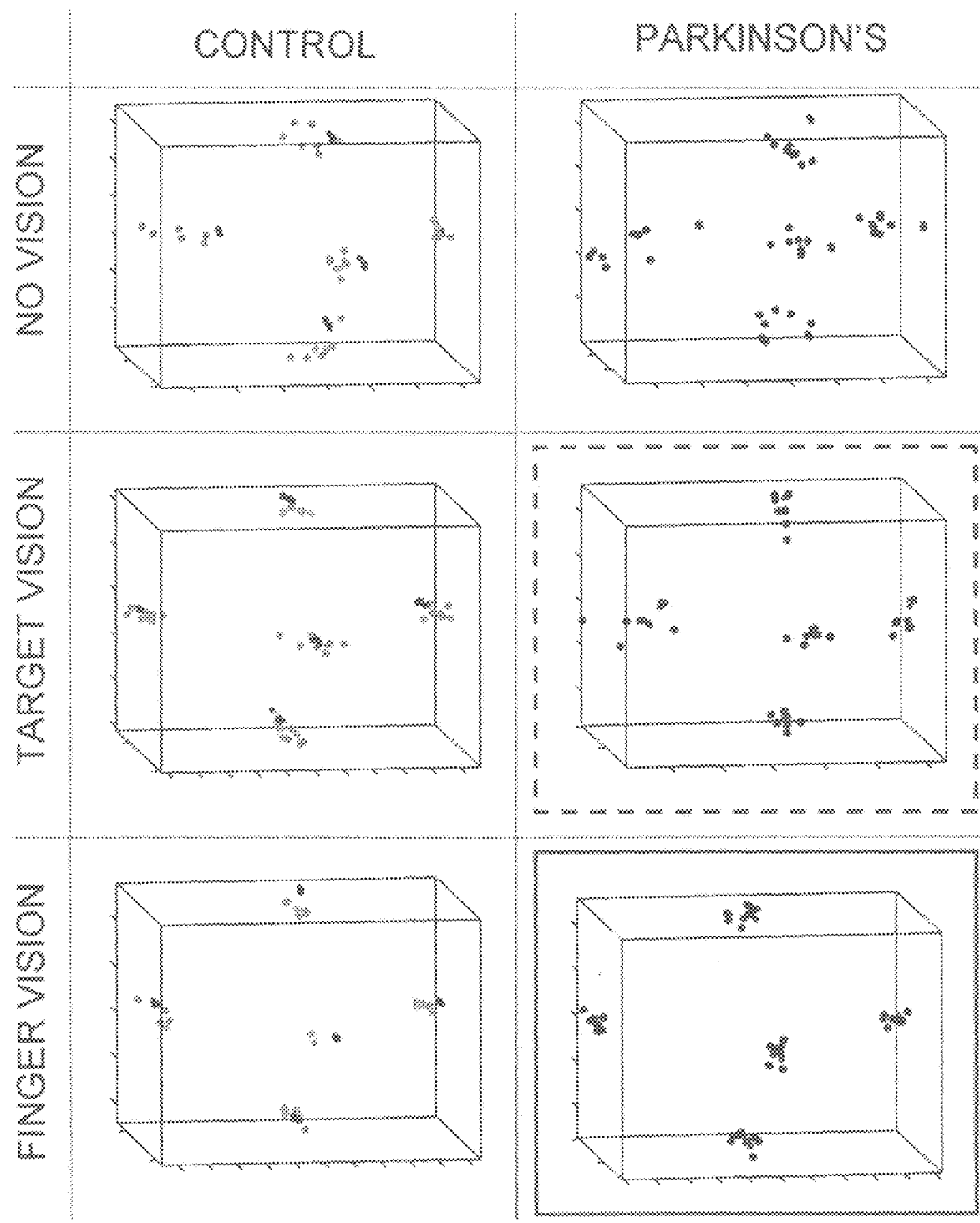

The beneficial effects of finger vision can be best appreciated by assessing the end point errors (FIG. 23). With end point errors as the dependent variable, the effects of target location and stimulus (sensory-guidance) conditions were significant (two-way ANOVA) for both groups of participants with an a level of 0.01. Each column in FIG. 23 shows, for a representative participant in each group, the end point error distribution at each target location. Notice that in each participant group, the type of sensory guidance had a significant effect on spatial accuracy. During finger vision, PD patients were at their best in these forward reaches. These differences, when compared pairwise between subjects with PD and NCs, were statistically significant across target location and the type of sensory guidance.

Trajectory Ratios

In all three conditions, the scatter and the linear regression fit were significantly different between NCs and participants with PD, indicating atypical transformation of coordinates and atypical integration of visual and proprioceptive inputs across the different spatial target positions under examination.

Figure 24:
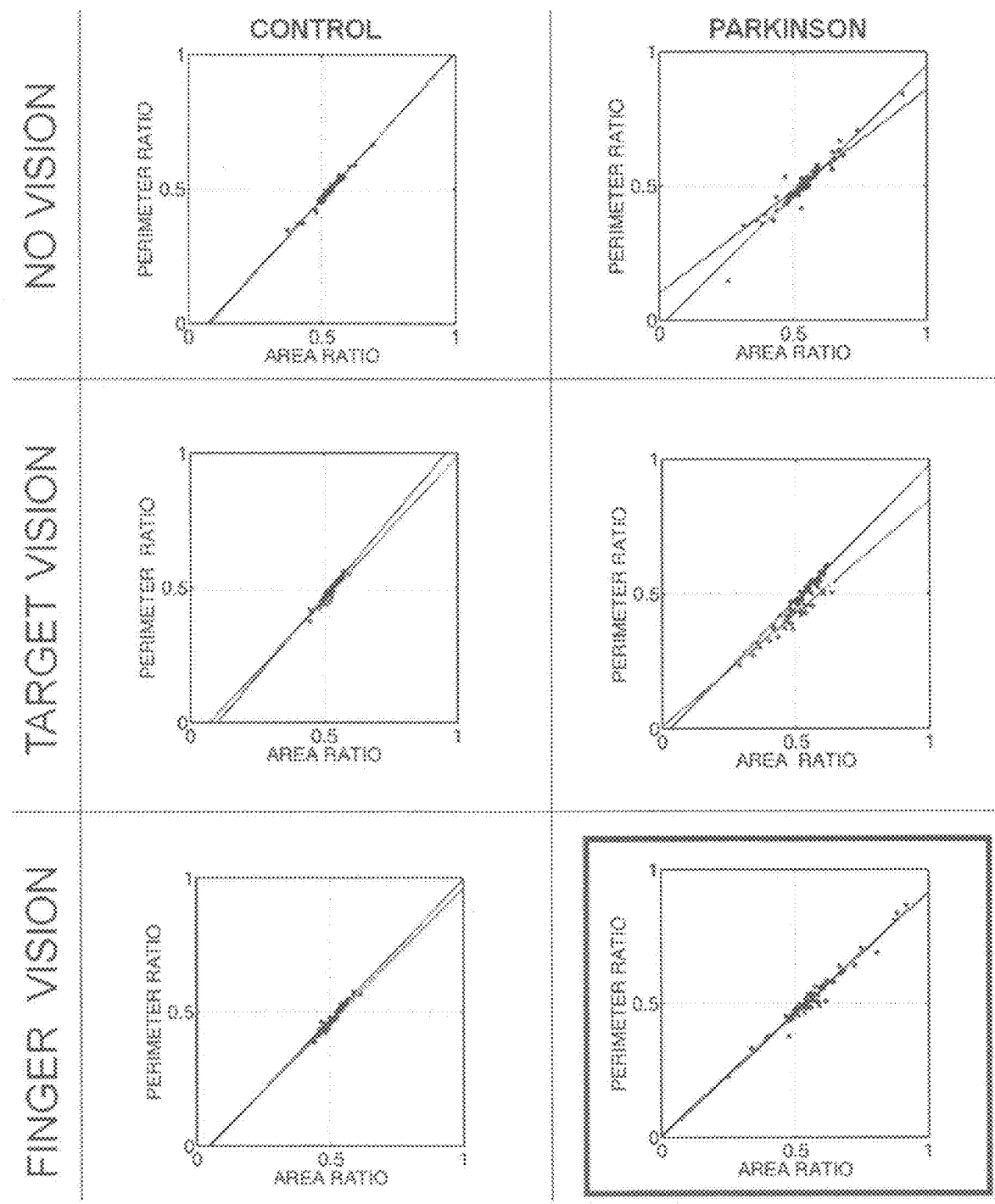

The Friedman's test revealed that in the No Vision condition, the area and perimeter ratios for the forward motions in the participants with PD were not significantly different from those of the NC subjects ($p=0.67$; $x^2_{df=1,6}<0.18$; mean ranks, [6.70, 6.30]; unlike the ratios for the backward movement trajectories). The distributions and regression lines are depicted in FIG. 24 for each condition. Notice that the ratios were more variable in the PD case (broader scatter at ~½, but still the two ratios significantly covaried linearly in the forward case). The linear regression lines in the PD case had different slopes than those of NCs, indicating that, across trials and target locations, there was conservation of the intended hand displacement when such displacement transformed into a postural displacement.

With vision of the target, the ratios of the participants with PD were significantly different from those of the NCs in both the forward and backward motions ($p=0$; $x^2_{df=1,6} \leq 43.5$, mean ranks, [9.07, 3.93]). The patients with PD shifted the perimeter ratio distribution to a value significantly lower than ½ (t test, $p<0.01$) in the forward case, implying poor integration of the visual cues and the kinesthetic feedback when prompted to rely more on the external target for guidance.

In the Finger Vision condition, there were no significant differences in the ratios between the NCs and the PD patients ($p=0.29$; $x^2_{df=1,6} \leq 1.15$; mean ranks, [5.96, 5.04]), suggesting stronger similarity between the forward and the retracting strokes than in the other cases. Notice also that as in the normal controls, the patient's trajectory ratio value was close to ½ (two-tailed t test, $p<0.01$). This condition improved the performance of the patient in the retracting segment, yet the scatter from the retracting trajectories was more variable. This implies that in this stroke, the transformation from visual to kinesthetic coordinates did not conserve the desired hand displacement under coordinate change to joint angles. The joint angles in this condition were more variable and had a prevalence of the task-incidental DOF that contributed to the violation of the symmetry in several trials.

Retracting Motions
Trajectories

Figure 25:
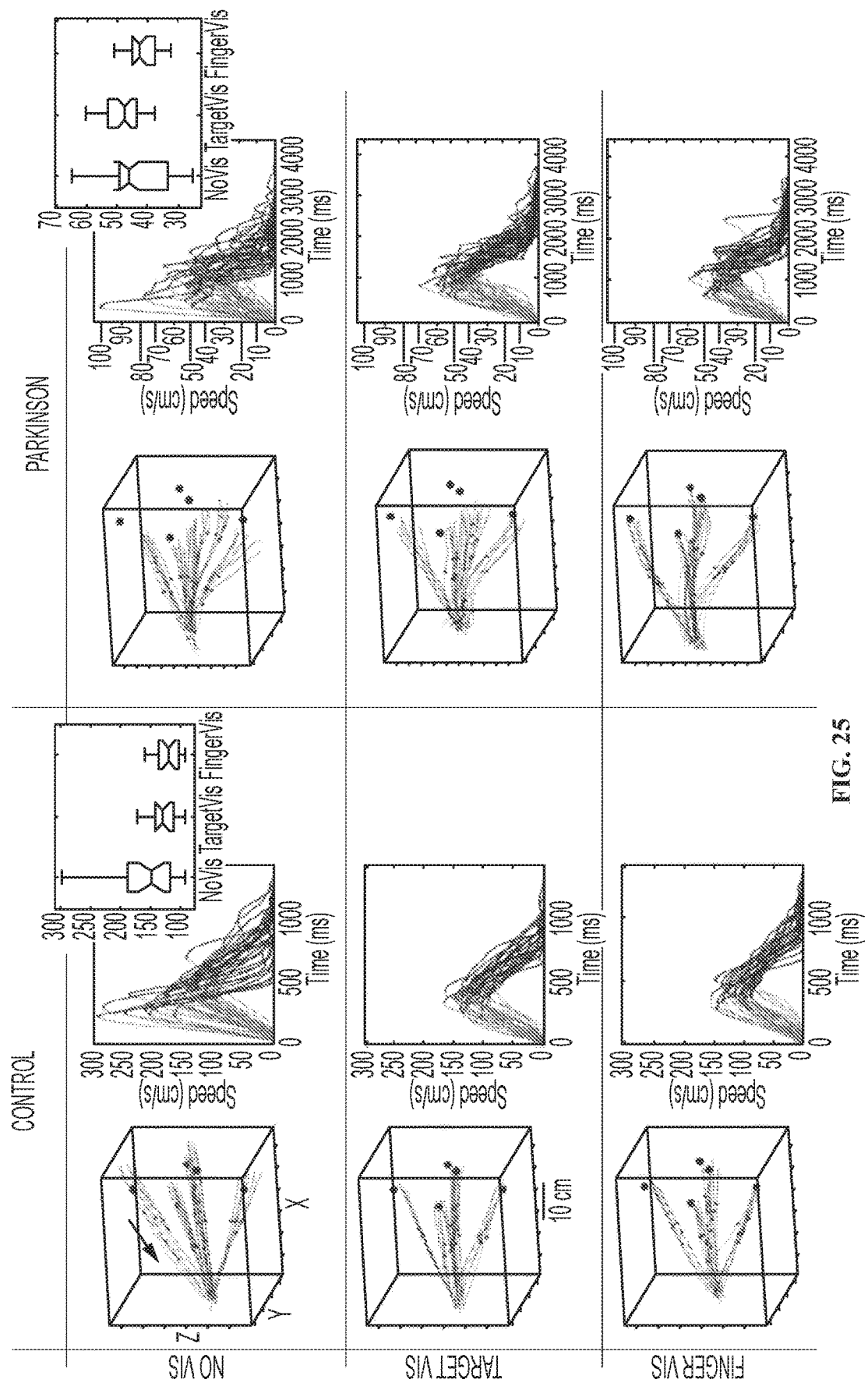

The NCs improved the retracting trajectories both with vision of the target and with finger vision, but in the finger vision case, the trajectories were less variable and straighter overall. This can be seen in the first column of FIG. 25. FIG. 25 shows that the PD participant, who is representative of this group, had highly variable and curved trajectories when retracting the hand toward the body. This participant, however, demonstrated that both target vision and finger vision improved performance on average for the retracting stroke. In addition, in the PD group, vision of the finger throughout the movement shortened the movement latency compared to continuously viewing the final target. Although the peak velocity during vision of the target was on average higher in this typical PD participant, he actually slowed down the ending of his backward motions toward the final posture with a long tail in the speed profiles. This contributed to the increase in variability of the retracting postural path in this condition. This can be appreciated in the last column of FIG. 25, where the insets show that in both the NCs and the patients there was a significant effect of the form of sensory guidance on the values of the peak velocity (NC, $p<10^{-5}$; PD, $p<0.004$). These speed effects in the NCs did not change the retracting postural path and the final posture. By marked contrast, the speed effect on the retracting trajectories altered the postural paths and the final posture of the patients with PD.

End Position Postural Error

In the retracting trajectories of the arm, the end postural error was examined instead of the end point variability in visual space. This is because the target in the retracting reach was proprioceptive, to reproduce the initial posture. It was also desirable to know the extent to which the system with PD failed to maintain the continuity of the retracting postural path congruent with the history of the forward postural path in the face of changes in sensory guidance that altered the speed. Since the final posture was instructed as a goal of the task, the retracting path was highly constrained by the desired final orientations of the arm (the plane of the arm) and by the final orientation of the hand. Thus, despite expected higher variability in the retracting path with changes in sensory guidance, typical performance had to lead the arm along similar retracting postural paths across sensory-guidance conditions. As a result of the instructions, the retracting path had to end in a similar final posture—if the system was compliant with the task demands Although the NCs manifested consistency in the postural paths back to the instructed final posture, this was not the case in PD patients, who altered both the retracting postural path and the final posture with the speed changes; yet, as expected, the conservation of the postural path and of the final posture manifested in the NCs.

Trajectory Ratios

The Friedman's test revealed that in the patients with PD, during the backward movement, the ratios in the three conditions were significantly different. However, in the Finger Vision condition, PD participants and the NCs had similar ratios ($p=0.12$; $x^2_{df=1,6} \leq 5.1$; mean ranks, [6.23, 4.89]). The effect of finger vision on the PD case can be seen in FIG. 24, second column and third row, where both distributions showed a similar slope and intercept. Note that this is not the case for the patients with PD in the No Vision and in the Target Vision conditions.

Incidental/Task-Relevant DOF Ratios

Figure 26A:
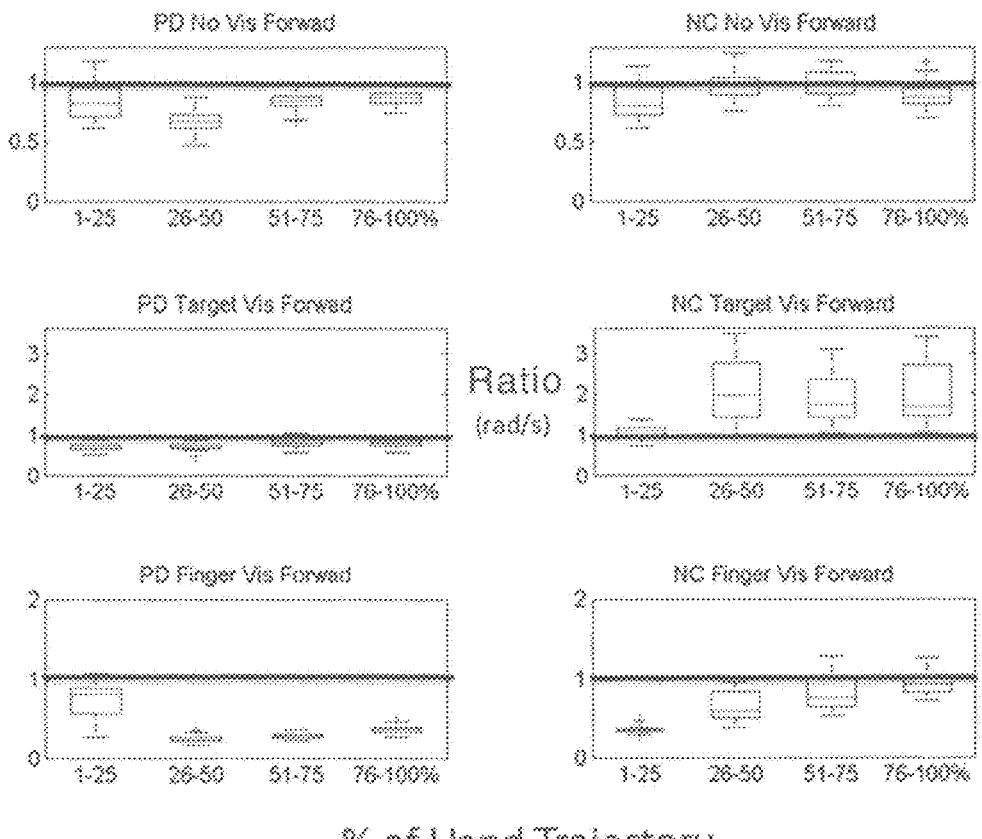

FIG. 26A shows the results of the ANOVA on the incidental/task relevant DOF ratios for the forward stroke of the reaching movement. Recall that ratios <1 indicate a predominance of task-relevant DOF, suggesting voluntary control, whereas ratios >1 indicate prevalence of task-incidental DOF, suggesting more automated motions.

Significant task performance differences were found between the NCs and the participants with PD. In their forward reaches, the patients with PD had a ratio <1 across all conditions, indicating abnormal voluntary monitoring of the goals. In contrast, the NCs modulated this ratio as a function of the form of sensory guidance. However, notice that the forward reaches with vision of the target was the condition that showed the most marked differences between the patients with PD and the NCs. In this condition, the ratios for the NCs were 1 in the first 25% of the path and >1 in the rest of the path. This result suggests that the NCs initially balanced the DOF, but the rest of the path was automated with a prevalence of the task-incidental DOF (ratio >1). In contrast, the patients with PD during the Target Vision condition showed a ratio <1 throughout the path, suggesting that the voluntary DOF dominated all throughout. Likewise, in the No Vision condition, the NCs showed some balanced ratio of 1 throughout the path (from 25-75% of the path) that was absent from the patients with PD. In the condition where the finger guided the movement, both the NCs and the patients with PD had ratios <1, suggesting that voluntary monitoring dominated the guidance in both groups. This was the forward reach condition where the performance between the NCs and the patients was qualitatively closest, albeit quantitatively (statistically) different. The qualitative similarity between the NCs and the patients with PD in the pattern of joint-angle recruitment/release and in the balance between voluntary and automatic control during the finger guidance condition is congruent with the changes seen in hand-level control, in the area-perimeter ratios in the hand trajectories and in end point accuracy of the hand space. These changes in PD hand trajectories and end point accuracy with finger guidance were significant and toward the normal levels. Yet, no full recovery was quantified at any level. In particular, the joint-angle-level control in the patients with PD suffered more than the hand-level control.

Figure 26B:
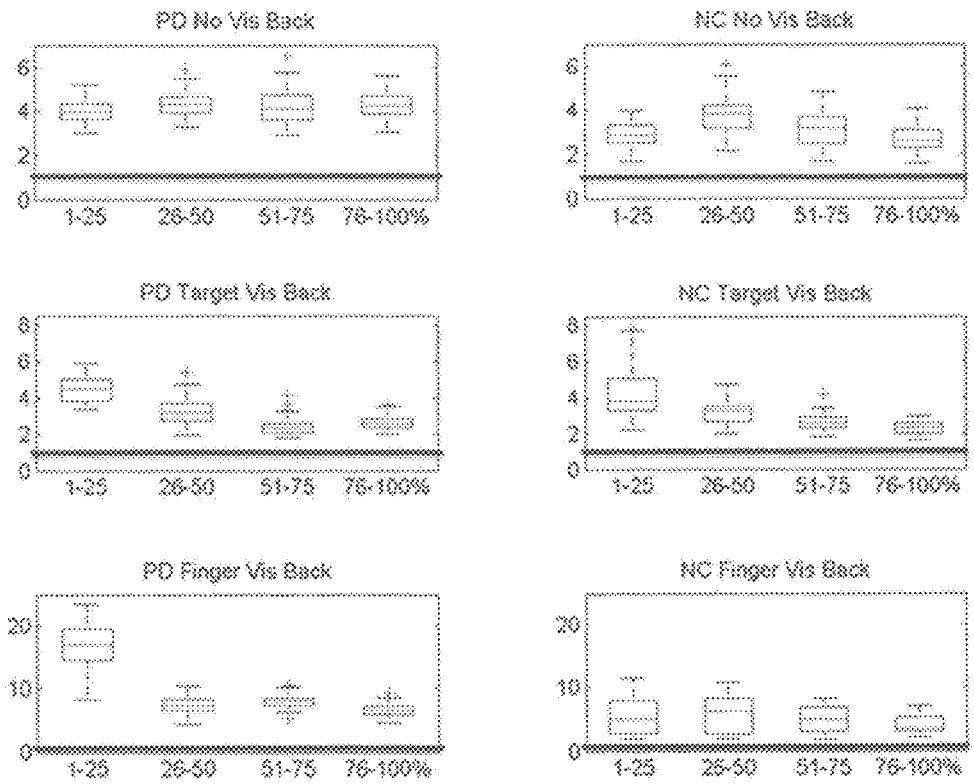

The aberrant interactions in PD extended to their movements back toward their body with a ratio >>1, indicating abnormal reliance on the task-incidental DOF. This is depicted in FIG. 26B, where significant differences in the variability of the NC ratios were found between the last two segments of the path (Kruskall Wallis test $p<0.01$) but were not present in the participants with PD. The NCs and the participants with PD showed the largest differences in the No Vision condition, whereas both the target and the finger visual guidance gradually changed the ratio toward 1 in both groups. Quantitatively, the two groups still significantly differed in the second half of the path. However, some improvements toward typical patterns were captured that coincided with the improvements observed in the end point errors at the hand-trajectory level (the point in space where the retracting reaches initiated from) during both conditions.

In summary, the NCs demonstrated marked differences in the DOF recruitment, release, and balance ratio between the forward and retracting paths. In the forward reaches, the condition in which performance of the participants with PD was closest to that of the NCs was when they were using finger guidance. During this condition, both the NCs and the participants with PD showed a prevalence of task-relevant DOF (voluntary monitoring the reach). In the retracting segment of the reach, both groups showed ratios >1 (prevalence of automated task-incidental DOF), with the No Vision condition showing the largest difference between the PD patients and NCs. The largest difference between PD patients and NCs in joint space is congruent with the pattern between groups in end point errors in this condition, where there was the largest difference in accuracy between groups, and with the area-perimeter ratios, which had the largest slope differences in this condition as well.

Example 10

In PD at different stages of the disease both motor and cognitive impairments emerge (Lee et al. (2012) Can. J. Neurol. Sci., 39:473-482; Paul et al. (2012) Neurorehabil. Neural Repair, PMID: 22623207). Patients with PD lose the delicate balance between different levels of voluntary control at different stages of the disease progression (Redgrave et al. (2010) Nat. Rev. Neurosci., 11:760-772). These levels are also affected by the ways in which objects (Schettino et al. (2003) Exp. Brain Res., 151:158-166) and the context of a task (Tunik et al. (2004) Mov. Disord., 19:897-906) constrain movements of the reach-to-grasp family. Yet, cognitive and motor impairments are often confounded in PD. Here a priming task is designed to dissociate aspects related to higher motor complexity (such as the demand of additional physical rotations of the joints) from aspects related to higher cognitive-spatial demands involving decisions and selections of object-hand's affordaces.

Early on during the course of the disease, areas of the caudate and rostral putamen that mediate voluntary control (Middleton et al. (2000) Brain Cogn., 42:183-200; Middleton et al. (2000) Brain Res Brain Res. Rev., 31:236-250) are relatively spared from the degenerative process (Yin et al. (2004) Eur. J. Neurosci., 19: 181-189; Yin et al. (2005) Eur. J. Neurosci., 22:505-512; Yin et al. (2005) Eur. J. Neurosci., 22:513-523). However, the loss of dopamine in the posterior regions of the putamen—a region associated with automatic control (Albin et al. (1995) Trends Neurosci., 18: 63-64; Chevalier et al. (1990) Trends Neurosci., 13:277-280)—leads to deficits in automated arm-postural control when patients are off their dopaminergic medication, particularly between forward and retracting reaches. Since the gradual dopamine depletion affects the automated motor performance and slows down the movements (DeLong et al. (2009) Parkinsonism Relat. Disord., 15:S237-240; de Wit et al. (2011) J. Cogn. Neurosci., 23:1218-1229), it is possible that increases in cognitive spatial-demands from continuously monitoring the movements also contributes to bradykinesia. It is however unknown if the breakdown would be gradual and detectable in the random fluctuations of kinematics parameters as a function of orientation-priming, or if the stochastic motor patterns would be insensitive to orientation-priming. Here a disruption in PD of the spontaneous control of speed during hand retractions is reported. This impairment was only present during orientation priming and independent of the motor-postural path. This dissociation makes orientation-priming a good candidate to assess in PD latent cognitive deficits before they surface.

Methods

A heterogeneous cohort of 17 patients with PD at different stages of the disease was examined. The patients were at the off-time of their medication (the time of the day when their medication had worn out). Patients were scheduled on an individual basis and accompanied by a care giver. None of the patients were treated for symptoms of depression. One patient reported compulsive gambling in the past but the symptoms disappeared when switching to new medication. Three of the patients had undergone a Deep Brain Stimulation (DBS) procedure years ago and were tested with the DBS ON but off their medications as well. Records were obtained for all but 6. They were evaluated by the Neurologist using the Unified Parkinson's Disease Rating Scale (UPDRS, average score was 26.18, ranging from 13 to 42). Patients for whom records are missing were diseased by the time that the tests were re-administered or had moved to a different state. The UPDRS scores provide a separate qualitative evaluation useful to gain an idea on the stage of the disease according to the gold standard of PD; but they in no way change the objective results. 5 normal controls (NCs), 2 males and 3 females ranging from 44-69 years of age, were also tested.

Participants performed an orientation-matching task in a continuous forward-and-back loop while seated comfortably in front of a computer monitor. They held a rod in their hand resting it on the table. The task was to move the hand towards a virtual rod presented at 1 of 5 possible locations on a computer screen and orient the hand so as to match the principle axis of orientation of the virtual rod with the hand-held rod. Two canonical orientations were used: vertical and horizontal. On the rod the desired speed was instructed with text, and also prompted with color (red for slow and green for fast).

In one case (DEFAULT) the movement was a biomechanical act devoid of the need to make a decision about possible hand configuration to match the target spatial orientation. The participants freely chose the final hand orientation. In the other version, primed-UP, orientation priming was used in such a way as to have identical biomechanics as those of the DEFAULT case. However the priming evoked decision making so the participant had to weight different possible hand configurations—all aligning with the spatial target orientation—but choose the one that the priming constrained. The picture of a coffee cup was used to instruct the desired target orientation and to prime the appropriate hand configuration. The participant was then asked to "gesture the final orientation of the hand as if reaching for and grasping the cup to drink from it".

A second version of the orientation priming was also used—opposite in orientation to the primed—UP (and DEFAULT) but still aligning the hand along the canonical principle axis of orientation. Because of the abundant degrees of freedom of the arm, it was possible to fully rotate the hand and match the cup handle in a completely different manner from primed-UP and DEFAULT while aligning it to the same canonical axis. This hand configuration required to end at a more complex orientation than the primed-UP (DEFAULT), one that required additional rotations and translations of the arm joint angles and of the hand.

Five positions of the virtual rod were used, one in the center and four at each of the 4 corners of the monitor. 20 trials in each block (2 speeds×5 positions×2 orientations) was used with 5 repetitions of each block. Endpoint accuracy was not enforced since the patterns of variability of speed and acceleration were studied as the movement unfolded in the continuous forward and back loop. Trials were randomized and balanced according to the combinations of position×orientation×speed within block.

The interplay between the task-relevant and the task-incidental dof changes as a function of task difficulty. The DEFAULT and primed-UP cases have on average similar postural rotational biomechanics. However, the primed-DOWN condition demands on average different joint angle recruitments. The joint angle decomposition of the postural excursions is from methods developed in Torres et al. (J. Neurophysiol. (2002) 88:2355-2367) and hereinabove.

These methods decompose 7 of the dof of the arm into those which are relevant to the task goals and those which are incidental to it. In the forward motions the task-relevant dof tend to dominate over the task-incidental components if the motion is more challenging—as in the vertical cases; then the hand retracts in "auto-pilot" mode, i.e. the task-incidental dof tend to dominate. This is the typical behavior of the normal system for DEFAULT and primed-UP with identical biomechanics demands With regard to the differences in the recruitment of the dof for the primed-DOWN cases in relation to primed-UP and DEFAULT, both vertical and horizontal versions the task-relevant dof tend to dominate over the task-incidental dof.

Results

All participants alike—NC and patients—maintained the instructed speed in the forward segment. However, unlike NC who maintained the speed of motion continuously in the forward and back loop, the patients with PD manifested a discontinuity in the speed control. This discontinuity manifested gradually along a gradient of severity as a function of the spatial-orientation priming complexity and as a function of the years since the diagnosis. The longer the patient had had the diagnosis, the higher the impairment in the speed control during retractions. Spatial-orientation priming did not facilitate the control of speed in PD. On the contrary it impeded the continuity and fluidity of this control in the spontaneous retractions of the reach-to-grasp motions.

For the primed-DOWN case the Mann-Whitney U test revealed two subgroups within the cohort according to the level of significance in statistical difference of the retracting speed maxima between fast and slow. The patients with the $p>0.05$ (denoted PD1) provided evidence for losing their distinction between fast and slow speeds in relation to patients with $p<0.05$ (denoted PD2).

The PD2 group was able to maintain the instructed speeds in the primed-UP condition during task-incidental retractions while the PD1 group lost their control over the instructed speed in this condition. Likewise, PD1 happened to have been diagnosed more than 6 years ago, while PD2 had been diagnosed on average less than 6 years ago. The diagnosis length was not a pre-designed hypothesis but rather a self-emergent pattern from the speed maxima separation yielded in the retracting motions during the more challenging primed-DOWN condition. All but 1 had over 6 years of diagnosis (average 8.28+/−2.21 years since diagnosis, range 3-20 years with average UPDRS 29.57+/−10.09, range 13-42). The PD2 group had below 6 years of diagnosis, average 2.7+/−1.7 years since diagnosis and average UPDRS 20.25+/−9.8, range 9-29). Including the DBS patients as part of the PD2 group or leaving them out did not change the reported differences between groups.

Despite the similarities in required kinematics between DEFAULT and priming conditions, significant differences in the patients' hand trajectories of these two conditions were found that were absent in the NC. The speed effects that gave rise to the two subgroups of patients above, also extended to the linearity metric detecting deviations from the straight line in the hand trajectories.

The differences in path curvature (trajectory bending) for primed-DOWN were also observed in some of the patients with PD, but those in the PD1 group had mixed effects of priming on the bending of their wrist trajectory. Their trajectories lost the distinction in curvature that NC had shown. In 12/17 patients the effects were comparable to those observed in the NCs. These patients showed similar ranges in the forward and retracting bending. The other 5 patients had modest systematic effects across DEFAULT and priming conditions ($p<0.15$), yet the bending of their trajectories was higher than NC (median forward 7.33 cm, and 13.7 cm in the retracting segments).

Figures 29A, 29B, 29C:
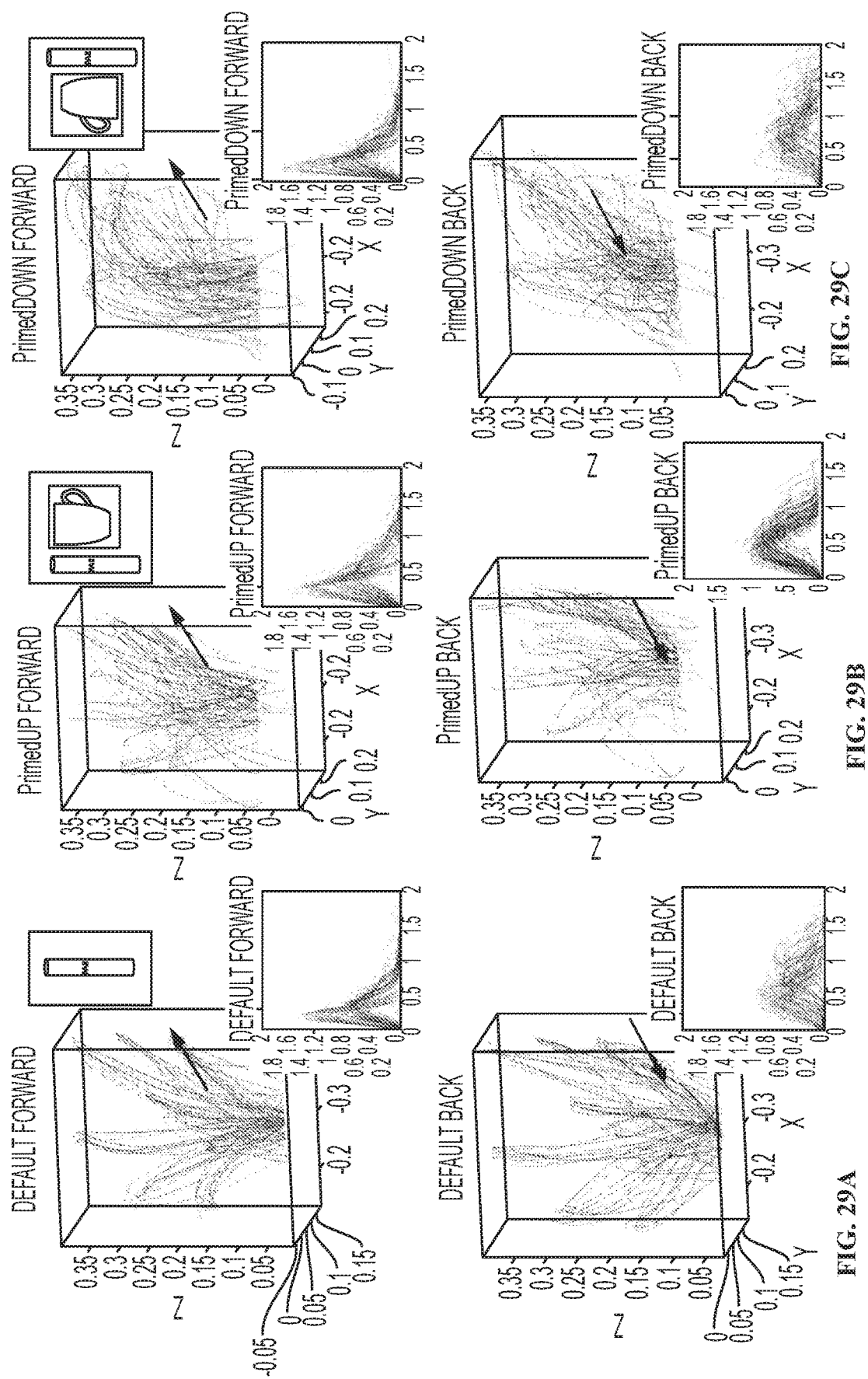
FIG. 29A through FIG. 29C show the effects of priming on the movement trajectories at the wrist in typical patient within PD1 group using two different levels of speeds randomly cued.

Notice that across patients the differences in the geometry of the hand paths were not as revealing as those found in the temporal dynamics, which gave rise to the two subgroups within the cohort. The trajectories from a representative NC are depicted in FIG. 27A through FIG. 27C. The trajectories from a representative patient in the better-off PD2 group are shown in FIG. 28A through FIG. 28C. Notice the increased variability of the trajectories in general for the patients. In particular, notice the differences between the primed conditions and the increase in variability for the representative in the worse off PD1 group shown in FIG. 29A through FIG. 29C.

The clustering analyses revealed in the patient cohort systematic differences in the values of speed maxima as a function of cognitive load that confirmed the subgroups that had emerged from the statistical significance test. FIG. 30A and FIG. 30B shows the scatters and the slope values of a linear regression fit. During the DEFAULT case NC and patients in the PD2 group clustered their slow and fast speed values within non-overlapping aggregates between the forward and the retracting cases. All NCs and patients maintained the instructed speed during the voluntary segments towards the target. Hence relatively large separations between the means of the fast and slow speeds along the horizontal dimension (forward segment) were quantified. In all NCs, the instructed speed was continuously maintained throughout the retracting motions as well. The differences between speed in NCs and patients were significant for both forward (median 1.42 m/s vs. 1.85 m/s, Ranksum test $p<0.11\times10^{-7}$) and retracting (median 0.99 m/s vs. 1.55 m/s, Ranksum test $p<2.61\times10^{-12}$) motions.

In marked contrast to NC and patients in the better-off PD2 group, the patients in the worse-off PD1 group revealed overlapping of the scatters with no visible distinction between the slow and fast trials. Likewise during primed-UP patients in PD1 showed more mixture in their scatters that no longer distinguished fast from slow speeds, particularly along the vertical axis denoting the retracting segments. During primed-DOWN these deficits in speed control were exacerbated in the patients. Both PD1 and PD2 were affected by the more complex requirements of primed-DOWN (Ranksum test for each subject, mean p value 0.19+/−0.17, range 0.074-0.56).

The slope of the scatters systematically changed across conditions and between the two patient subgroups consistent with the statistical significance previously separating the two subgroups within the cohort (FIG. 30A and FIG. 30B). This result ruled out a uniform slowdown of the motion as the exclusive link to the changes in speed. The cognitive load conditions modulated the relations between fast and slow speed differently for each patient type and for the NC's.

There were significant differences between the value of the speed maxima of the slow and of the fast trials across all patients during the voluntary forward reaches (PD1 vs. PD2 median 0.55 m/s vs. 1.56 m/s (slow); 0.92 m/s vs. 1.79 m/s (fast)).

Both PD1 and PD2 groups maintained the instructed speed during voluntary forward motions in both primed and DEFAULT conditions (Ranksum test for each subject, mean $p<10^{-4}$, +1-0.0016, range $10^{15}$-0.00054). Yet, both PD1 and PD2 groups could no longer maintain the instructed speeds during the task-incidental retractions for the most difficult primed-DOWN condition that required additional rotations of the arm joints The PD2 group maintained the instructed speed during the task-incidental retracting motions in both DEFAULT and primed-UP conditions. The maximum speed values were significantly different between the slow and fast speed trials (median 0.65 m/s vs. 1.15 m/s, $\chi^2=215.05$, $p<10^{-48}$). The instructed speed in the PD1 group, however, was no longer distinguishable when the target orientation was primed-UP (median 0.58 m/s vs. 0.61 m/s $\chi^2=0.86$, p >0.5). The overall speed maximum was significantly different between the PD1 and PD2 groups for both the primed-UP and the primed-DOWN cases. PD2 were significantly faster (Kruskal-Wallis ANOVA $\chi^2=216.24$, $p<5.8\times 10^{-49}$).

These differences in the distinctions of maximal backward speed values between PD1 and PD2 could not be accounted for by the time to reach the maximum speed during the task-incidental retractions, as these were indistinguishable between the two groups (median 0.52 s, $\chi 2=2.86$, p >0.1) in marked contrast to the NCs (median 0.35 s, $\chi 2=122.5$, p<10-27). These marked differences in cognitive-load effects on speed variability between PD1 and PD2 are shown in FIG. 31A and FIG. 31B for the maximal values of the speed (m/s) and for the time (s) to reach those values in the primed-DOWN cases.

In subsequent experiments, each patient of the cohort was treated as a "case study". PD is a heterogeneous disorder because the progression of the disease is different even for people with the same number of years since their diagnosis. The clustering methods used here permit the blind classification of different self-emerging subtypes within this cohort so as to better understand the underlying statistical properties of each PD subtype. The speed and acceleration variability were extracted across trials and conditions the stochastic signatures of each self-emerging subgroup according to the clustering analyses and also according to the blind misclassification analyses. This analysis confirmed that indeed these subgroups were two different statistical classes. Each of the patients in the subgroups contributes to the overall stochastic signature of the aggregate data making up that subgroup. The subgroups were not picked according to some feature. They rather automatically emerged from the data using blind k-means clustering. Confusion metrics were also used to automatically reclassify the groups based on the veridical data and found 100% confirmation of the blind classification outcome and of the sub-grouping based on the p-values from the statistical comparison separating PD1 and PD2 patients according to the significance of the effects of cognitive load on speed compliance.

Distinct stochastic signatures of variability in speed maxima between PD1 and PD2 was found (frequency histograms in FIG. 32A and FIG. 32B). Using maximum likelihood estimation (MLE), the frequency distributions of the speed maxima from the aggregate of retracting trials from patients in each subgroup were well fit with 95% confidence by the parameters of the continuous Gamma probability distribution family Patients in the PD2 group distributed in the skewed range of the Gamma distribution family (closer to NC) manifesting a multiplicative effect of the orientation priming on the overall variability of their retracting speed.

The MLE (a,b)-Gamma estimates for the PD2 was (a=7.3, b=0.120) with [6.74, 8.02], [0.11, 0.13] 95%-confidence intervals. Bottom Panels of FIG. 32A and FIG. 32B show skewed distributions of the maximum acceleration in the PD2 groups. For the maximum acceleration the MLE (a,b)-Gamma parameters were (2.75, 1.40), with confidence intervals [2.5, 3.02], [1.26, 1.56] for PD1 and (2.75, 1.98), [2.53, 3.0], [1.80, 2.17] for PD2.

In marked contrast to the PD2 and to the NC, the patients in the PD1 group were well fit during prime-UP by a symmetric distribution towards the normal range of the Gamma. This shows additive effects of cognitive loads on the variability of the retracting speed maxima. The MLE yielded shape (a=15.7) and scale (b=0.040) estimates for the maximum speed with [14.2, 17.3] and [0.03, 0.045] 95%-confidence intervals respectively.

The primed-DOWN condition evoked very different trajectories across all joints, an effect shown on the top panels of FIG. 32B. The arm was more abducted in primed-DOWN than in primed-UP (FIG. 32A) with longer and more variable elbow excursions that ended with a different orientation of the hand—as required by the priming stimulus. The MLE Gamma distribution parameters were (a=12.8), scale (b=0.050) for the maximum speed with [11.61, 14.20] and [0.04, 0.055] 95%-confidence intervals respectively. The PD2 had very different MLE for the distribution of maximum speed (a=6.3, b=0.120) with [5.8, 6.91], [0.127, 1.153] 95%-confidence intervals.

Across patients in the PD1 group, the distribution of maximal speed values was nearly symmetric, and was centered at lower values than those of the distribution of the PD2 group, in congruence with the box plots shown in FIG. 31A. In PD2 the (a,b)-Gamma distribution parameters and confidence intervals were different from those of PD1. For PD1, the mle (a,b)-parameters had values in the Gaussian range of the Gamma. In contrast, the distribution in the PD2 case was skewed.

The MLE values for the (a,b) parameters of the Gamma probability distribution family were determined for each subject. Linear fit characterized differences in the scatter of points (participants) across priming conditions with different slopes and intercepts for primed-UP (NC 0.91, 2.0; PD1 0.83, 2.03; PD2 1.25, 2.9) respectively and R-square, rmse: (0.44, 0.04; 0.80, 0.0095; 0.66, 0.05) respectively. For primed-DOWN (NC 1.03, 1.98; PD1 1.39, 2.46; PD2 0.90, 3.02) respectively and R-square, rmse: (0.40, 0.05; 0.61, 0.01; 0.5, 0.04).

Example 11

Movement variability embedded in cognitively driven task such as those requiring decision making offers a great advantage over purely observational inference-based methods that currently dominate the fields of development and cognition. Variability forms a gradient according to types of task functionality: intended, automatic or autonomic, a gradient which the mature system flexibly navigates through on demand. The present work investigates somatosensory-motor variability as re-afferent input, measured at the motor output across development in instances where the movement is performed biomechanically, devoid of cognitive loads and cases in which the same movement is performed in the context of decision making A unifying framework is provided to objectively measure the coupling of movements and cognitive processes as a function of task functionality. Here, it is shown that movement-output variability and its kinesthetic sensation give rise to a scaling psychophysical power relation. This relation holds across individuals of various ages and unambiguously distinguishes simple biomechanical from cognitively driven actions. This power law unveils the course of a maturation process that distinguishes different levels of intentionality.

Parameters of Interest

Somatosensory-motor parameters included the maximum value of the speed (m/s) and time (s) at which this occurred (computed in each trial); the time-normalized path length (m) obtained from the movement onset to the pause. In each trial, the instantaneous speed magnitude traveled by the hand from the movement onset (as the speed steadily increased) up to the target location (when the movement stopped) was summed and then divided by the duration of the movement (s). The duration is the number of frames in a segment divided by 240 because the sampling resolution is 240 Hz (frames per second). Overall segment length over segment time is the trial-average hand speed. This parameter was also obtained as the hand moved away from the target until its first pause, revealed by the retracting speed profile. Importantly, to remove allometric effects of body-size across ages, the normalized peak velocity (the peak velocity divided by the sum of the peak velocity and the averaged trial speed) was gathered in each trial (Lleonart et al. (2000) J. Theor. Biol., 205:85-93).

Cognitive parameters included the accuracy of the decision in the match-to-sample task (measured as the % correct) and the decision movement latency (s). To obtain the latency parameter, the time (s) from the onset of the stimulus (evoked by the participant touching the bottom-center of the screen) to the screen touch at the targeted choice was measured. The movement decision time includes the reaction time, the time spent deciding and the actual movement time. Subtracting the movement time (which the speed profile yields between the two relevant minima) provides the latency of the movement decision (s). Changes in accuracy and latency over time were measured by obtaining the difference between the first 150 trials and the 150 later trials for each subject. Non-parametric statistics were used to assess significance, as the distributions of these parameters were skewed. Furthermore, in the children <4 years of age the log-transformed of the speed data failed the normality test (Chi-square goodness of fit test in MATLAB rejected null hypothesis of normality at 5% significance level).

It is important to note that, unlike traditional significance hypothesis testing methods, the new methodology does not assume homogeneity of the sample under a common probability distribution. It cannot possibly do so as somatosensation which is what was measured is an individualized experience. Instead of grouping subjects a-priori to assess treatment outcomes or effects within and between groups, the present method uncovers the probability distribution for each individual subject that best characterizes his or her inherent micro-movements' variability. Then, any commonality in the sample will automatically aggregate to form self-emerging clusters. Such automatically formed clusters are thus indicative of different statistical classes according to the somatosensory read out of the micro-movements. In other words, people with similar somatosensation will automatically cluster together. Individuals with different somatosensorymotor patterns will automatically fall in different statistical classes. Thus, because of the underlying assumptions of significant hypothesis testing, it would be a major flaw to homogenize the behavioral data a priori and test the null hypothesis. Different people have somatosensation that is described by extremely different probability distributions.

Distribution Analysis

Herein, MLE techniques with 95% confidence regions for each (a,b) Gamma parameter were used and the same participant was assessed during different variants of the pointing task under different contexts and stimuli. Shifts in the stochastic signatures of a velocity-dependent movement trajectory parameter from pointing may be used as the system flexibly re-adapts to different stimuli while performing a basic pointing task with similar kinematics demands.

Other parameters could also be used. The shift from condition to condition is unique to each person. A shift to the right indicates positive gain, a change towards the Gaussian (symmetric) range of the Gamma with higher predictive power than a shift to the left. A shift to the left indicates negative gain—towards the Exponential range, with no predictive power (prior movements are not contributing in a systematic and predictive way to future movements). These real-time stochastic trajectories permit one to funnel out through the movement's random fluctuations the stimuli that best shifts the person's somatosensation towards a verifiable percept with predictive power.

As the system flexibly re-adapts between task conditions the signatures shift the (a,b) values. The shift may be represented by a line connecting the dots, where each dot represents a measurement of the stochastic signature (across hundreds of trials) of the same subject for a different variant of the basic task. For example, one can measure the shift from the baseline biomechanical pointing to the decision-making pointing gesture due to the match-to-sample of geometric shapes, and then due to a more complex pattern involving rotations of objects. The subject may reshape the signatures of intended pointing at a faster rate between the match to sample using rotations than using geometric shapes. Thus rotation-related stimuli may be more effective in this subject than stimuli involving geometric shapes in the sense that the signatures become more predictive (i.e. they shift positively towards the Gaussian range of the Gamma plane). If the subject instead changes the signatures maximally along the scale axis, this indicates a gain in the height of the distribution with a modest change along the shape axis. This implies that the movement segments intended to point at the correct targets are not changing much their predictive power with respect to the movement speed. By marked contrast the incidental motions of this same subject may clearly reveal that the rotation-related stimuli take the motions away from the symmetric ranges of the Gamma plane. This indicates a negative shift along the shape axis towards the more random ranges with an increase in the noise of the variability of the random process.

This method enables one to dynamically build a stochastic trajectory to express shifts in somatosensory-motor patterns as a function of task demands, cognitive loads and various task contexts, etc. In this way it is possible to chart the individual's somatosensory-motor capabilities and cognitive predispositions. More importantly it is possible to funnel out the best type of stimuli for each child. These could include different sources of sensory guidance, so as to identify which sensory stimuli would result in more predictive behavior. One can thus readily quantify the shifts towards predictive ranges and build stochastic trajectories that would optimally lead the person towards the proper regime of predictability.

The stochastic signatures of the somatosensory-motor integration process were estimated for each participant using various parameters in the movement trajectories and in the cognitive (decision-making) domains. The scatter of points was colored by age. This produced self-emerging clusters which were used to obtain an ensemble plot of the points on the Gamma plane for both the forward and retracting segments. An exponential relation between the scale and shape parameters was revealed and a power fit was performed in each case using the general model $f(x)=mx^n$. Finally both experimental groups were compared on the biomechanical pointing task using the normalized peak velocity to remove allometric effects of body-size across ages. This control experiment was used to investigate across ages the empirical statistical properties of the unveiled distributions.

Results

Each participant in the first group exhibited a unique stochastic signature of their average speed according to the MLE of the (a,b)-Gamma parameters depicted on the Gamma plane of FIG. 33B. The points were color-coded by age. Notice here that self-emerging, non-overlapping clusters appeared. The ensemble data from each self-emerging cluster is plotted in the form of normalized frequency histograms in FIG. 33A. Note that the children below 4 years of age start out with an Exponential distribution. This is important because the Exponential distribution is a continuous, memory-less, random distribution. The empirically obtained distribution suggests that, at this age, the average speeds of prior movements are not yet contributing in a systematic and predictive way to the average speeds of future movements. The patterns of motion are mostly random. By 4-5 years of age however, the stochastic signature transitions into a skewed distribution with multiplicative effects (Limpert et al. (2011) PLoS ONE 6, e21403; Limpert et al. (2001) BioScence 51:341-352.). In the case of the college-level young adults the empirically obtained distribution is symmetric with additive effects. These patterns suggest that as one matures the motions become more systematic and acquire higher predictive power from trial to trial. The result also demonstrates that the continuous Gamma probability distribution family characterizes well the human continuum of proprioceptive development insofar as average speed is concerned.

A power fit was found through the trial-average speed stochastic signatures of each self-emerging cluster for the forward and retracting segments spanning from children below 4 years of age to college age. The general model $f(x)=mx^n$ was used with m=0.028 and n=−0.420 with 95% confidence intervals [0.025, 0.030] and [−0.492, −0.347], respectively. The goodness of fit parameters were SSE=4.63×10$^{-6}$, $R^2$=0.992, adjusted $R^2$=0.991 and RMSE=0.0010076.

The clusters characterized by this line span several orders of magnitude. They serve to blindly characterize the human continuum of the typical somatosensory developmental trajectory from 3.5 years of age to 30 years of age. This line also serves to quantify deviations from it.

For the simpler biomechanical pointing task, the stochastic signatures of the normalized peak velocity were assessed across all subjects. This normalization of the peak velocity removes potential allometric effects due to differences in limb size. The results are shown on FIG. 34A on the proprioceptive map of the Gamma plane. FIG. 34B shows the shape and scale of the Gamma curves color-coded as in A. This assessment included the 22 participants from the separate control group of adults (including two college professors) spanning ages from 18 to 61 years old. Here a scaling relation was found characterizing the log-log plot of the Gamma (a, b) parameters whereby each age group formed clusters along the line within statistical classes of different stochastic signatures. Across the developmental lifespan the fit remained tight independent of whether the motion was intentionally towards or spontaneously away from the target. Using the general model $f(x)=mx^n$ with m=0.77 and n=−1.02 with 95% confidence intervals [0.6523, 0.9016] and [4.058, −0.9918], respectively. The goodness of fit parameters were SSE=5.9×10$^{-8}$, $R^2$=0.999, adjusted $R^2$=0.999 and RMSE=6.6×10$^{-5}$.

The Gamma statistics revealed significant differences in mean and variance between the self emerging clusters in FIG. 34A according to age. Notably the youngest group had the highest dispersion in the probability distribution as quantified by the Fano factor. This is a noise to signal ratio $F=\sigma^2_w/\mu_w$ taken within the time window between the movement onset and the peak velocity (on the order of 200 ms in this case). Before 4 years of age the system not only has significantly higher variance than the adult system ($p<10^{-5}$) but also operates within a very narrow window of exploration. The mean of the distribution is narrowly centered within a very small range of values of the normalized peak velocity (out of possible values in the full range). This is shown by the curves in the FIG. 34B, each one corresponding to a child. Notice that after 4 years of age the system acquires a broader exploratory range of this random parameter and the variance significantly decreases ($p<10^{-4}$) compared to the younger children. These results strongly suggest that a maturation process undergoes a pivotal change around the age of 3-4 years in which two fundamental developments take place in the somatosensing of hand pointing velocity: (1) the noise decreases, and (2) the range of exploration broadens. These two factors combined give rise to higher predictive power of upcoming velocity from past velocity. In parallel decision-making turns faster and more accurate. It is no coincidence that around this time universally children acquire the "bell-shaped" speed feature which then, as after 4 years of age, flexibly re-adapts in the face of new cognitive loads and returns once again to the stable unimodal state.

Movements that were intended to the goal had different signatures of variability than incidental movements that pursued no specific goal. Furthermore within each kind of movement functionality (intended and incidental), statistical transitions were tracked from slow-deliberate to fast-automatic motions. These movements had distinct speed profiles giving rise to shifts in the stochastic signatures of the somatosensory kinesthetic inputs with corresponding stochastic influences on the movement decision latencies. Importantly the stochastic shifts were systematic as a function of perceptual and cognitive demands, even when the kinematics goals and biomechanical demands were similar for the movement.

The statistical dissociation between movement classes was absent before the age of 4, when noise overpowered the signal, followed memoryless random processes well characterized by the exponential distribution and the range of kinematics parameters was very small. At that early age it is very unlikely, according to these empirical findings that prior beliefs can guide movement selections or cognitive decisions. In the context of Bayesian inference these empirical results suggest that priors are acquired and that they are not reliable before 4 years of age. In the context of stochastic optimality principles, the empirical data also points at the need for a maturation process before optimal decisions and selections of motor programs develop.

The present work provides power relations that characterize the human kinesthetic system using the stochastic signatures of somatosensory processes, measured at the motor output. This somatosensory readout conveys information about cognitive demands and perceptual goals when the action is deliberate and also when the action is automatic. This information serves to physically measure the types of mental processes that cognitive psychologists have previously proposed. It also establishes normative data to measure deviations from the typical course of both cognitive and somatosensory-motor development. It has been demonstrated that, across ages, one can objectively quantify the internal kinesthetic sensations that give rise to a reliable percept of the body coupled with cognitive decision making.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method for diagnosing a neurological disorder in a subject, said method comprising:
   a. presenting on a display device an artificial agent to a subject, wherein the artificial agent produces a stimulus change to the subject when the subject interacts with the artificial agent;
   b. measuring motion resulting from activation of a muscle of the subject, whereby motion measurements are produced;
   c. separating the motion measurements into a goal-directed segment associated with the artificial agent producing a first stimulus change, and a supplemental segment associated with the artificial agent not producing any stimulus change;
   d. determining automatically on a processor a first value of a distance between a first value of a statistic of the motion measurements that belong to the goal-directed segment and a second value of the statistic of the motion measurements that belong to the supplemental segment;
   e. determining automatically on a processor a measure of a neurological disorder in the subject based on a difference between the first value of the distance for the subject and a second value of the distance for a different second subject without the neurological disorder; and
   f. presenting the measure of the neurological disorder on a display device.

2. The method of claim 1, wherein said neurological disorder is an autism spectral disorder (ASD) or Parkinson's disease (PD).

3. The method of claim 1, wherein said display device is a robot or screen, and the artificial agent is a three dimensional animate, a speaker, or an image or a video.

4. The method of claim 1, wherein said artificial agent is a dynamic media or interface.

5. The method of claim 1, wherein said artificial agent provides a task to the subject.

6. The method of claim 5, wherein said task is a pointing task or a match-to-sample task.

7. The method of claim 1, wherein said subject is not provided instruction on how to interact with the artificial agent.

8. The method of claim 1, wherein said artificial agent provides a stimulus when the subject contacts a region of interest.

9. The method of claim 8, wherein said display device is a screen and the stimulus is a real-time video of the subject.

10. The method of claim 1, wherein said measuring motion resulting from activation of a muscle of the subject comprises measuring facial patterns of the subject.

11. The method of claim 1, further comprising:
   f) after said steps a through e, administering a therapy to the subject;
   g) after said administering the therapy, repeating said steps a through e to determine a post therapy measure of the neurological disorder;
   h) determining a change between the measure of the neurological disorder and the post therapy measure of the neurological disorder; and
   i) determining whether the therapy modulates the neurological disorder based on the change.

12. The method of claim 1, further comprising, after said steps a through e: changing the stimulus produced by the artificial agent to lessen the difference between the first value of the distance and the second value of the distance based on sensory feedback; and, repeating steps a through e.

* * * * *